US009655853B2

(12) United States Patent
Barnscheid et al.

(10) Patent No.: US 9,655,853 B2
(45) Date of Patent: May 23, 2017

(54) TAMPER-RESISTANT DOSAGE FORM COMPRISING PHARMACOLOGICALLY ACTIVE COMPOUND AND ANIONIC POLYMER

(71) Applicant: GRÜNENTHAL GMBH, Aachen (DE)

(72) Inventors: Lutz Barnscheid, Mönchengladbach (DE); Jessica Redmer, Mönchengladbach (DE); Sebastian Schwier, Aachen (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 15/166,573

(22) Filed: May 27, 2016

(65) Prior Publication Data

US 2016/0271066 A1      Sep. 22, 2016

Related U.S. Application Data

(63) Continuation of application No. 14/636,801, filed on Mar. 3, 2015, now abandoned, which is a continuation of application No. 13/778,186, filed on Feb. 27, 2013, now abandoned.

(60) Provisional application No. 61/603,986, filed on Feb. 28, 2012.

(30) Foreign Application Priority Data

Feb. 28, 2012  (EP) .................................... 12001301

(51) Int. Cl.
| | | |
|---|---|---|
| A61K 47/32 | (2006.01) |
| A61K 31/74 | (2006.01) |
| A61K 9/20 | (2006.01) |
| A61K 31/135 | (2006.01) |

(52) U.S. Cl.
CPC .......... *A61K 9/2027* (2013.01); *A61K 9/2031* (2013.01); *A61K 9/2054* (2013.01); *A61K 9/2077* (2013.01); *A61K 31/135* (2013.01); *A61K 47/32* (2013.01); *A61K 9/2095* (2013.01)

(58) Field of Classification Search
None
See application file for complete search history.

(56) References Cited

U.S. PATENT DOCUMENTS

| | | |
|---|---|---|
| 2,524,855 A | 10/1950 | Schnider et al. |
| 2,806,033 A | 9/1957 | Lewenstein et al. |
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,806,603 A | 4/1974 | Gaunt et al. |
| 3,865,108 A | 2/1975 | Hartop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |
| 4,629,621 A | 12/1986 | Snipes |

(Continued)

FOREIGN PATENT DOCUMENTS

| | | |
|---|---|---|
| AR | 046994 A1 | 12/2004 |
| AR | 045353 A1 | 10/2005 |
| AR | 049562 A1 | 8/2006 |
| AR | 053304 A1 | 5/2007 |
| AR | 054222 A1 | 6/2007 |
| AR | 054328 A1 | 6/2007 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |

(Continued)

OTHER PUBLICATIONS

Alekseeva et al, Chemical-Pharmaceutical Journal, vol. 41, No. 9, 2007, 49-52. (Full translation attached.)
Borquist et al., "Simulation of the release from a multiparticulate system validated by single pellet and dose release experiements," J. Controlled Release, 97: 453-465 (2004).
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.

(Continued)

*Primary Examiner* — Robert A Wax
*Assistant Examiner* — Randeep Singh
(74) *Attorney, Agent, or Firm* — Norris McLaughlin & Marcus, P.A.

(57) ABSTRACT

The invention relates to a pharmaceutical dosage form having a breaking strength of at least 300 N and comprising a pharmacologically active compound, an anionic polymer bearing carboxylic groups, wherein the content of the anionic polymer is ≥20 wt.-%, based on the total weight of the pharmaceutical dosage form, and a nonionic surfactant.

13 Claims, 5 Drawing Sheets

(56) References Cited

U.S. PATENT DOCUMENTS

| | | |
|---|---|---|
| 4,667,013 A | 5/1987 | Reichle |
| 4,690,822 A | 9/1987 | Uemura |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinity |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | McGinity et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Gradums et al. |
| 5,811,126 A | 9/1998 | Krishanamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric |

(56) References Cited

U.S. PATENT DOCUMENTS

| | | |
|---|---|---|
| 8,101,630 B2 | 1/2012 | Kumar et al. |
| 8,114,383 B2 | 2/2012 | Bartholomaeus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomeus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Maric et al. |
| 8,858,963 B1 | 10/2014 | Devarakonda et al. |
| 9,192,578 B2 | 11/2015 | McGinity et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0187192 A1* | 12/2002 | Joshi ............... A61K 9/0056 424/484 |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1* | 4/2003 | Chen ............... A61K 9/1617 424/400 |
| 2003/0091630 A1 | 5/2003 | Louie-Helm et al. |
| 2003/0092724 A1 | 5/2003 | Kao et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0185105 A1 | 9/2004 | Berner et al. |
| 2004/0213845 A1 | 10/2004 | Sugihara |
| 2004/0213848 A1 | 10/2004 | Li et al. |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogmann et al. |
| 2005/0266084 A1 | 12/2005 | Li et al. |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedmann et al. |
| 2006/0017916 A1 | 1/2006 | Clarke et al. |
| 2006/0039864 A1 | 2/2006 | Bartholomaeus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1* | 8/2007 | Breitenbach ......... A61K 9/2027 424/469 |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1* | 10/2007 | Emigh ............... A61K 9/0043 424/10.4 |
| 2007/0259045 A1 | 11/2007 | Mannion et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 4/2008 | Wada et al. |
| 2008/0085304 A1 | 4/2008 | Baichwal et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0220079 A1 | 9/2008 | Chen |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |

(56) References Cited

U.S. PATENT DOCUMENTS

| | | |
|---|---|---|
| 2008/0317695 A1 | 12/2008 | Everaert et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0117191 A1 | 5/2009 | Brown Miller et al. |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0317355 A1 | 12/2009 | Roth et al. |
| 2010/0015223 A1 | 1/2010 | Cailly-Deufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0159100 A1 | 6/2011 | Anderson et al. |
| 2011/0187017 A1 | 8/2011 | Haupts |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0028970 A1 | 1/2013 | Schwier et al. |
| 2013/0090349 A1 | 4/2013 | Gei Ler et al. |
| 2013/0129825 A1 | 5/2013 | Billoet et al. |
| 2013/0129826 A1 | 5/2013 | Gei Ler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau Maric et al. |
| 2014/0112989 A1 | 4/2014 | Bartholomäus et al. |
| 2014/0170079 A1 | 6/2014 | Arkenau Maric et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wenig et al. |
| 2015/0030677 A1 | 1/2015 | Adjei et al. |
| 2015/0064250 A1 | 3/2015 | Ghebre-Sellassie et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0374630 A1 | 12/2015 | Arkenau et al. |
| 2016/0256456 A1 | 9/2016 | Caruso et al. |

FOREIGN PATENT DOCUMENTS

| | | |
|---|---|---|
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| BR | P10413318 A | 10/2006 |
| BR | P10413361 A | 10/2006 |
| BR | P10513300 A | 5/2008 |
| BR | P10606145 A2 | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 2317747 A1 | 7/1999 |
| CA | 2343234 A1 | 3/2000 |
| CA | 2352874 A1 | 6/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 A | 12/2007 |
| CN | 101111232 A | 1/2008 |
| CN | 101175482 A | 2/2008 |

(56) References Cited

FOREIGN PATENT DOCUMENTS

| | | |
|---|---|---|
| CN | 101370485 A | 2/2009 |
| CN | 101394839 A | 3/2009 |
| CN | 101652128 A | 2/2010 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102004032103 A1 | 1/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP066345 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A1 | 8/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0761211 A1 | 3/1997 |
| EP | 0780369 A1 | 6/1997 |
| EP | 0785775 A1 | 7/1997 |
| EP | 0809488 A1 | 12/1997 |
| EP | 0820698 A1 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0980894 A1 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 A2 | 10/2002 |
| EP | 1251120 A1 | 10/2002 |
| EP | 1293127 A2 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 B1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 20070272 T3 | 11/2007 |
| JP | S36-022895 | 11/1961 |
| JP | S55162714 A | 12/1980 |
| JP | S5659708 A | 5/1981 |

(56) References Cited

FOREIGN PATENT DOCUMENTS

| | | | |
|---|---|---|---|
| JP | S56169622 A | 12/1981 |
| JP | S62240061 A | 10/1987 |
| JP | H0249719 A | 2/1990 |
| JP | 03-501737 A | 4/1991 |
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | 2002524150 A | 8/2002 |
| JP | 2002-275175 A | 9/2002 |
| JP | 2003125706 A | 5/2003 |
| JP | 2003526598 A | 9/2003 |
| JP | 2005506965 A | 3/2005 |
| JP | 2005515152 A | 5/2005 |
| JP | 2005534664 A | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009531453 A | 9/2009 |
| JP | 2009537456 A | 10/2009 |
| JP | 2011504455 A | 2/2011 |
| JP | 2011506493 A | 3/2011 |
| JP | 2013536810 A | 9/2013 |
| JP | 2014505736 A | 3/2014 |
| JP | 2014528437 A | 10/2014 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110015921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |
| RU | 2198197 C2 | 2/2003 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | 1254634 B | 5/2006 |
| WO | WO 80/00841 A1 | 5/1980 |
| WO | WO 89/05624 A1 | 6/1989 |
| WO | WO 90/03776 A1 | 4/1990 |
| WO | WO 93/06723 A1 | 4/1993 |
| WO | WO 93/10758 A1 | 6/1993 |
| WO | WO 93/10765 A1 | 6/1993 |
| WO | WO 93/11749 A1 | 6/1993 |
| WO | WO 93/23017 A1 | 11/1993 |
| WO | WO 94/06414 A1 | 3/1994 |
| WO | WO 94/08567 A1 | 4/1994 |
| WO | WO 95/17174 A1 | 6/1995 |
| WO | WO 95/20947 A1 | 8/1995 |
| WO | WO 95/22319 A1 | 8/1995 |
| WO | WO 95/30422 A1 | 11/1995 |
| WO | WO 96/00066 A1 | 1/1996 |
| WO | WO 96/03979 A1 | 2/1996 |
| WO | WO 96/14058 A1 | 5/1996 |
| WO | WO 97/00673 A1 | 1/1997 |
| WO | WO 97/33566 A2 | 9/1997 |
| WO | WO 97/49384 A1 | 12/1997 |
| WO | WO 98/35655 A3 | 2/1998 |
| WO | WO 98/20073 A1 | 5/1998 |
| WO | WO 98/28698 A2 | 7/1998 |
| WO | WO 98/35655 A2 | 8/1998 |
| WO | WO 98/51758 A1 | 11/1998 |
| WO | WO 99/12864 A1 | 3/1999 |
| WO | WO 99/32120 A1 | 7/1999 |
| WO | WO 99/44591 A1 | 9/1999 |
| WO | WO 99/45887 A2 | 9/1999 |
| WO | WO 99/48481 A1 | 9/1999 |
| WO | WO 00/13647 A1 | 3/2000 |
| WO | WO 00/33835 A1 | 6/2000 |
| WO | WO 00/40205 A2 | 7/2000 |
| WO | WO 01/08661 A2 | 2/2001 |
| WO | WO 01/12230 A2 | 2/2001 |
| WO | WO 01/15667 A1 | 3/2001 |
| WO | WO 01/52651 A2 | 7/2001 |
| WO | WO 01/58451 A1 | 8/2001 |
| WO | WO 01/97783 A1 | 12/2001 |
| WO | WO 02/26061 A1 | 4/2002 |
| WO | WO 02/26262 A2 | 4/2002 |
| WO | WO 02/26928 A1 | 4/2002 |
| WO | WO 02/35991 A2 | 5/2002 |
| WO | WO 02/071860 A1 | 9/2002 |
| WO | WO 02/088217 A1 | 11/2002 |
| WO | WO 02/094254 A2 | 11/2002 |
| WO | WO 03/006723 A1 | 1/2003 |
| WO | WO 03/013433 A2 | 2/2003 |
| WO | WO 03/013476 A1 | 2/2003 |
| WO | WO 03/013479 A1 | 2/2003 |
| WO | WO 03/013538 A1 | 2/2003 |
| WO | WO 03/015531 A2 | 2/2003 |
| WO | WO 03/018015 A1 | 3/2003 |
| WO | WO 03/024426 A1 | 3/2003 |
| WO | WO 03/024430 A1 | 3/2003 |
| WO | WO 03/026624 A1 | 4/2003 |
| WO | WO 03/026743 A2 | 4/2003 |
| WO | WO 03/028698 A1 | 4/2003 |
| WO | WO 03/028990 A1 | 4/2003 |
| WO | WO 03/031546 A1 | 4/2003 |
| WO | WO 03/035029 A1 | 5/2003 |
| WO | WO 03/035053 A1 | 5/2003 |
| WO | WO 03/035054 A1 | 5/2003 |
| WO | WO 03/035177 A2 | 5/2003 |
| WO | WO 03/039561 A1 | 5/2003 |
| WO | WO 03/049689 A2 | 6/2003 |
| WO | WO 03/053417 A2 | 7/2003 |
| WO | WO 03/068392 A1 | 8/2003 |
| WO | WO 03/070191 A1 | 8/2003 |
| WO | WO 03/092648 A1 | 11/2003 |
| WO | WO 03/094812 A1 | 11/2003 |
| WO | WO 03/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/016313 A1 | 2/2005 |
| WO | WO 2005/016314 A1 | 2/2005 |
| WO | WO 2005/032524 A2 | 4/2005 |

(56) References Cited

FOREIGN PATENT DOCUMENTS

| | | |
|---|---|---|
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/131357 A1 | 11/2007 |
| WO | WO 2008/023261 A1 | 2/2008 |
| WO | WO 2008/033523 A1 | 3/2008 |
| WO | WO 2008/069941 A2 | 6/2008 |
| WO | WO 2008/086804 A2 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/135680 A1 | 11/2009 |
| WO | WO 2010/022193 A2 | 2/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/128630 A2 | 10/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 20131156453 A1 | 10/2013 |
| WO | WO 2013/167735 A1 | 11/2013 |
| WO | WO 2014/059512 A1 | 4/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/103379 A1 | 7/2015 |

OTHER PUBLICATIONS

Cuesov, 1999, pp. 351-352.
Extended European Search Report and Opinion for Application No. EP 15153679.4-1455, Jun. 30, 2015.
Extended European Search Report and Opinion for Application No. EP 15165064.5-1455, Oct. 16, 2015.
Extended European Search Report and Opinion for Application No. EP 15165065.2-1455, Nov. 2, 2015.
Extended European Search Report and Opinion for Application No. EP 15165067.8-1455, Nov. 2, 2015.
Extended European Search Report and Opinion for Application No. EP 15165069.4-1455, Nov. 2, 2015.
Extended European Search Report and Opinion for Application No. EP 15165070.2-1455, Nov. 2, 2015.
Extended European Search Report and Opinion for Application No. EP 15184634.2-1455, Mar. 3, 2016.
Saleem et al. "Formulation and Evaluation of Tramadol hydrochloride Rectal Suppositories," Indian J. Pharm Sci. Sep.-Oct. 2008; 70(5), 640-644.
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Sidhu et al., "Watch for nonpsychotropics causing psychiatric side effects," Current Psychiatry, vol. 7, No. 4, 2008, 61-74.
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.
Vynckier et al.,"Hot-melt co-extrusion for the production of fixed-dose combination products with a controlled release ethylcellulose matrix core," International Journal of Pharmaceutics 464 (2014), 65-74.
2.9 Methoden der pharmazeutischen Technologie, European Pharmacopeia, 143-144, 1997. (Full English translation attached).

(56) References Cited

OTHER PUBLICATIONS

Albertini, B. "New spray congealing atomizer for the microencapsulation of highly concentrated solid and liquid substances" European Journal of Pharmaceutics and Biopharmaceutics 69 (2008) 348-357.
Almeida, A. et al., Ethylene vinyl acetate as matrix for oral sustained release dosage orms produced via hot-melt extrusion, European Journal of Pharmaceutics and Biosharmaceutics 77 (2011) 297-305.
Almeida, A. et al., Sustained release from hot-melt extruded matrices based on ethylene vinyl acetate and polyethylene oxide, European Journal of Pharmaceutics and Biopharmaceutics 82 (2012) 526-533.
Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.
Apicella A.et al., Biomaterials, vol. 14, No. 2, pp. 83-90, 1993.
Application of a modelling system in the formulation of extended release hydrophilic matrices, Reprinted from Pharmaceutical Technology Europe, Jul. 2006.
Application of Opadry II, complete film coating system, on metformin HCl extended release matrices containing Polyox water soluble resin, Colorcon Apr. 2009.
Arnold C., "Teen Abuse of Painkiller OxyContin on the Rise," www.npr.org, Dec. 19, 2005.
Augustine, R.L., Catalytic Hydrogenation of a, B-Unsaturated Ketones. III The Effect of Quantity and Type of Catalysts, J.Org Chem. 28(1), pp. 152-155, Abstract 1963.
Avis, Kenneth, Parenteral Preparations. Chapter 85. pp. 1518-1541In Remington's Pharmaceutical Sciences, 17th Ed, 1985.
Bailey, F.E., et al., "Some properties of poly(ethylene oxide) in aqueous solution," Journal of Applied Polymer Science, vol. 1, Issue No. 1, pp. 56-62, 1959.
Bauer et al. Lehrbuch der Pharmazeutischen Technologie. Eight Edition 2006. Stuttgart, pp. 343-352.
Bauer et al. Lehrbuch der Pharmazeutischen Technologie. Sixth Edition 1999. Stuttgart, pp. IX-XV, Table of contents. (Full English translation attached).
Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al.,"The impact of the addition of naloxone on the use and abuse of pentazocine", Public Health Reports, Jul.-Aug. 1987, vol. 102, No. 4, p. 426-429.
Bingwen et al, 2008, p. 367. (full translation attached).
Block, Lawrence. Medicated Applications. Chapter 88. In Remington's Pharmaceutical Sciences, 17th Ed, 1985.
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Bruce et al, Properties of hot-melt extuded tablet formulations for the colonic delivery of 5-aminosalicylic acid, European Journal of Pharmaceutics and Biopharmaceutics, 59 (2005) 85-97.
Caraballo, Journal of Controlled Release, vol. 69, pp. 345-355, 2000.
Carbopol 71G, retrieved Mar. 10, 2014 from http://www.lubrizol.com/LifeScience/Products/Carbopol71G-NF.html.
Cawello, "Parameters for Compartment-Free Pharmacokinetics—Standardization of Study Design, Data Analysis and Reporting" 1999, pp. XI-XIII (table of contents).
Committee for Proprietary Medicinal Products. Note for Guidance on the Investigation of Bioavailability and Bioequivalence. 2001. pp. 1-18.

Coppens et al., "Hypromellose, Ethylcellulose, and Polyethylene Oxide Use in Hot Melt Extrusion"; Pharmaceutical Technology, 62-70, Jan. 2005.
Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-melt extrusion," Biomaterials 23, 2002, pp. 4241-4248.
Crowley MM, Drug Dev Ind Pharm. Sep. 2007; 33(9):909-26. (Abstract only).
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory in Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al., Rhabdomyolysis and acute renal failure resulting from alcohol and drug abuse, Q.J. Med, vol. 93, 2000, pp. 29-33.
DeJong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only).
Dierickx et al., "Co-extrusion as manufacturing technique for fixed-dose combination mini-matrices," European Journal of Pharmaceutics and Biopharmaceutics 81 (2012), 683-689.
Disanto, Anthony. Bioavailability and Bioequivalency Testing. Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
DOW Technical Data, POLYOX WSR Solid Dosage Formulation via Melt Extrusion, Feb. 2003, pp. 1-3.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
Eggleston, "The seat of the emetic action of various drugs," J. Pharmacol. Exp. Ther. 7, 225-253 (1915).
El-Egakey, Adel et al, "Hot extruded dosage forms Part I Technology and dissolution kinetics of polymeric matrices" Pharmacerutica Acta Helvetiae, vol. 46, pp. 51-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolina, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.

(56) References Cited

OTHER PUBLICATIONS

Encyclopedia of Pharmaceutical Technology, Third Edition, vol. 6, edited by James Swarbrick PharmaceuTech, Inc., Pinehurst, North Carolina, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde. Quality Assurance and Control. Chapter 83, pp. 1487-1491 In Remington's Pharmaceutical Sciences, 17th Ed, 1985.
Eudragit NE40D web page from Evonik website; downloaded Feb. 24, 2015.
Eudragit RS PO web page from Evonik website; downloaded Feb. 24, 2015.
European Pharmacopeia 5.0; Glyceryl behenate monograph; dated Jan. 2005; downloaded Feb. 24, 2015.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Opinion Application No. 12002708. 1-1219, Sep. 24, 2012.
European Search Report and Opinion Application No. 14176277. 3-1460, Dec. 15, 2014.
European Search Report and Opinion, Application No. 11006253. 6-2112, Dec. 16, 2011.
European Search Report and Opinion, Application No. 11006254. 4-2112, Dec. 16, 2011.
European Search Report and Opinion, Application No. 11008131. 2-1219, Feb. 24, 2012.
European Search Report and Opinion, Application No. 11009129. 5-2112, Apr. 10, 2012.
European Search Report and Opinion, Application No. 12001296. 8-1219, Jun. 26, 2012.
European Search Report and Opinion, Application No. 12001301. 6-1219, Jun. 26, 2012.
European Search Report and Opinion, Application No. 12003743. 7-1219, Sep. 24, 2012.
European Search Report and Written Opinion for EP Application No. 14169801.9-1455 Oct. 20, 2014.
European Search Report and Written Opinion for EP Application No. 13169658.5, Aug. 6, 2013.
European Search Report and Written Opinion for EP Application No. 13169659.3, Aug. 6, 2013.
European Search Report and Written Opinion for EP Application No. 13176309.9-1460, Oct. 9, 2013.
European Search Report and Written Opinion for EP Application No. 13197503.9-1460, Feb. 18, 2014.
European Search Report and Written Opinion for EP Application No. 13425151.1-1460, Mar. 11, 2014.
Evaluation of Verapamil HCI (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).
Evonik Rohm GmbH product brochure: EUDRAGIT acrylic polymers for solid oral dosage forms (2009).
Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier, N. et al., "Various ways of modulating the release of ditiazem hydrochloride from hot-melt extruded sustained release pellets prepared using polymeric materials" Journal of Controlled Release 36, pp. 243-250, 1995.
Formulation of Polyox ER Matrices for a Highly Soluble Acgtive, Colorcon Jul. 2009.
Foye, W., Principles of Medicinal Chemistry; Analgesics pp. 241-242, at 241 (1989).
Foye, W., Prinicples of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Giles R. et al. Plastic Packaging Materials. Chapter 81. pp. 1473-1477 In Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioquivalence, FDA, BP, Jan. 2001.
Handbook of Pharmaceutical Excipients, 1986, American Pharmaceutical Association, Washington, DC and London (Table of Contents Only).
Handbuch der Kunststoff-Extrusionstechnik 1, "Grundlagen" in Chapter 1.2 "Klassifizierung von Extrudern", pp. 3-7. 1989. (Full english translation attached).
Hanning C.D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release. 2001, vol. 75, pp. 391-400.
Hoepfner et al. Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia, Dec. 2009, pp. 1-3.
Investigation of a Directly Compressible Metformin HCI 500mg Extended Release Formulation Based on Hypromellose, Colorcon Jul. 2009.
James, A. "The legal and clinical implications of crushing tablet medication", Nurse Times 100(50), 28-33, 2004.
Janicki S. et al. "Slow-Release Microballs: Method of Preparation", Acta Pharm. Technol. 33 (3) 154-155, 1987.
Jannetto, P. et al, "Oxycodone: Recognition and Pharmacogenomics," Toxicology News, Mar. 2003, 1-7.
Kalant H. et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).

(56) References Cited

OTHER PUBLICATIONS

Kim C.-J. "Drug Release from Compressed Hydrophilic Polyox-WSR Tablets" J Pharm. Sciences 1995, 84(3): pp. 303-306.
Kim N. et al. "Preparation and Evaluation of Eudragit Gels. V. Rectal Gel Preparations for Sustained Release and Avoidance of First-Pass Metabolism of Lidocaine", Chem. Pharm Bull. 1992, 40(10), 2800-2804.
King et al. Oral Solid Dosage Forms. Chapter 90. pp. 163-1632 In Remington's Pharmaceutical Sciences, 17th Ed, 1985.
King, R, "Tablets, Capsules, and Pills" Remington's Pharmaceutical Sciences, pp. 1553-1593, Ch. 89, 1980, 16$^{th}$ Edition.
King, Remington's Pharmaceutical Sciences 17th ed., Chapter 78, p. 1418 (1985).
Knevel, Adelbert. Separation. Chapter 78. pp. 1432-1442 In Remington's Pharmaceutical Sciences, 17th Ed, 1985.
Kolter, K., "Compression Behaviour of Kollidon SR," APV/ APGI 2002, Florence, Apr. 11, 2002.
Kondrat, T. , "Technology dosage forms" Moscow 1991, p. 96.
Lee, Y.-S. et al., Principles of Terahertz Science and Technology (Lecture Notes in Physics), Springer; 1 edition 2008. (Table of Contents Only).
Lenindzer, A., "The molecular basis of the structure and functions of cells" Moscow 1974, p. 68.
Levina et al., "The Effect Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded, 1990. vol. 2 (Cover and Table of Contents only).
Lintner, Carl. Stability of Pharmaceutical Products. Chapter 82. pp. 1478-1486 In Remington's Pharmaceutical Sciences, 17th Ed, 1985.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharmaceuticals and Health Care Products"; Blackie Academic & Professional; First Edition 1996. (Table of contents only).
Longer et al. Sustained-Release Drug Delivery Systems. Chapter 92. pp. 1611-1661 In Remington's Pharmaceutical Sciences, 17th Ed, 1985.
Madorsky S.L. "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C.. Therapeutic Potential of Capsaicin-like Molecules. Life Sciences, vol. 51, pp. 1777-1781, 1992.
Mank R. et al., "Darstellung wirkstoffhaltiger Extrusionsformlinge auf der Basis von hermoplasten. Teil 1: Untersuchung zur Wirkstoffliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2: Unersuchungen zur Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
McGary, C.W.. Jr. "Degradation of Poly(ethylene Oxide)", Journal of Polymer Science vol. XLVI,1960, pp. 51-57.
McGinity et al., Hot-Melt Extrusion as a Pharmaceutical Process, American Pharmaceutical Review, vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-963.
Mesiha M.S. et al "A Screening Study of Lubricants in Wet Powder Passes Suitable for extrusio-spheronization", Drug Development and Industrial Pharmacy, 19(8), pp. 943-959, 1993.
Metformin Hydrochloride 1000 mg Extended Release Tablets, Lubrizol Advanced Materials, Inc., Nov. 20, 2009, Previous Edition Dec. 19, 2008.
Metformin Hydrochloride 750 mg Extended Release Tablets, Lubrizol Advanced Materials, Inc., Sep. 2010.
Miles, R.E. et al., Terahertz Frequency Detection and Identification of Materials and Objects (NATO Science for Peace and Security Series B: Physics and Biophysics), Springer; 1 edition 2007. (Table of contents).
Miller "To crush or not to crush? What to consider before giving medications to a patent with a tube or who has trouble swallowing", Nursing, pp. 50-52, Feb. 2000.
Mises á jour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Monolithic: retrieved from internet: http:/merriam-webster.com/dictionary/monolithic. Retrieved on Sep. 2, 2015.
Moorman-Li, R. et al, "A Review of Abuse-Deterrent Nonmalignant Pain." Pharmacy and Therapeutics, vol. 37 No. 7, Jul. 2012, pp. 412-421.
Morissette et al. Advanced Drug Delivery Review 26 (2004), 275-300.
Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations. Chapter 87. pp. 1553-1563; In Remington's Pharmaceutical Sciences, 17th Ed, 1985.
Munjal M. et al., "Polymeric Systems for Amorphous Delta$^\wedge$9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, In Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.
Oliveira et al., "Production and characterization of laminar coextrudates at room temperature in the absence of solvents," AAPS Annual Meeting and Exposition, Oct. 14-18, 2012, Chicago, USA.
Oxicotin: Balancing Risks and Benefits, United States Senate, Hearing, Feb. 12, 2002.
Oxycodon (Oxygesic): Missbrauch, Abhaengigkeit und toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.

(56) References Cited

OTHER PUBLICATIONS

Ozeki T. et al. "Controlled Release From Solid Dispersion Composed of Poly(ethylene oxide)-Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviylpolymer interpolymer complex by varying molecular wight of poly(ethylene oxide)" Journal of Controlled Release 58, pp. 87-95, 1999.
PCT International Search Report and Written Opinion for PCT Application No. PCT/EP2014/064830 dated Aug. 6, 2014.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
PCT International Search Report and Written Opinion for PCT Application No. PCT/EP2010/004459 dated Dec. 1, 2010.
PCT International Search Report and Written Opinion for PCT Application No. PCT/EP2009/003290 dated Jul. 9, 2009.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical tScientists, Sep. 1989, 6(9), S-98.
Pharm. Research, Official Journal of the American Association of Pharmaceutical Scientists, Oct. 1991, 8(10), S-192.
Phillips, G. Briggs. Sterilization. Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives rom a simple monolithic system. Journal of Controlled Release. 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008. (Table of Contents only).
Polyox water soluble resins 2003. http://www.dow.com/webapps/lit/litorder.asp?filepath=polyox/pdfs/noreg/326-00002.pdf.
POLYOX water-soluble resins (DOW Mar. 2002); see http://msds-search.dow.com/PublishedLiteratureDOWCOM/dh_0031/0901b8038003 1a4a.pdf?filepath=/326-00001.pdf &fromPage=GetDoc).
POLYOX WSR-303, retrieved Mar. 10, 2014 from URL http://www.dow.com/dowwolff/en/industrial_solutions/polymers/polyethylene.
POLYOX, COLORCON, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Porter, S. Coating of Pharmaceutical Dosage Forms. Chapter 91. pp. 1633-1643 In Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs as First Priority; New Drug Application Delayed," www.headaches.about.com, Jun. 18, 2002, pp. 1-6.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka MA, Drug Dev Ind Pharm. Oct. 2007; 33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippie, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung. 2nd Edition, 2002, Ch 6, pp. 515-519. (Full English translation attached).
Ritschel et al. Die Tablette: Handbuch der Entwicklung, Herstellung und Qualitatssicherung. 2nd Edition, 2002, Ch 6, pp. 69-82 and 115-136.
Ritschel et al. Die Tablette: Handbuch der Entwicklung, Herstellung und Qualitatssicherung. 2nd Edition, 2002, Table of content.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013). pp. 1250-1258.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Salomies et al., "Determination of Oxycodone Hydrochloride in Oral Solutions by High-Performance Thin-Layer Chromatography/Densitometry," Journal of AOAC International, 83: 1497-1501 (2000).
Sax et al., Hawley's Condensed Chemical Dictionary, 11th ed., 1987, p. 1233, definition of "wax".
Scheirs J., et al."Characterizing the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended-Release Nifedipine" The Annals of Pharmacotherapy vol. 37, 1420-1423, Oct. 2003.
Schroeder J., et al. Granulierung hydrophober Wirkstoffe im Planetwalzenextruder, Pharm. Ind. 2003, vol. 65, No. 4, 367-372. (Full English translation attached).

(56) References Cited

OTHER PUBLICATIONS

Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCI From Melt extruded Polyethylene Disks", Pharmaceutical Research, Oct. 1991, vol. 8, No. 10, p. S-192.
Siegel, P. Tonicity, Osmoticity, Osmolality, and Osmolarity, Chapter 80. pp. 1454-1472 In Remington's Pharmaceutical Sciences, 17th Ed, 1985.
Silver, J. "Painkiller OxyContin most commonly abused prescription drug on the streets of Western Pennsylvania", Pittsburg Post-Gazette, Apr. 8, 2001.
Spassov et al., Stereochemistry of Diastereomeric 3-Dialkylaminopropanols and O-Derivatives, J.f. prakt. Chemie, 325:5, 793-800 (1981).
Sprockel O.L et al. "Permeability of Cellulose Polymers: Water Vapour Transmission Rates"., J. Pharma. Pharmacol. 42, pp. 152-157, 1990.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., Überzogene feste Formen, 1991, 347-68. (English translation attached).
Strang, Abuse of buprenorphie (Temgesic) by snorting, Letter to the editor, British Med. J., 302: 969 (1991).
Stringer J.L., et al "Diffusion of small molecular weight drugs in radiation-crosslinked poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 68, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).
Third Party Observations filed with EPO for Patent EP658055B1, Feb. 2, 2009, pp. 1-8.
Thoma V.K. et al. "Bestimmung der In-vitro—Freigabe von schwach basischen Wirkstoffen aus Ratardarzneiformen", pp. 299-301, Pharm. Ind. 51, Nr. 3, 1989.
Tikhonov, A. et al, Biopharmacy. The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra-low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. pp. 1542-1552, In Remington's Pharmaceutical Sciences, 17th Ed, 1985.
US Pharmacopoeia, Chapter 1217, Aug. 12, 2008.
Varma et al, Factors Affecting Mechanism and Kinetics of Drug Release from Matrix-Based Oral Controlled Drug Delivery Systems, Am. J. Drug Deliv. 2004:2 (1): 43-57.
Vippagunta et al. Crystalline Solids, Advanced Drug Delivery Review 48 (2001), 3-26.
Wade and Weller, "Handbook of Pharmaceutical Excipients: 2nd Edition", The American Pharmaceutical Association and The Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart—N.Y., 1982, pp. 82-92 (Full English Translation attached).
Wagner, Pharmazeutische Biologie—Drogen und ihre Inhaltsstoffe—Scharfstoffdrogen, 2nd., revised edition, Gustav Fischer Verlag, Stuttgart—N.Y., 1982, Table of Content.
Waltimo, et al, "A novel bite force recorder and maximal isometric bite force values for healthy young adults", Scandinavian Journal of Dental Research 1993; 101:171-175.
Waltimo, et al, "Maximal bite force and its association with signs and symptoms of craniomandibular disorders in young Finnish non-patients", ACTA Odontol Scand 53 (1995): 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 164(1): pp. 173-174 (2007).
Weiss, U., "Derivatives of Morphine. I 14-Dihydroxydihydromorphinone," J. Am. Chem. Soc. 77, pp. 5891-5892, Nov. 20, 1955.
West, Anthony R., Solid state chemistry and its applications, Wiley, New York, 1988, pp. 358 and 365.
Wikipedia—Dextromethorphan Aug. 12, 2013 (and attached related English-language entry dated Dec. 11, 2013).
Woodburn, K.R. et al., Vascular complications of injecting drug misuse, Br. J. of Surgery, vol. 83, 1996, pp. 1329-1334.
Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.

(56) References Cited

OTHER PUBLICATIONS

Yarbrough et al, Letters to Nature "Extraordinary effects of mortar- and -pestle grinding on microstructure of sintered alumina gel", Nature 322, pp. 347-349 (Abstract only) (Jul. 24, 1986).

Yen et al., Stability of Morphine in Aqueous Solution III: Kinetics of Morphine Degradation in Aqueous Solution, Wiley Subscription Services, Inc., Journal of Pharmaceutical Sciences, 50(1):35-42 (1961).

Zeezhan, F and N. Bukhari, "Development and Evaluation of a Novel Modified-Release Pellet-Based Tablet System for the Delivery of Loratadine and Pseudophedrine Hydrochloride as Model Drugs," AAPS PharmSciTech 11(2); 910-916 (available on-line May 22, 2010).

Zhang et al., "Properties of Sustained-Release Tablets Prepared by Hot-Melt Extrusion" Pharmaceutical Development and Technology, 1999, 4(2), 241-250.

Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opiods; 7 pages.

Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.

Cuesov, Drug Production Technology, Khar'kov, 1999, pp. 351-352. (Full ranslation attached.).

Fathima, N. et al. "Drug-excipient interaction and its importance in dosage form development," Journal of Applied Pharmaceutical Science 01 (06); 2011, pp. 66-71.

Schilling, et al., "Novel application of hot-melt extrusion for the preparation of monolithic matrices containing enteric-coated particles." International Journal of Pharmaceutics 400 (2010) 34-31.

Starch 1500, Partially Pregelatinized Maize Starch, technical data from Colorcon, Feb. 2016, 6 pages.

Cuesov, Drug Production Technology, Kharkov, 1999, pp. 351-352.

Decision of the United States District Court for the Southern District of New York, in In re *Oxycontin Antitrust Litigation, Purdue Pharma LP v. Teva Pharmaceuticals*, Findings of Fact and Conclusions of Law, District Judge Sidney H. Stein, New York, New York, Jan. 14, 2014.

Makki, A, et. al., Eds., A Dictionary of American Idioms, 4th Ed. Barron's, New York 2004), 342-343.

Al-Angari, A. et al. "The compaction properties of polyethylene glycols," J Pharm. Pharmacol. (1985) 37:151-153.

Al-Nasassrah et al., "The effect of an increase in chain length on the mechanical properties of polyethylene glycols," European Journal of Pharmaceutics and Biopharmaceutics 46 (1998) 31-38.

Anderson, S.L. et al., "A Model for Antiplasticization in Polystyrene," Macromolecules 8:2944-54 (1995).

Back, D.M.et al., "Ethylene Oxide Polymers", in Kirk-Othmer Encyclopedia of Chemical echnology. 2000, John Wiley & Sons, Inc., vol. 10, 673-696.

Balogh, Tastes in and Tastes of Paprika, in Taste: Proceedings of the Oxford Symposium on Food and Cookery 28 (Tom Jaine Ed. 1988).

Bailey, F.E., et al., "High Molecular Weight Polymers of Ethylene Oxide" Solution Properties Industrial and Engineering Chemistry, 1958. 50(1): 8-11.

Baumann, T., "Pain Management," Pharmacotherapy: A Pathophysiologic Approach (J.T. DiPiro et al. eds., McGraw-Hill 4th ed. 1999), Ch. 56, 1014-1026.

Baumrucker, S.J., "OxyContin, the Media, and Law Enforcement", American Journal of Hospice & Palliative Care, 18: 154-156 (May/Jun. 2001).

Choi, S. et al, "Hydrophilic Matrix Formulations of Dihydrocodeine Bitartrate with Polyethylene Oxide by Direct Compression," Proceedings of the 29$^{th}$ Annual Meeting of the Controlled Release Society, in collaboration with the Korea Society for Biomaterials, Minneapolis, 1$^{st}$ Edition, 2002, 984-985.

Choi, S.U., et al., "Development for a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.

Ciccone, P. E., "Attempted Abuse of Concerta," Letters to the Editor, J. Am. Acad. Child Adolesc. Psychiatry, 41:7 (Jul. 2002). Controversies in ADHD: A Breakfast Symposium—Concerta.

Crowley M. et al. Pharmaceutical Applications of Hot-Melt Extrusion: Part I. Drug Dev. & Indus. Pharmacy (2007) 33:909-926.

Crowley M., "Physiochemical and Mechanical Characterization of Hot-Melt Extruded Dosage Forms." Dissertation presented to the Faculty of the Graduate School of The University of Texas at Austin. (May 2003).

Crowley, M. et al., "Properties of Hot-Melt Extruded CPM Tablets Using Hydrophilic Polymers," poster presentation, (2000).

Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).

CROWLEY0000001-CROWLEY0000127.

Joint Claim Construction and Prehearing Statement, dated Jul 11, 2014. *Janssen Pharmaceuticals, Inc. and Grünenthal GMBH v. Actavis Elizabeth LLC and Alkem Laboratories Limited*, Civil Action No. 2.13-cv-04507 CCC-MF (D.N.J.), *Janssen Pharmaceuticals, Inc. and Grünenthal GMBH v. Roxane Laboratories, Inc.*, Civil Action No. 2:13-cv-06929 CCC-MF (D.N.J.), and *Janssen Pharmaceuticals, Inc. and Grünenthal GMBH v. Alkem Laboratories Limited*, Civil Action No. 2:13-cv-07803 CCC-MF (D.N.J.).

Davies, N. "Sustained Release and Enteric Coated NSAIDs: Are They Really GI Safe?" J. Pharm. & Pharmaceut. Sci., 2(1):5-14, 1999.

Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.

Declaration of Dr. James W. McGinity, dated Oct. 28, 2009; online, retrieved from: http://www.accessdata.fda.gov/dmgstfda_docs/labeV2013/021121s032lbl.pdf.

Dimitrov, M, et al., "Study of Verapamil hydrochloride release from compressed hydrophilic Polyox-Wsr tablets." Int'l J Pharmaceutics (1999) 189:105-111.

Dittmer, D.K., et al., "Glue-Sniffing Neuropathies," Canadian Family Physician 39:1965-1971 (1993).

Donnelly, C.L., "ADHD Medications: Past and Future," Behavioral Health Management, May/Jun. 2002, 28 & 30.

Dow, "Material Safety Data Sheet: POLYOX(TM) WSR 30" (effective date: Sep. 18, 2001).

Dow, "POLYOX Water-Soluble Resins: Degradation of Water-Soluble Resins," Technical Data (Oct. 2002).

Drug Bank "Oxymorphone," 2015; online, available at: www.dmgbank.ca/chugs/db01192 printed Jul. 1, 2015.

*Endo Pharmaceuticals Inc. v. Teva Pharmaceuticals USA, Inc.* (S.D.N.Y 2015)—Redacted Version.

FDA News Release, "FDA approves abuse-deterrent labeling for reformulated OxyContin," Apr. 16, 2013, available at http://www.fda.gov/NewsEvents/Newsroom/Press.Announcements/ucm348252.htm.

FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.

Greenhill, L.L., et al., "Practice Parameter for the Use of Stimulant Medications in the Treatment of Children, Adolescents, Child Adolescents, and Adults," J. Am. Acad. Child Adolesc. Psychiatry, 41:2 Supplement, 26S-49S (Feb. 2002).

Griffith, D., "Potential new ADHD drug creating lots of big hopes," Sacramento Bee (California), Oct. 30, 2002.

Huang, H. et al., "Preparation of Controlled Release Oral Dosage Forms by Low Temperature Melt Extrusion," AAPS PharmSci. 2000 2(S1).

National Drug Intelligence Center Information Bulletin "OxyContin Diversion and abuse" Jan. 2001.

(56) References Cited

OTHER PUBLICATIONS

Jaffe, S.L., "Failed Attempts at Intranasal Abuse of Concerta," Letters to the Editor, J. Am. Acad. Child Adolesc. Psychiatry, 41:1 (Jan. 2002).

Kibbe, Coloring Agents, in Handbook of Pharmaceutical Excipients (3rd ed. 2000).

Kidokoro, M. et al., "Properties of Tablets Containing Granulations of Ibuprofen and Acrylic Copolymers Prepared by Thermal Processes," Pharm Dev. and Tech., 6:263-275 (2001).

Kinjo, N. et al, "Antiplasticization in the Slightly Plasticized Poly(vinly chloride)," Polymer Journal 4(2):143-153 (1973).

Larhib, H. et al., "Compressing polyethyelene glycols: the effect of compression pressure and speed," Int'l J Pharmaceutics (1997) 147: 199-205.

Lieberman, H., et al., Pharmaceutical Dosage Forms: Tablets, vol. 2, Ch. 5: Granulation Technology and Tablet Characterization (1990), Table of contents and 245-348.

Lyons et al., "Twitch Interpolation in the Assessment of the Maximum Force-Generating Capacity of the Jaw-Closing Muscles in Man," Arch. Oral. Biol. 41:12, 1161-1168 (1996).

Markovitz, H., et al. "Calculations of Entanglement Coupling Spacings in Linear Polymers." Journal of Physical Chemistry, 1962. 66(8): 1567-1568.

McCrum, N., et al., Principles of Polymer Engineering. 2nd ed., New York: Oxford University Press. 447(1997), Chapter 7, 296-351.

McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.

McQuay, H. et a. "Methods of Therapeutic Trials," Textbook of Pain 1125-1138 (P.D. Wail & R. Meizack eds., Elsevier 4th ed. 1999), Table of Contents and 1125-1138.

Miura et al., "Comparison of Maximum Bite Force and Dentate Status Between Healthy and Frail Elderly Persons," J. Oral Rehabilitation, vol. 28 (2001), pp. 592-595.

Miyagawa, Y. et al., "Controlled-release of diclofenac sodium from wax matrix granulate," Int'l J. Pharmaceutics (1996) 138:215-224.

Payne, H. et al., Denatonium Benzoate as a Bitter Aversive Additive in Ethylene Glycol and Methanol-Based Automotive Products, SAE Technical Paper 930589, Abstract (1993).

Pilpel, N., et al. "The effect of temperature on the tensile strength and disintegration of paracetamol and oxytetracylcine tablets," J Pharm Pharmac., 29:389-392 (1977).

Polyox Water-Soluble Resins NF in Pharmaceutical Applications, Dow Chemical Company, Aug. 2002.

Final Draft Labeling for Concerta Extended-Release Tablets Attachment to Approval Letter (2000); available at: http://www.accessdata.fda.gov/drugsatfda_docs/label/2000/21121lbl.pdf.

Purdue Pharma LP Material Safety Data Sheet, OxyContin Tablets, 10 mg, 20 mg, 30 mg, 40 mg, 60 mg, Version 16—Sep. 2010; available at www.purduephruma.com/msdss/oxycontin_msds.pdf.

Repka, M. et al. Pharmaceutical Applications of Hot-Melt Extrusion: Part II. Drug Dev. & Indus. Pharmacy (2007) 33:1043-1057.

Rauwendaal, Chris, PHD, Responsive Expert Report of Chris Rauwendaal, Ph.D. Regarding Expert Report of Michael M. Crowley, Ph.D., dated Jul. 17, 2015.

Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.

Seitz, J.A.; et al., "Evaluation of the Physical Properties of Compressed Tablets 1: Tablet Hardness and Friability," J. of Pharm. Sci., 54:1353-1357 (1965).

Shah, et al., "Some Effects of Humidity and Heat on the Tableting Properties of Microcrystalline Cellulose Formulations 1," J. of Pharm. Sci., 57:181-182 (1967).

Singhal, et al., Handbook of Indices of Food Quality and Authenticity (1997), "Capsicum" p. 398-299.

Smith, K.L. et al., "High Molecular Weight Polymers of Ethylene Oxide—Plastic Properties." Industrial and Engineering Chemistry, 1958. 50(1): 12-16.

Tapentadol Pre-Review Report, Expert Committee on Drug Dependency Thirty-Fifth Meeting Hammamet, Tunisia, Jun. 4-8, 2012, available at http://www.who.int/medicines/areas/quality_safety/5.2Tapentadolpre-review.pdf.

Tiwari, D., et al., "Evaluation of polyoxyethylene homopolymers for buccal bioadhesive drug delivery device formulations." AAPS Pharmsci, 1999. 1(3): Article 13.

Wilkins, J.N., "Pharmacotherapy of Schizophrenia Patients with Comorbid Substance Abuse," Schizophrenia Bulletin, 23:215-228 (1997).

World Health Org., Cancer Pain Refliel With a Guide to Opioid Availability (2d ed. 1996).

Yin, T.P., et al., "Viscoelastic Properties of Polyethylene Oxide in Rubber-Like State." Journal of Physical Chemistry, 1961. 65(3): 534-538.

Zacny, J. et al. Drug & Alcohol Dependence (2003) 69:215-232.

Zhang, F., "Hot-Melt Extrusion as a Novel Technology to Prepare Sustained-Release Dosage Forms," Dissertation University of Texas at Austin, Dec. 1999.

Remington, Chapter 45, pp. 996-1035.

U.S. Court of Appeals, Federal Circuit, *Purdue Pharma L.P.* v. *Epic Pharma, LLC*, 117 USPQ2d 1733 (Fed. Cir. 2016).

Decision of the United States District Court for the Southern District of New York, in In re *Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York, Jan. 14, 2015.

Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.

Extended European Search Report for Application No. EP 16183922.0-1460, Oct. 31, 2016.

Efentakis et al, Effects of Excipients on Swelling and Drug Release from Compressed Matrices, in Drug Development and Industrial Pharmacy 23(1):107-112, Jan. 1997, Abstract.

\* cited by examiner

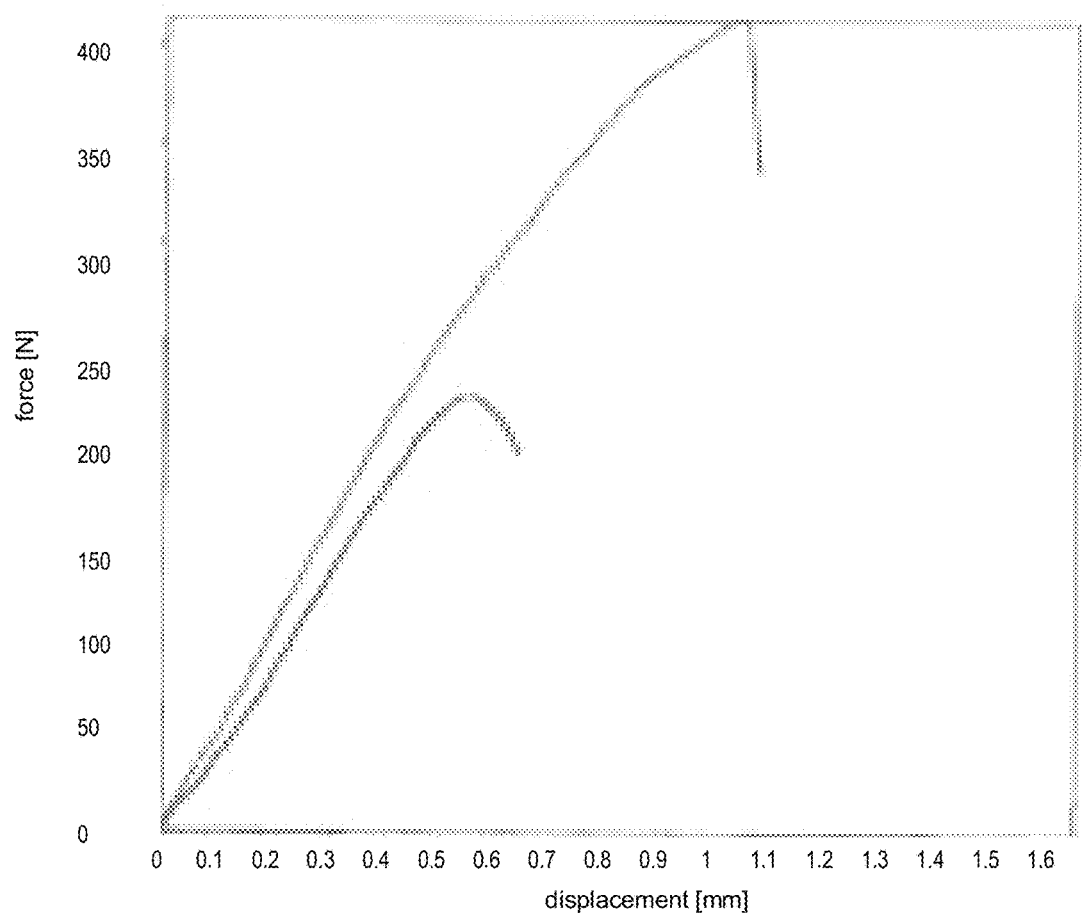

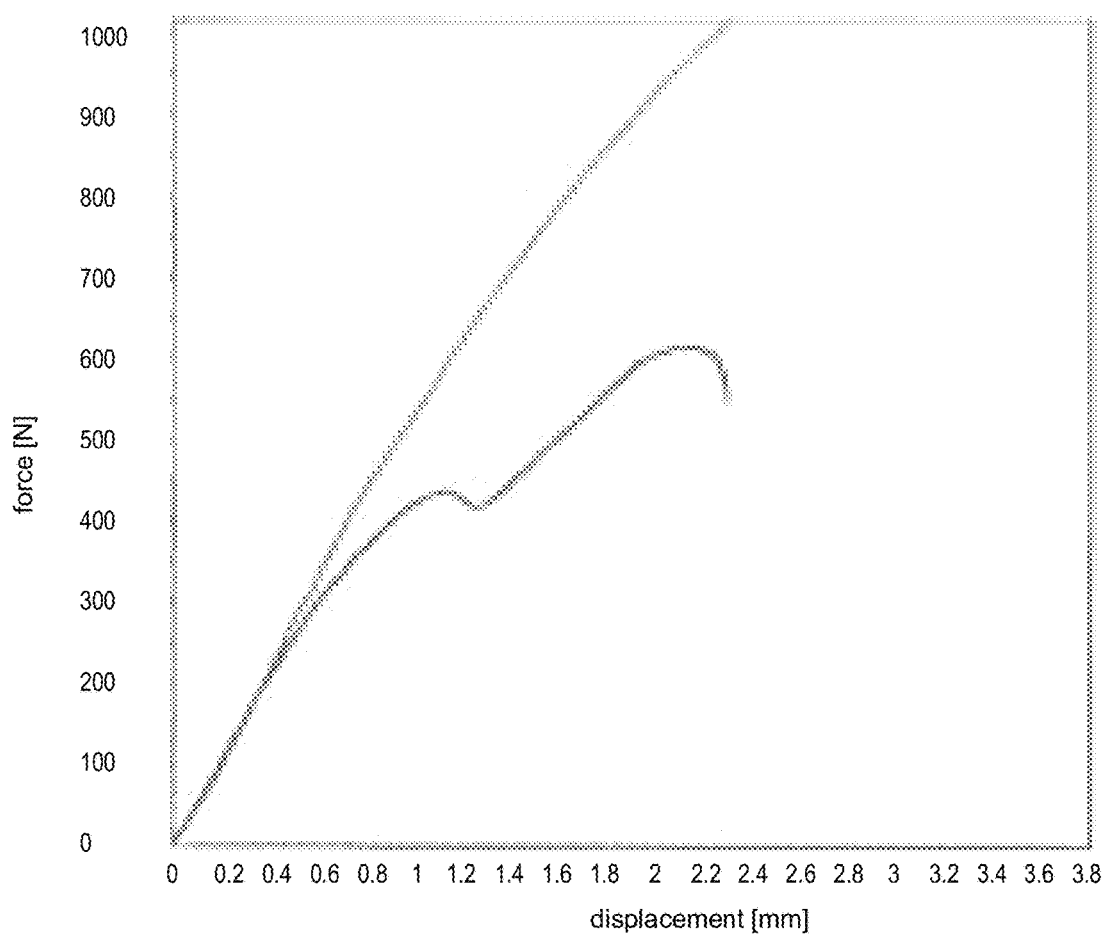
FIG. 1-B

FIG. 1-C
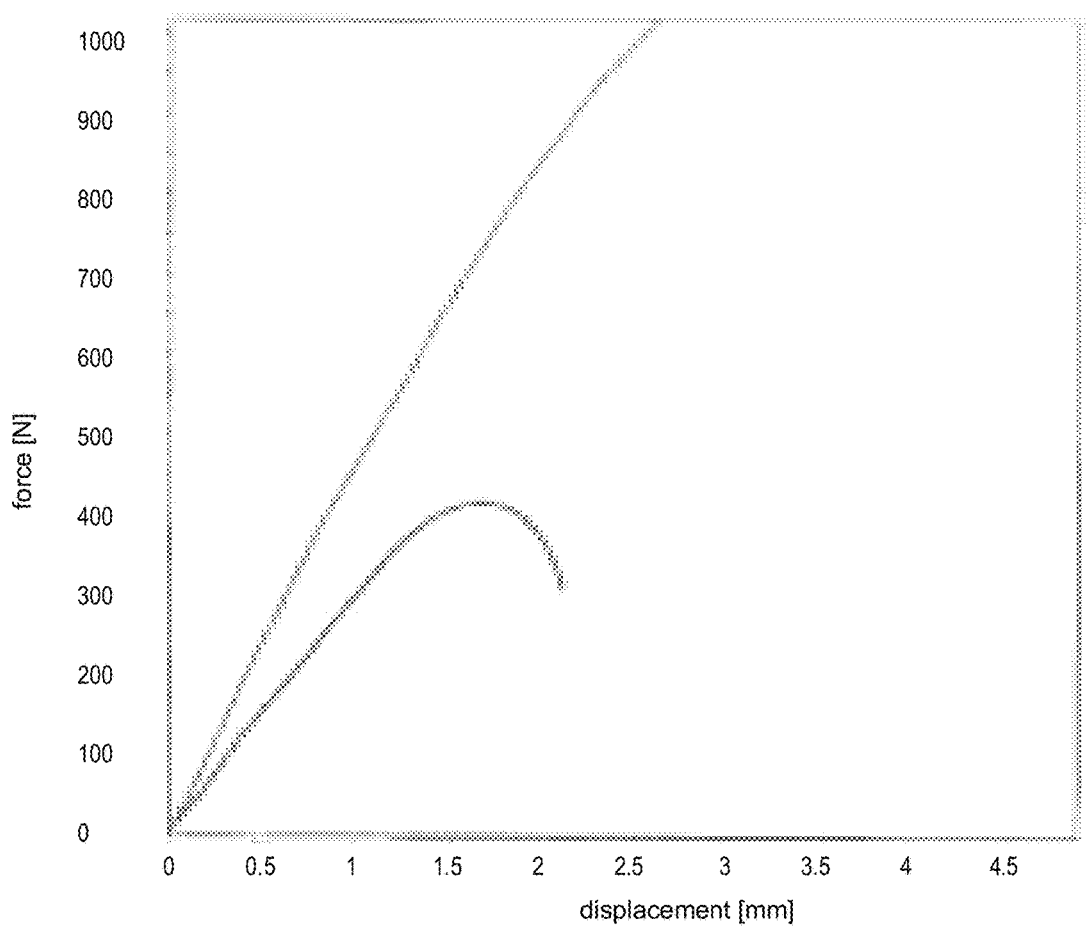

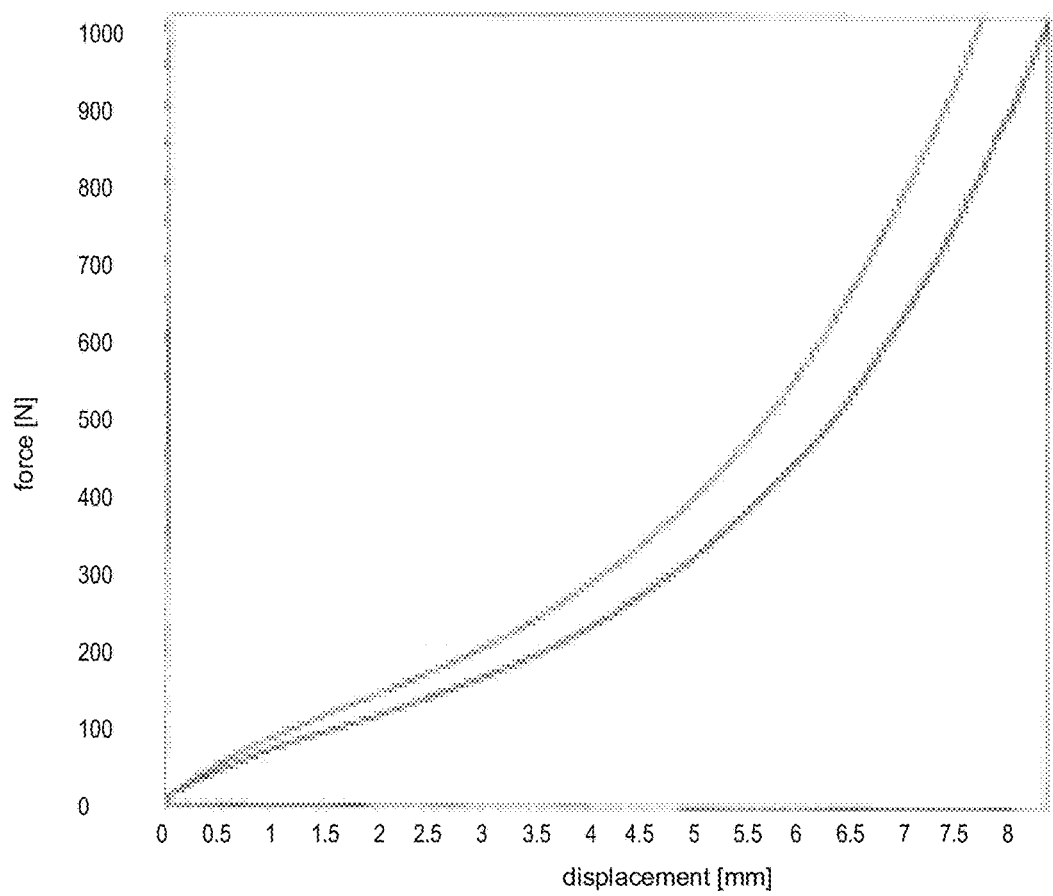
FIG. 1-D

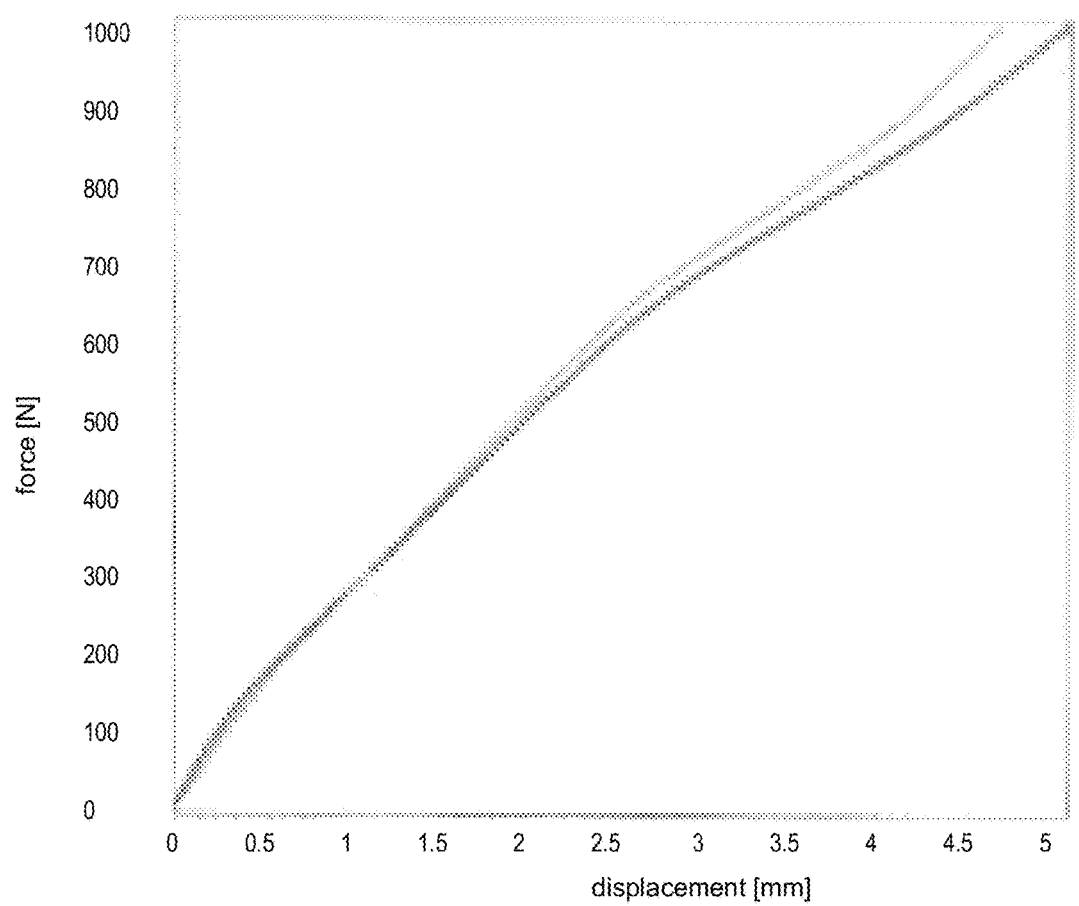
FIG. 1-E

TAMPER-RESISTANT DOSAGE FORM COMPRISING PHARMACOLOGICALLY ACTIVE COMPOUND AND ANIONIC POLYMER

This application is a continuation of U.S. Nonprovisional application Ser. No. 14/636,801, filed Mar. 3, 2015, pending, which is a continuation of U.S. Nonprovisional application Ser. No. 13/778,186, filed Feb. 27, 2013, now abandoned, which claims priority of U.S. Provisional Patent Application No. 61/603,986, filed on Feb. 28, 2012, and European Patent Application No. 12 001 301.6, filed on Feb. 28, 2012, the entire contents of which patent applications are incorporated herein by reference.

The invention relates to a pharmaceutical dosage form having a breaking strength of at least 300 N and comprising a pharmacologically active compound, an anionic polymer bearing carboxylic groups, wherein the content of the anionic polymer is ≥20 wt.-%, based on the total weight of the pharmaceutical dosage form, and a nonionic surfactant.

Tamper-resistant pharmaceutical dosage forms containing pharmacologically active compounds have been known for many years. Pharmacologically active compound abuse with conventional dosage forms is typically achieved by (i) pulverization of the pharmaceutical dosage form and nasal administration of the powder; (ii) pulverization of the pharmaceutical dosage form, dissolution of the powder in a suitable liquid and intravenous administration of the solution; (iii) pulverization of the pharmaceutical dosage form and inhalation by smoking; (iv) liquid extraction of the drug from the pharmaceutical dosage form and intravenous administration of the solution; and the like. Accordingly, many of these methods of abuse require the mechanical destruction of the pharmaceutical dosage form in order to render it suitable for abuse.

In the past several different methods have been developed to avoid drug abuse.

Some of these concepts of rendering pharmaceutical dosage forms tamper resistant rely on the mechanical properties of the pharmaceutical dosage forms, particularly a substantially increased breaking strength (resistance to crushing). The major advantage of such pharmaceutical dosage forms is that comminuting, particularly pulverization, by conventional means, such as grinding in a mortar or fracturing by means of a hammer, is impossible or at least substantially impeded. Thus, by conventional means that are available to an abuser, such pharmaceutical dosage forms cannot be converted into a form suitable for abuse, e.g. a powder for nasal administration. In this regard it can be referred to e.g., WO 2005/016313, WO 2005/016314, WO 2005/063214, WO 2005/102286, WO 2006/002883, WO 2006/002884, WO 2006/002886, WO 2006/082097, WO 2006/082099, and WO 2008/107149.

These known tamper resistant pharmaceutical dosage forms, however, are not satisfactory in every respect.

The tamper resistance of these known pharmaceutical dosage forms substantially relies on the presence of high molecular weight polyalkylene oxide, in particular polyethylene oxide, as matrix material, and further depends on the manufacturing process. In order to achieve a high breaking strength, the manufacturing process typically includes the application of heat and pressure to a preformed mixture comprising polyalkylene oxide and pharmacologically active substance, and requires careful selection of the process conditions.

In tablet formulations, acrylic acid polymers (carbomers) are used in concentrations up to 10 wt.-% as dry or wet binders and as rate controlling agents. It is known from WO 2006/082099, that small amounts of anionic methacrylic acid and methyl methacrylate copolymers (Eudragit®) can be included into polyalkylene oxide matrices of tamper-resistant dosage forms without altering their mechanical properties. However, pharmaceutical dosage forms comprising larger amounts of anionic polymer(s) that nonetheless exhibit a sufficiently high breaking strength and impact resistance are not known so far.

T. Ozeki et al., International Journal of Pharmaceutics, 165 (1998) 239-244 disclose poly(ethylene oxide)-carboxyvinylpolymer solid dispersions prepared from water/ethanol mixture as a solvent. Similarly, T. Ozeki et al., Journal of Controlled Release, 63 (2000) 287-295 relates to controlled release from solid dispersion composed of poly (ethylene oxide)-Carbopol® interpolymer complex with various cross-linking degrees of Carbopol®. The polyethylene oxide employed in these studies had an average molecular weight of below 150,000 g/mol only. However, these solid dispersions are prepared by means of wet granulation using water/ethanol as the granulating fluid, and are thus not suitable for the avoidance of drug abuse.

US 2008/069871 discloses oral dosage forms of therapeutic agents that are resistant to abuse and methods of their formulation. In particular, oral dosage forms that are resistant to dissolution in aqueous solutions of ethanol are described.

EP 1 502 592 relates to controlled release oxycodone dosage form for oral administration to human patients, comprising an oxycodone salt; a matrix incorporating said oxycodone salt; the matrix comprising at least one acrylic resin; wherein said dosage form has an in vitro dissolution rate when measured by the USP Paddle Method at 100 rpm in 900 ml aqueous buffer (pH between 1.6 and 7.2) at 37 DEG C., between 12.5% and 42.5% (by weight) oxycodone salt released after 1 hour, between 25% and 56% (by weight) oxycodone salt released after 2 hours, between 45% and 75% (by weight) oxycodone salt released after 4 hours and between 55% and 85% (by weight) oxycodone salt released after 6 hours, the in vitro dissolution rate being independent of pH between 1.6 and 7.2.

US 2007/190142 discloses a dosage form and method for the delivery of drugs, particularly drugs of abuse, characterized by resistance to solvent extraction, tampering, crushing, or grinding, and providing an initial burst of release of drug followed by a prolonged period of controllable drug release.

US 2011/097404 relates to an oral dosage form comprising (i) an opioid agonist in releasable form and (ii) a sequestered opioid antagonist which is not released when the dosage form is administered orally intact.

WO 2010/140007 discloses a dosage form, particularly a tamper resistant dosage form, comprising: melt-extruded particulates comprising a drug; and a matrix; wherein said melt-extruded particulates are present as a discontinuous phase in said matrix.

US 2011/159100 relates to controlled release formulations and methods for preparing controlled release formulations for delivery of active drug substances. The formulations may be employed to produce pharmaceutical compositions, such as controlled release dosage forms, adjusted to a specific administration scheme.

WO 2012/028318 discloses a pharmaceutical dosage form exhibiting a breaking strength of at least 500 N, said dosage form containing—a pharmacologically active ingredient (A);—a physiologically acceptable polymer (B) obtainable by polymerization of a monomer composition comprising an ethylenically unsaturated monomer bearing an anionic functional group, in protonated form or a physiologically acceptable salt thereof;—a polyalkylene oxide (C) having a weight average molecular weight of at least 200,000 g/mol, wherein the content of the polyalkylene oxide (C) is at least 20 wt.-%, based on the total weight of the dosage form; wherein the pharmacologically active ingredient (A) is present in a controlled-release matrix comprising the polymer (B) and the polyalkylene oxide (C).

There is a demand for tamper resistant pharmaceutical dosage forms containing pharmacologically active compounds that have advantages compared to the tamper resistant pharmaceutical dosage forms of the prior art.

This object has been achieved by the subject-matter described hereinbelow.

A first aspect of the invention relates to a pharmaceutical dosage form having a breaking strength of at least 300 N and comprising a pharmacologically active compound,
an anionic polymer bearing carboxylic groups, wherein the content of the anionic polymer is ≥20 wt.-%, based on the total weight of the pharmaceutical dosage form, and
a nonionic surfactant.

It has been surprisingly found that tamper-resistant pharmaceutical dosage forms having a high breaking strength and impact resistance can be prepared by using an anionic polymer and optionally a nonionic surfactant, and that the presence of high molecular weight polyalkylene oxide is not required. Furthermore, it has been surprisingly found that liquid extraction of the pharmacologically active compound and subsequent administration of the thus obtained liquid by the non-prescribed, parenteral route can be substantially impeded by incorporating an effective amount of anionic polymer and optionally nonionic surfactant into the pharmaceutical dosage forms. It has further been found that these ingredients can have a stabilizing effect on the pharmaceutical ingredient contained in the dosage form.

BRIEF DESCRIPTION OF THE DRAWINGS

The invention will now be described in greater detail with reference to the drawings, wherein:

FIGS. 1-A, 1-B, 1-C, 1-D and 1-E, respectively, show the corresponding force-displacement diagrams of examples I-1, I-2, I-3, I-4 and C.

The pharmaceutical dosage form according to the invention comprises a pharmaceutically active compound, preferably a pharmacologically active compound having psychotropic activity, more preferably an opioid. Preferably, the pharmacologically active compound is selected from the group consisting of opiates, opioids, stimulants, tranquilizers, and other narcotics.

For the purpose of the specification, the term pharmacologically active compound also includes the free base and the physiologically acceptable salts thereof.

According to the ATC index, opioids are divided into natural opium alkaloids, phenylpiperidine derivatives, diphenylpropylamine derivatives, benzomorphan derivatives, oripavine derivatives, morphinan derivatives and others. Examples of natural opium alkaloids are morphine, opium, hydromorphone, nicomorphine, oxycodone, dihydrocodeine, diamorphine, papaveretum, and codeine. Further pharmacologically active compounds are, for example, ethylmorphine, hydrocodone, oxymorphone, and the physiologically acceptable derivatives thereof or compounds, preferably the salts and solvates thereof, preferably the hydrochlorides thereof, physiologically acceptable enantiomers, stereoisomers, diastereomers and racemates and the physiologically acceptable derivatives thereof, preferably ethers, esters or amides.

The following opiates, opioids, tranquillizers or other narcotics are substances with a psychotropic action, i.e. have a potential of abuse, and hence are preferably contained in the pharmaceutical dosage form according to the invention: alfentanil, allobarbital, allylprodine, alphaprodine, alprazolam, amfepramone, amphetamine, amphetaminil, amobarbital, anileridine, apocodeine, axomadol, barbital, bemidone, benzylmorphine, bezitramide, bromazepam, brotizolam, buprenorphine, butobarbital, butorphanol, camazepam, carfentanil, cathine/D-norpseudoephedrine, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dextromoramide, dextropropoxyphene, dezocine, diampromide, diamorphone, diazepam, dihydrocodeine, dihydromorphine, dihydromorphone, dimenoxadol, dimephetamol, dimethylthiambutene, dioxaphetylbutyrate, dipipanone, dronabinol, eptazocine, estazolam, ethoheptazine, ethylmethylthiambutene, ethyl loflazepate, ethylmorphine, etonitazene, etorphine, faxeladol, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethylmorphinan, ketazolam, ketobemidone, levacetylmethadol (LAAM), levomethadone, levorphanol, levophenacylmorphane, levoxemacin, lisdexamfetamine dimesylate, lofentanil, loprazolam, lorazepam, lormetazepam, mazindol, medazepam, mefenorex, meperidine, meprobamate, metapon, meptazinol, metazocine, methylmorphine, metamphetamine, methadone, methaqualone, 3-methylfentanyl, 4-methylfentanyl, methylphenidate, methylphenobarbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxycodone, oxymorphone, *Papaver somniferum*, papaveretum, pernoline, pentazocine, pentobarbital, pethidine, phenadoxone, phenomorphane, phenazocine, phenoperidine, piminodine, pholcodeine, phenmetrazine, phenobarbital, phentermine, pinazepam, pipradrol, piritramide, prazepam, profadol, proheptazine, promedol, properidine, propoxyphene, remifentanil, secbutabarbital, secobarbital, sufentanil, tapentadol, temazepam, tetrazepam, tilidine (cis and trans), tramadol, triazolam, vinylbital, N-(1-methyl-2-piperidinoethyl)-N-(2-pyridyl)propionamide, (1R,2R)-3-(3-dimethylamino-1-ethyl-2-methyl-propyl)phenol, (1R,2R,4S)-2-(dimethylamino)methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-di methylamino-1-ethyl-2-methyl-propyl)phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclohexyl)phenyl 2-(6-methoxy-naphthalen-2-yl)propionate, 3-(2-dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl)propionate, (RR—SS)-2-acetoxy-4-trifluoro-methyl-benzoic acid 3-(2-dimethylaminomethyl-1-hydroxy-cyclohexyl)-phenyl ester, (RR—SS)-2-hydroxy- 4-trifluoromethyl-benzoic acid 3-(2-dimethylaminomethyl-1-hydroxy-cyclohexyl)-phenyl ester, (RR—SS)-4-chloro-2-hydroxy-benzoic acid 3-(2-dimethylaminomethyl-1-hydroxy-cyclohexyl)-phenyl ester, (RR—SS)-2-hydroxy-4-methyl-benzoic acid 3-(2-dimethylaminomethyl-1-hydroxy-cyclohexyl)-phenyl ester, (RR—SS)-2-hydroxy-4-methoxy-benzoic acid 3-(2-dimethylaminomethyl-1-hydroxy-cyclohexyl)-phenyl ester, (RR—SS)-2-hydroxy-5-nitro-benzoic acid 3-(2-dimethylaminomethyl-1-hydroxy-cyclohexyl)-phenyl ester, (RR—SS)-2',4'-difluoro-3-hydroxy-biphenyl-4-carboxylic acid 3-(2-dimethylaminomethyl-1-hydroxy-cyclohexyl)-phenyl ester, and corresponding stereoisomers, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the acid or base addition salts thereof and solvates, e.g. hydrochlorides.

In a preferred embodiment the pharmaceutical dosage form according to the invention contains an opioid selected from the group consisting of DPI-125, M6G (CE-04-410), ADL-5859, CR-665, NRP290 and sebacoyl dinalbuphine ester.

Particularly preferred pharmacologically active compounds include hydromorphone, oxymorphone, oxycodone, tapentadol, and the physiologically acceptable salts thereof. In a preferred embodiment the pharmaceutical dosage form according to the invention contains one pharmacologically active compound or more pharmacologically active compounds selected from the group consisting of oxymorphone, hydromorphone and morphine. In another preferred embodiment, the pharmacologically active compound is selected from the group consisting of tapentadol, faxeladol and axomadol.

In still another preferred embodiment, the pharmacologically active compound is selected from the group consisting of 1,1-(3-dimethylamino-3-phenylpentamethylene)-6-fluoro-1,3,4,9-tetrahydropyrano[3,4-b]indole, particularly its hemicitrate; 1,1-[3-dimethylamino-3-(2-thienyl)-pentamethylene]-1,3,4,9-tetrahydropyrano[3,4-b]indole, particularly its citrate; and 1,1-[3-dimethylamino-3-(2-thienyhpentamethylene]-1,3,4,9-tetrahydropyrano[3,4-b]-6-fluoroindole, particularly its hemicitrate. These compounds are known from, e.g., WO 2004/043967, WO 2005/066183.

The pharmacologically active compound may be present in form of a physiologically acceptable salt, e.g. physiologically acceptable acid addition salt.

Physiologically acceptable acid addition salts comprise the acid addition salt forms which can conveniently be obtained by treating the base form of the active ingredient with appropriate organic and inorganic acids. Active ingredients containing an acidic proton may be converted into their non-toxic metal or amine addition salt forms by treatment with appropriate organic and inorganic bases. The term addition salt also comprises the hydrates and solvent addition forms which the active ingredients are able to form. Examples of such forms are e.g. hydrates, alcoholates and the like.

The content of the pharmacologically active compound in the pharmaceutical dosage form is not limited. The pharmacologically active compound is present in the pharmaceutical dosage form in a therapeutically effective amount. The amount that constitutes a therapeutically effective amount varies according to the active ingredients being used, the condition being treated, the severity of said condition, the patient being treated, and whether the pharmaceutical dosage form is designed for an immediate or retarded release.

Preferably, the content of the pharmacologically active compound is within the range of from 0.01 to 80 wt.-%, more preferably 0.1 to 50 wt.-%, still more preferably 1 to 25 wt.-%, based on the total weight of the pharmaceutical dosage form. In a preferred embodiment, the content of pharmacologically active compound is within the range of from 7±6 wt.-%, more preferably 7±5 wt.-%, still more preferably 5±4 wt.-%, 7±4 wt.-% or 9±4 wt.-%, most preferably 5±3 wt.-%, 7±3 wt.-% or 9±3 wt.-%, and in particular 5±2 wt.-%, 7±2 wt.-% or 9±2 wt.-%, based on the total weight of the pharmaceutical dosage form. In another preferred embodiment, the content of pharmacologically active compound is within the range of from 11±10 wt.-%, more preferably 11±9 wt.-%, still more preferably 9±6 wt.-%, 11±6 wt.-%, 13±6 wt.-% or 15±6 wt.-%, most preferably 11±4 wt.-%, 13±4 wt.-% or 15±4 wt.-%, and in particular 11±2 wt.-%, 13±2 wt.-% or 15±2 wt.-%, based on the total weight of the pharmaceutical dosage form. In a further preferred embodiment, the content of pharmacologically active compound is within the range of from 20±6 wt.-%, more preferably 20±5 wt.-%, still more preferably 20±4 wt.-%, most preferably 20±3 wt.-%, and in particular 20±2 wt.-%, based on the total weight of the pharmaceutical dosage form.

Preferably, the total amount of the pharmacologically active compound that is contained in the pharmaceutical dosage form is within the range of from 0.01 to 200 mg, more preferably 0.1 to 190 mg, still more preferably 1.0 to 180 mg, yet more preferably 1.5 to 160 mg, most preferably 2.0 to 100 mg and in particular 2.5 to 80 mg.

In a preferred embodiment, the pharmacologically active compound is contained in the pharmaceutical dosage form in an amount of 7.5±5 mg, 10±5 mg, 20±5 mg, 30±5 mg, 40±5 mg, 50±5 mg, 60±5 mg, 70±5 mg, 80±5 mg, 90±5 mg, 100±5 mg, 110±5 mg, 120±5 mg, 130±5, 140±5 mg, 150±5 mg, or 160±5 mg. In another preferred embodiment, the pharmacologically active compound is contained in the pharmaceutical dosage form in an amount of 5±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, or 160±2.5 mg.

In a preferred embodiment, the pharmacologically active compound is oxymorphone, preferably its hydrochloride salt, and the pharmaceutical dosage form is adapted for administration twice daily. In this embodiment, the pharmacologically active compound is preferably contained in the pharmaceutical dosage form in an amount of from 5 to 40 mg. In another particularly preferred embodiment, the pharmacologically active compound is oxymorphone, preferably its hydrochloride salt, and the pharmaceutical dosage form is adapted for administration once daily. In this embodiment, the pharmacologically active compound is preferably contained in the pharmaceutical dosage form in an amount of from 10 to 80 mg.

In another preferred embodiment, the pharmacologically active compound is oxycodone, preferably its hydrochloride salt, and the pharmaceutical dosage form is adapted for administration twice daily. In this embodiment, the pharmacologically active compound is preferably contained in the pharmaceutical dosage form in an amount of from 5 to 80 mg, preferably 5 mg, 10 mg, 20 mg or 40 mg. In another particularly preferred embodiment, the pharmacologically active compound is oxycodone, preferably its hydrochloride salt, and the pharmaceutical dosage form is adapted for administration once daily. In this embodiment, the pharmacologically active compound is preferably contained in the pharmaceutical dosage form in an amount of from 10 to 320 mg.

In still another particularly preferred embodiment, the pharmacologically active compound is hydromorphone, preferably its hydrochloride, and the pharmaceutical dosage form is adapted for administration twice daily. In this embodiment, the pharmacologically active compound is preferably contained in the pharmaceutical dosage form in an amount of from 2 to 52 mg. In another particularly preferred embodiment, the pharmacologically active compound is hydromorphone, preferably its hydrochloride salt, and the pharmaceutical dosage form is adapted for administration once daily. In this embodiment, the pharmacologically active compound is preferably contained in the pharmaceutical dosage form in an amount of from 4 to 104 mg.

In yet another particularly preferred embodiment, the pharmacologically active compound is tapentadol, preferably its hydrochloride, and the pharmaceutical dosage form is adapted for administration twice daily. In this embodiment, the pharmacologically active compound is preferably contained in the pharmaceutical dosage form in an amount of from 25 to 250 mg. In another particularly preferred embodiment, the pharmacologically active compound is tapentadol, preferably its hydrochloride salt, and the pharmaceutical dosage form is adapted for administration once daily. In this embodiment, the pharmacologically active compound is preferably contained in the pharmaceutical dosage form in an amount of from 50 to 600 mg.

The pharmaceutical dosage form according to the invention further comprises an anionic polymer bearing carboxylic groups, wherein the content of the anionic polymer is ≥20 wt.-%, based on the total weight of the pharmaceutical dosage form.

Preferably, the anionic polymer comprises anionic functional groups selected from carboxyl groups, sulfonyl groups, sulfate groups, and phosphoryl groups.

Preferably, the anionic polymer is derived from an ethylenically unsaturated monomer selected from (alk)acrylic acids, (alk)acrylic anhydrides, alkyl (alk)acrylates, or a combination thereof; i.e. the anionic polymer is preferably obtainable by polymerization of a monomer composition comprising one or more of said ethylenically unsaturated monomers and optionally at least partial hydrolysis of the optionally present acid anhydride and/or carboxylic ester groups.

Preferably, the anionic polymer is obtainable by polymerization of a monomer composition comprising an ethylenically unsaturated monomer selected from ethylenically unsaturated carboxylic acids, ethylenically unsaturated carboxylic acid anhydrides, ethylenically unsaturated sulfonic acids, and mixtures thereof.

Preferred ethylenically unsaturated carboxylic acid and ethylenically unsaturated carboxylic acid anhydride monomers include the acrylic acids typified by acrylic acid itself, methacrylic acid, ethacrylic acid, alpha-chloracrylic acid, alpha-cyano acrylic acid, beta-methyl-acrylic acid (crotonic acid), alpha-phenyl acrylic acid, beta-acryloxy propionic acid, sorbic acid, alpha-chloro sorbic acid, angelic acid, cinnamic acid, p-chloro cinnamic acid, beta-styryl acrylic acid (1-carboxy-4-phenyl butadiene-1,3), itaconic acid, citraconic acid, mesaconic acid, glutaconic acid, aconitic acid, maleic acid, fumaric acid, tricarboxy ethylene and maleic acid anhydride.

Preferred ethylenically unsaturated sulfonic acids include aliphatic or aromatic vinyl sulfonic acids such as vinylsulfonic acid, allyl sulfonic acid, vinyltoluenesulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-acryloxy propyl sulfonic acid, 2-hydroxy-3-methacryloxy propyl sulfonic acid and 2-acrylamido-2-methyl propane sulfonic acid.

Preferably, the monomer composition comprises acrylic acid, methacrylic acid, and/or 2-acrylamido-2-methyl propane sulfonic acid. Acrylic acid is especially preferred.

For the purpose of the specification, the wording "obtainable by polymerization of a monomer composition" does not necessarily require that the anionic polymer has been obtained from such a monomer composition indeed. In other words, the anionic polymer is a polymer comprising at least one repeating unit which results from polymerization of an ethylenically unsaturated monomer bearing an anionic functional group, in protonated form or a physiologically acceptable salt thereof.

The anionic polymer may be linear or branched or cross-linked.

Preferably, the anionic polymer is hydrophilic, more preferably water-soluble or water-swellable.

The anionic polymer may be a homopolymer or a copolymer. When the anionic polymer is a homopolymer, it comprises a single type of repeating unit, i.e. it is the polymerization product of a monomer composition comprising a single type of monomer. When the anionic polymer is a copolymer, it may comprise two, three or more different repeating units, i.e. may be the polymerization product of a monomer composition comprising two, three or more different monomers.

In a preferred embodiment, the anionic polymer is a copolymer, comprising from about 50 mol-% to 99.999 mol-%, and more preferably from about 75 mol-% to 99.99 mol-% repeating units bearing anionic functional groups, preferably acid groups, more preferably carboxylic groups.

Preferably, the anionic polymer has an average equivalent weight of 76±50 g/mol, more preferably of 76±30 g/mol, still more preferably of 76±20 g/mol and most preferably of 76±10 g/mol per carboxyl group.

In a preferred embodiment, the monomer composition from which the anionic polymer is derivable further comprises a cross-linking agent, i.e. in this embodiment the anionic polymer is cross-linked.

Suitable cross-linking agents include
- compounds having at least two polymerizable double bonds, e.g. ethylenically unsaturated functional groups;
- compounds having at least one polymerizable double bond, e.g. an ethylenically unsaturated functional group, and at least one functional group that is capable of reacting with another functional group of one or more of the repeating units of the anionic polymer;
- compounds having at least two functional groups that are capable of reacting with other functional groups of one or more of the repeating units of the anionic polymer; and
- polyvalent metal compounds which can form ionic cross-linkages, e.g. through the anionic functional groups.

Cross-linking agents having at least two polymerizable double bonds, preferably allyl groups, are particularly preferred.

Cross-linking agents having at least two polymerizable double bonds include (i) di- or polyvinyl compounds such as divinylbenzene and divinyltoluene; (ii) di- or poly-esters of unsaturated mono- or poly-carboxylic acids with polyols including, for example, di- or triacrylic acid esters of polyols such as ethylene glycol, trimethylol propane, glycerine, or polyoxyethylene glycols; (iii) bisacrylamides such as N,N-methylenebisacrylamide; (iv) carbamyl esters that can be obtained by reacting polyisocyanates with hydroxyl group-containing monomers; (v) di- or poly-allyl ethers of polyols; (vi) di- or poly-allyl esters of polycarboxylic acids such as diallyl phthalate, diallyl adipate, and the like; (vii) esters of unsaturated mono- or poly-carboxylic acids with mono-allyl esters of polyols such as acrylic acid ester of polyethylene glycol monoallyl ether; and (viii) di- or triallyl amine.

In a preferred embodiment, divinyl glycol (1,5-hexadiene-3,4-diol) is contained as cross-linking agent, whereas allyl or vinyl derivatives of polyols, such as allylsucrose or allyl pentaerythritol, are less preferred. This embodiment is preferably realized by polyacrylic acid polymers of polycarbophil type according to USP.

In another preferred embodiment, allyl derivatives of polyols, such as allylsucrose or allyl pentaerythritol, are contained as cross-linking agent, whereas divinyl glycol (1,5-hexadiene-3,4-diol) is less preferred. This embodiment is preferably realized by polyacrylic acid polymers of carbomer type according to USP or Ph. Eur.

Cross-linking agents having at least one polymerizable double bond and at least one functional group capable of reacting with other functional groups of one or more of the repeating units of the anionic polymer include N-methylol acrylamide, glycidyl acrylate, and the like.

Suitable cross-linking agents having at least two functional groups capable of reacting with other functional groups of one or more of the repeating units of the anionic polymer include glyoxal; polyols such as ethylene glycol; polyamines such as alkylene diamines (e.g., ethylene diamine), polyalkylene polyamines, polyepoxides, di- or polyglycidyl ethers and the like.

Suitable polyvalent metal cross-linking agents which can form ionic cross-linkages include oxides, hydroxides and weak acid salts (e.g., carbonate, acetate and the like) of alkaline earth metals (e.g., calcium magnesium) and zinc, including, for example, calcium oxide and zinc diacetate.

Of all of these types of cross-linking agents, the most preferred for use herein are diol derivatives and polyol derivatives, more specifically those selected from the group consisting of allyl sucrose, allyl pentaerythritol, divinyl glycol, divinyl polyethylene glycol and (meth)acrylic acid esters of diols.

In a preferred embodiment, the monomer composition from which the anionic polymer is derivable comprises the cross-linking agent in an amount of at most 1.0 mol-%, more preferably at most 0.1 mol-%, even more preferably at most about 0.01 mol-%, and most preferably at most 0.005 mol-% based on all monomers forming the anionic polymer.

In a preferred embodiment, the anionic polymer is a homopolymer of acrylic acid, optionally cross-linked, preferably with allyl sucrose or allyl pentaerythritol, in particular with allyl pentaerythritol. In another preferred embodiment, the anionic polymer is a copolymer of acrylic acid and $C_{10}$-$C_{30}$-alkyl acrylate, optionally cross-linked, preferably with allyl pentaerythritol. In another preferred embodiment, the anionic polymer is a so-called interpolymer, namely a homopolymer of acrylic acid, optionally cross-linked, preferably with allyl sucrose or allyl pentaerythritol; or a copolymer of acrylic acid and $C_{10}$-$C_{30}$-alkyl acrylate, optionally cross-linked, preferably with allyl pentaerythritol; which contain a block copolymer of polyethylene glycol and a long chain alkyl acid, preferably a $C_8$-$C_{30}$-alkyl acid. Polymers of this type are commercially available, e.g. under the trademark Carbopol®.

When the anionic polymer is an interpolymer, it preferably exhibits a viscosity within the range of from 2,000 to 60,000 mPa·s, more preferably 2,500 to 40,000 mPa·s, still more preferably 3,000 to 15,000 mPa·s, measured by means of a Brookfield viscosimeter (RVF, 20 rpm, spindle 5) in a 0.5 wt.-% aqueous solution at pH 7.5 and 25° C.

Preferably, at least some of the anionic functional groups contained in the anionic polymer are present in neutralized form, i.e. they are not present in their protonated forms, but are salts with salt-forming cations instead. Suitable salt-forming cations include alkali metal, ammonium, substituted ammonium and amines. More preferably, at least some of the anionic functional groups, e.g. carboxylate and/or sulfonate anions, are salts of sodium or potassium cations.

This percentage of neutralized anionic functional groups, i.e. the percentage of anionic functional groups being present in neutralized form, based on the total amount of anionic functional groups, is referred to herein as the "degree of neutralization." In a preferred embodiment, the degree of neutralization is within the range of from 2.5±2.4%, more preferably 2.5±2.0%, still more preferably 2.5±1.5%, yet more preferably 2.5±1.0%, and most preferably 2.5±0.5%. In another preferred embodiment, the degree of neutralization is within the range of 35±30%, more preferably 35±25%, still more preferably 35±20%, yet more preferably 35±15%, most preferably 35±10%, and in particular 35±5%. In yet another preferred embodiment, the degree of neutralization is in the range of 65±30%, more preferably 65±25%, still more preferably 65±20%, yet more preferably 65±15%, most preferably 65±10%, and in particular 65±5%.

In a preferred embodiment, the anionic polymer has a weight average molecular weight ($M_W$) of at least 100,000 g/mol, preferably at least 200,000 g/mol or at least 400,000 g/mol, more preferably in the range of about 500,000 g/mol to about 5,000,000 g/mol, and most preferably in the range of about 600,000 g/mol to about 2,000,000 g/mol. Suitable methods to determine $M_W$ are known to a person skilled in the art. For instance, $M_W$ can be determined by gel permeation chromatography (GPC).

In a preferred embodiment, the $pK_A$ of the anionic polymer is 6.0±2.0, more preferably 6.0±1.5, even more preferably 6.0±1.0, and most preferably 6.0±0.5. In another preferred embodiment, the $pK_A$ of the anionic polymer is 7.0±2.0, more preferably 7.0±1.5, even more preferably 7.0±1.0, and most preferably 7.0±0.5. In still another preferred embodiment, the $pK_A$ of the anionic polymer is 8.0±2.0, more preferably 8.0±1.5, even more preferably 8.0±1.0, and most preferably 8.0±0.5.

In a preferred embodiment, the pH (in 1 wt % aqueous dispersion) of the anionic polymer is 3.0±3.0, more preferably 3.0±2.0, even more preferably 3.0±1.5, and most preferably 3.0±1.0.

In another preferred embodiment, the pH (in 1 wt % aqueous dispersion) of the anionic polymer is 6.0±3.0, more preferably 6.0±2.0, even more preferably 6.0±1.5, and most preferably 6.0±1.0.

The anionic polymer preferably exhibits a viscosity of 2,000 to 100,000 mPa s (cp), more preferably 3,000 to 80,000 mPa s, still more preferably 4,000 to 60,000 mPa s, measured by means of a Brookfield viscometer (RVF, 20 rpm, spindle 5) in a 0.5 wt.-% aqueous solution at pH 7.5 and 25° C.

In a preferred embodiment, the anionic polymer exhibits a viscosity of at most 30,000 mPa s (cp), preferably at most 28,000 mPa s, more preferably at most 25,000 mPa s, still more preferably at most 20,000 mPa s or at most 15,000 mPa s, measured by means of a Brookfield viscometer (RVF, 20 rpm, spindle 5) in a 0.5 wt.-% aqueous solution at pH 7.5 and 25° C.

Preferably, the overall content of anionic polymer is within the range of from 20 to 95 wt.-%, more preferably 20 to 90 wt.-%, most preferably 25 to 75 wt.-%, and in particular 25 to 50 wt.-%, based on the total weight of the pharmaceutical dosage form.

In a preferred embodiment, the overall content of anionic polymer is at least 21 wt.-%, more preferably at least 22 wt.-%, still more preferably at least 23 wt.-% or at least 24 wt.-%, most preferably at least 26 wt.-% or 28 wt.-%, and in particular at least 30 wt.-% or at least 32 wt.-%, based on the total weight of the pharmaceutical dosage form.

In a preferred embodiment, the overall content of anionic polymer is within the range of 20 to 50 wt.-%, more preferably 20 to 45 wt.-%, still more preferably 20 to 40 wt.-%, most preferably 20 to 35 wt.-%, and in particular preferably 20 to 30 wt.-%. In another preferred embodiment, the overall content of anionic polymer is within the range of 20 to 50 wt.-%, more preferably 20 to 45 wt.-%, still more preferably 20 to 40 wt.-%, most preferably 20 to 35 or 25 to 40 wt.-%, and in particular preferably 25 to 35 wt.-%. In still another preferred embodiment, the overall content of anionic polymer is within the range of 35±15 wt.-%, more preferably 35±10 wt.-%, and most preferably 35±5 wt.-%. In yet another preferred embodiment, the overall content of anionic polymer is within the range of 40±20 wt.-%, more preferably 40±15 wt.-%, most preferably 40±10 wt.-%, and in particular 40±5 wt.-%. In a further preferred embodiment, the overall content of anionic polymer is within the range of 50±20 wt.-%, more preferably 50±15 wt.-%, most preferably 50±10 wt.-%, and in particular 50±5 wt.-%.

Preferably, the relative weight ratio of the anionic polymer to the pharmacologically active compound is at least 0.5:1, more preferably at least 1:1, at least 2:1, at least 3:1, at least 4:1, at least 5:1, at least 6:1, at least 7:1, at least 8:1 or at least 9:1. In a preferred embodiment, the relative weight ratio of the anionic polymer to the pharmacologically active compound is within the range of from 5:1 to 1:1, more preferably 4:1 to 2:1.

In a preferred embodiment, the relative weight ratio of the pharmacologically active ingredient to the anionic polymer is at most 4.5:1, more preferably at most 4.0:1, still more preferably at most 3.5:1, yet more preferably at most 3.0:1, even more preferably at most 2.5:1, most preferably at most 2.0:1 and in particular at most 1.5:1. In a particularly preferred embodiment, the relative weight ratio of the pharmacologically active ingredient to the anionic polymer is at most 1.4:1, more preferably at most 1.3:1, still more preferably at most 1.2:1, yet more preferably at most 1.1:1, even more preferably at most 1.0:1, most preferably at most 0.9:1 and in particular at most 0.8:1.

Preferably, the relative weight ratio of the pharmacologically active ingredient to the sum of anionic polymer and nonionic surfactant is at most 3.0:1, more preferably at most 2.8:1, still more preferably at most 2.6:1, yet more preferably at most 2.4:1, even more preferably at most 2.2:1, most preferably at most 2.0:1 and in particular at most 1.8:1. In a particularly preferred embodiment, the relative weight ratio of the pharmacologically active ingredient to the sum of anionic polymer and nonionic surfactant is at most 1.6:1, more preferably at most 1.4:1, still more preferably at most 1.2:1, yet more preferably at most 1.0:1, even more preferably at most 0.8:1, most preferably at most 0.6:1 and in particular at most 0.4:1.

In a preferred embodiment, the anionic polymer is homogeneously distributed in the pharmaceutical dosage form according to the invention. Preferably, the anionic polymer forms a matrix in which the pharmacologically active compound is embedded. In a particularly preferred embodiment, the pharmacologically active compound and the anionic polymer are intimately homogeneously distributed in the pharmaceutical dosage form so that the pharmaceutical dosage form does not contain any segments where either pharmacologically active compound is present in the absence of anionic polymer, or where anionic polymer is present in the absence of pharmacologically active compound.

When the pharmaceutical dosage form is film coated, the anionic polymer is preferably homogeneously distributed in the core of the pharmaceutical dosage form, i.e. the film coating preferably does not contain anionic polymer. Nonetheless, the film coating as such may of course contain one or more polymers, which however, preferably differ from the anionic polymer contained in the core.

The pharmaceutical dosage form according to the invention may either contain only one, or two or more anionic polymers of various types.

The anionic polymer may be combined with one or more different polymers selected from the group consisting of polyalkylene oxide, preferably polymethylene oxide, polyethylene oxide, polypropylene oxide; polyethylene, polypropylene, polyvinyl chloride, polycarbonate, polystyrene, polyvinylpyrrolidone, poly(hydroxy fatty acids), such as for example poly(3-hydroxybutyrate-co-3-hydroxyvalerate) (Biopol®), poly(hydroxyvaleric acid); polycaprolactone, polyvinyl alcohol, polyesteramide, polyethylene succinate, polylactone, polyglycolide, polyurethane, polyamide, polylactide, polyacetal (for example polysaccharides optionally with modified side chains), polylactide/glycolide, polylactone, polyglycolide, polyorthoester, polyanhydride, block polymers of polyethylene glycol and polybutylene terephthalate (Polyactive), polyanhydride (Polifeprosan), copolymers thereof, block-copolymers thereof, or with mixtures of at least two of the stated polymers.

In a preferred embodiment, the pharmaceutical dosage form according to the invention does not contain any polyalkylene oxide having an average molecular weight of at least 200,000 g/mol, preferably at least 150,000 g/mol, more preferably at least 100,000 g/mol, still more preferably at least 75,000 g/mol, yet more preferably at least 50,000 g/mol, and most preferably at least 25,000 g/mol.

If, however, the anionic polymer is combined with one or more polymers selected from the group consisting of polyalkylene oxides, preferably polymethylene oxide, polyethylene oxide and polypropylene oxide; the total content of polyalkylene oxide(s) having an average molecular weight of at least 200,000 g/mol is preferably 35 wt.-%, based on the total weight of the pharmaceutical dosage form.

In a preferred embodiment, the pharmaceutical dosage form according to the invention contains at least one polyalkylene oxide having an average molecular weight of at least 200,000 g/mol, preferably at least 150,000 g/mol, more preferably at least 100,000 g/mol, still more preferably at least 75,000 g/mol, yet more preferably at least 50,000 g/mol, and most preferably at least 25,000 g/mol. In this embodiment, the total content of polyalkylene oxide(s) contained in the dosage form and having said minimum average molecular weight is preferably ≤35 wt.-%, more preferably ≤30 wt.-%, still more preferably ≤25 wt.-%, yet more preferably ≤20 wt.-%, even more preferably ≤15 wt.-%, most preferably ≤10 wt.-%, and in particular <5 wt.-%, based on the total weight of the pharmaceutical dosage form.

For the purpose of the specification, a polyalkylene oxide may comprise a single polyalkylene oxide having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

For the purpose of the specification, a polyalkylene glycol has a molecular weight of up to 20,000 g/mol whereas a polyalkylene oxide has a molecular weight of more than 20,000 g/mol. Polyalkylene glycols, if any, are preferably not taken into consideration when determining the weight average molecular weight of polyalkylene oxide.

In a preferred embodiment according to the invention, the anionic polymer is combined with at least one further polymer, preferably selected from the group consisting of polyethylene, polypropylene, polyvinyl chloride, polycarbonate, polystyrene, poly(hydroxy fatty acids), polycaprolactone, polyvinyl alcohol, polyesteramide, polyethylene succinate, polylactone, polyglycolide, polyurethane, polyvinylpyrrolidone, polyamide, polylactide, poly-lactide/glycolide, polylactone, polyglycolide, polyorthoester, polyanhydride, block polymers of polyethylene glycol and polybutylene terephthalate, polyanhydride, polyacetal, cellulose esters, cellulose ethers and copolymers thereof. Cellulose esters and cellulose ethers are particularly preferred, e.g. methylcellulose, ethylcellulose, hydroxymethylcellulose, hydroxyethylcellulose, hydroxypropylcellulose hydroxypropylmethylcellulose, carboxymethylcellulose, and the like.

In a preferred embodiment, said further polymer is neither an anionic polymer nor a polyalkylene glycol or polyalkylene oxide. Nonetheless, the pharmaceutical dosage form may contain polyalkylene glycol, e.g. as plasticizer, or a polyalkylene oxide, but then, the pharmaceutical dosage form preferably is an at least ternary mixture of polymers: anionic polymer+further polymer+plasticizer or anionic polymer+further polymer+polyalkylene oxide. A ternary mixture of anionic polymer+further polymer+plasticizer is particularly preferred.

In a particularly preferred embodiment, said further polymer is a hydrophilic cellulose ester or cellulose ether, preferably hydroxypropylmethylcellulose (HPMC), hydroxypropylcellulose (HPC) or hydroxyethylcellulose (HEC), preferably having an average viscosity (preferably measured by capillary viscosimetry or rotational viscosimetry) of 1,000 to 150,000 mPas, more preferably 3,000 to 150,000. In a preferred embodiment, the average viscosity is within the range of 110,000±50,000 mPas, more preferably 110,000±40,000 mPas, still more preferably 110,000±30,000 mPas, most preferably 110,000±20,000 mPas, and in particular 100,000±10,000 mPas.

In a preferred embodiment, the further polymer is a cellulose ester or cellulose ether, preferably HPMC, having a content within the range of 10±8 wt.-%, more preferably 10±6 wt.-%, still more preferably 10±5 wt.-%, yet more preferably 10±4 wt.-%, most preferably 10±3 wt.-%, and in particular 10±2 wt.-%, based on the total weight of the pharmaceutical dosage form.

In another preferred embodiment, the further polymer is a cellulose ester or cellulose ether, preferably HPMC, having a content within the range of 15±8 wt.-%, more preferably 15±6 wt.-%, still more preferably 15±5 wt.-%, yet more preferably 15±4 wt.-%, most preferably 15±3 wt.-%, and in particular 15±2 wt.-%, based on the total weight of the pharmaceutical dosage form.

Preferably, the relative weight ratio of the sum of anionic polymer and nonionic surfactant to further polymer is within the range of from 1:1 to 10:1, more preferably from 2:1 to 8:1.

In a preferred embodiment, the relative weight ratio of the sum of anionic polymer and nonionic surfactant to further polymer is at least 2.0:1, more preferably at least 2.5:1, still more preferably at least 3.0:1, yet more preferably at least 3.5:1, even more preferably at least 4.0:1, most preferably at least 4.5:1, and in particular at least 5.0:1.

The pharmaceutical dosage form according to the invention further comprises a nonionic surfactant.

In a preferred embodiment, the nonionic surfactant has a hydrophilic-lipophilic balance (HLB) of at least 10, preferably at least 12, more preferably at least 14, still more preferably at least 16, yet more preferably at least 18, even more preferably at least 20, most preferably at least 22, and in particular at least or more than 24.

The hydrophilic-lipophilic balance (HLB value) can be estimated according to Griffin's method (Griffin, W. C.; J. Soc. Cosmet. Chem. 1 (1949) 311).

Preferably, however, the HLB value is calculated by the incremental method, i.e. by adding the individual HLB increments of all hydrophobic and hydrophilic groups present in the molecule. HLB increments of many hydrophobic and hydrophilic groups can be found, e.g., in Fiedler, H. P., Encyclopedia of Excipients, Editio Cantor Verlag, Aulendorf, 6th Edition, 2007. The HLB value can further be determined experimentally, e.g. by partition chromatography or HPLC.

In another preferred embodiment, the nonionic surfactant exhibits a surface tension in 0.1% aqueous solution at 25° C. of at least 35 dynes/cm, more preferably at least 40 dynes/cm, still more preferably at least 43 dynes/cm, yet more preferably at least 45 dynes/cm, even more preferably at least 47 dynes/cm, in particular at least 50 dynes/cm.

In another preferred embodiment, the nonionic surfactant exhibits a viscosity of at most 4000 mPa·s, more preferably at most 3500 mPa·s, still more preferably at most 3000 mPa·s, yet more preferably at most 2500 mPa·s, even more preferably at most 2000 mPa·s, most preferably at most 1500 mPa·s, and in particular at most 1000 mPa·s, measured at 70° C. using a model LVF or LVT Brookfield viscosimeter.

Suitable non-ionic surfactants include but are not limited to polyoxypropylene-polyoxyethylene block copolymers (e.g., poloxamers or poloxamines), preferably according to general formula (I-a)

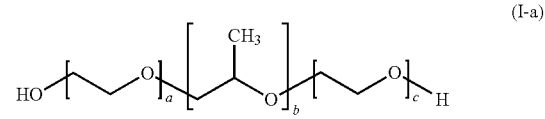

wherein a and c are each independently an integer of from 5 to 250, and b is an integer of from 10 to 100; preferably, a=c≠b; and/or a=c>b;

or according to general formula (I-b)

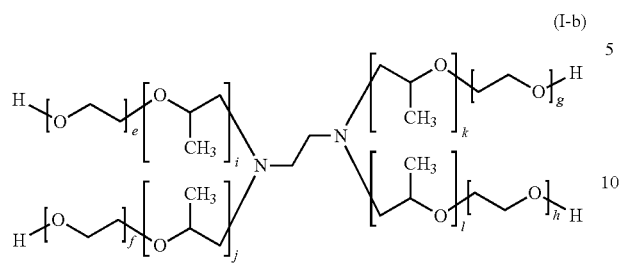

wherein e, f, g and h are each independently an integer of from 1 to 150, and i, j, k and l are each independently an integer of from 2 to 50; and preferably, the ratio (e+f+g+h)/(i+j+k+l) is an integer of from 0.015 to 30;

fatty alcohols that may be linear or branched, such as cetylalcohol, stearylalcohol, cetylstearyl alcohol, 2-octyldodecane-1-ol and 2-hexyldecane-1-ol;

sterols, such as cholesterole;

partial fatty acid esters of sorbitan such as sorbitanmonolaurate, sorbitanmonopalmitate, sorbitanmonostearate, sorbitantristearate, sorbitanmonooleate, sorbitansesquioleate and sorbitantrioleate;

partial fatty acid esters of polyoxyethylene sorbitan (polyoxyethylene-sorbitan-fatty acid esters), preferably a fatty acid monoester of polyoxyethylene sorbitan, a fatty acid diester of polyoxyethylene sorbitan, or a fatty acid triester of polyoxyethylene sorbitan; e.g. mono- and tri-lauryl, palmityl, stearyl and oleyl esters, such as the type known under the name "polysorbat" and commercially available under the trade name "Tween" including Tween® 20 [polyoxyethylene(20)sorbitan monolaurate], Tween® 21 [polyoxyethylene(4)sorbitan monolaurate], Tween® 40 [polyoxyethylene(20)sorbitan monopalmitate], Tween® 60 [polyoxyethylene(20) sorbitan monostearate], Tween® 65 [polyoxyethylene (20)sorbitan tristearate], Tween® 80 [polyoxyethylene (20)sorbitan monooleate], Tween 81 [polyoxyethylene (5)sorbitan monooleate], and Tween® 85 [polyoxyethylene(20)sorbitan trioleate]; preferably a fatty acid monoester of polyoxyethylenesorbitan according to general formula (I-c)

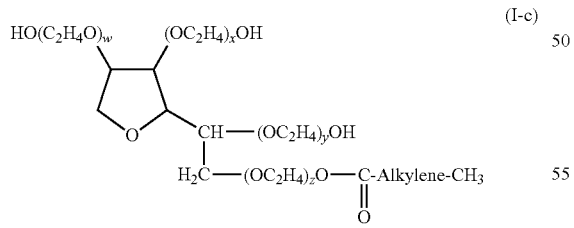

wherein (w+x+y+z) is within the range of from 15 to 100, preferably 16 to 80, more preferably 17 to 60, still more preferably 18 to 40 and most preferably 19 to 21; and alkylene is an optionally unsaturated alkylene group comprising 6 to 30 carbon atoms, more preferably 8 to 24 carbon atoms and most preferably 10 to 16 carbon atoms;

polyoxyethyleneglycerole fatty acid esters such as mixtures of mono-, di- and triesters of glycerol and di- and monoesters of macrogols having molecular weights within the range of from 200 to 4000 g/mol, e.g., macrogolglycerolcaprylocaprate, macrogolglycerollaurate, macrogolglycerolococoate, macrogolglycerollinoleate, macrogol-20-glycerolmonostearate, macrogol-6-glycerolcaprylocaprate, macrogolglycerololeate; macrogolglycerolstearate, macrogolglycerolhydroxystearate (e.g. Cremophor® RH 40), and macrogolglycerol-rizinoleate (e.g. Cremophor® EL);

polyoxyethylene fatty acid esters, the fatty acid preferably having from about 8 to about 18 carbon atoms, e.g. macrogololeate, macrogolstearate, macrogol-15-hydroxystearate, polyoxyethylene esters of 12-hydroxystearic acid, such as the type known and commercially available under the trade name "Solutol HS 15"; preferably according to general formula (I-d)

$$CH_3CH_2-(OCH_2CH_3)_n-O-CO-(CH_2)_m-CH_3 \quad (I-d)$$

wherein n is an integer of from 6 to 500, preferably 7 to 250, more preferably 8 to 100, still more preferably 9 to 75, yet more preferably 10 to 50, even more preferably 11 to 30, most preferably 12 to 25, and in particular 13 to 20; and wherein m is an integer of from 6 to 28; more preferably 6 to 26, still more preferably 8 to 24, yet more preferably 10 to 22, even more preferably 12 to 20, most preferably 14 to 18 and in particular 16;

polyoxyethylene fatty alcohol ethers, e.g. macrogolcetylstearylether, macrogollaurylether, macrogololeylether, macrogolstearylether;

fatty acid esters of saccharose; e.g. saccharose distearate, saccharose dioleate, saccharose dipalmitate, saccharose monostearate, saccharose monooleate, saccharose monopalmitate, saccharose monomyristate and saccharose monolaurate;

fatty acid esters of polyglycerol, e.g. polyglycerololeate;

polyoxyethylene esters of alpha-tocopheryl succinate, e.g. D-alpha-tocopheryl-PEG-1000-succinate (TPGS);

polyglycolyzed glycerides, such as the types known and commercially available under the trade names "Gelucire 44/14", "Gelucire 50/13 and "Labrasol";

reaction products of a natural or hydrogenated castor oil and ethylene oxide such as the various liquid surfactants known and commercially available under the trade name "Cremophor"; and partial fatty acid esters of multifunctional alcohols, such as glycerol fatty acid esters, e.g. mono- and tri-lauryl, palmityl, stearyl and oleyl esters, for example glycerol monostearate, glycerol monooleate, e.g. glyceryl monooleate 40, known and commercially available under the trade name "Peceol"; glycerole dibehenate, glycerole distearate, glycerole monolinoleate; ethyleneglycol monostearate, ethyleneglycol monopalmitostearate, pentaerythritol monostearate.

In a preferred embodiment, the nonionic surfactant is a thermosensitive polymer, in particular an inverse thermosensitive polymer, i.e. a polymer that is soluble in water at a comparatively low temperature, e.g. below or about 20° C., but gels (forms a gel) at higher temperatures, e.g. above 35° C.

For the purpose of the specification, an "inverse thermosensitive polymer" preferably is a polymer exhibiting an atypical dependency of viscosity from temperature; while aqueous dispersions of conventional polymers typically show decreased viscosities at increased temperatures, the viscosity of an aqueous dispersion of an inverse thermosensitive polymer according to the invention increases at increased temperatures, at least within a certain temperature range above ambient temperature. Preferably, the increase of viscosity that is induced by an increase of temperature leads to gel formation so that an aqueous dispersion of an inverse thermosensitive polymer according to the invention preferably forms a liquid solution at ambient temperature but a viscous gel at elevated temperature. Polymeric nonionic surfactants exhibiting these properties are known to the skilled artisan.

A skilled person recognizes that viscosity and gel strength may decrease again, once a certain temperature is exceeded. Thus, an aqueous dispersion of an inverse thermosensitive polymer according to the invention preferably has a viscosity maximum, which at a concentration of 25 wt.-%, relative to the total weight of the aqueous dispersion, is preferably within the range 45±20° C., or 55±20° C., or 65±20° C., or 75±20° C.

Thus, the nonionic surfactant according to the invention preferably forms a liquid solution in water at ambient temperature, and when the temperature is increased, the surfactant forms an aqueous gel, at least within a certain temperature range above ambient temperature.

Preferably, in pure water at a concentration of 25 wt.-% the nonionic surfactant forms an aqueous dispersion having a viscosity $\eta_1$ at a temperature $T_1$ of 20° C. and a viscosity $\eta_2$ at a temperature $T_2$ of more than 20° C. (i.e. $T_2 > T_1$), where $\eta_2 > \eta_1$. This does not necessarily mean that viscosity $\eta_2$ at any temperature $T_2$ above 20° C. must be greater than viscosity $\eta_1$ at 20° C. Instead, this means that there is at least one temperature $T_2$ above 20° C. at which viscosity $\eta_2$ of the aqueous dispersion is greater than viscosity $\eta_1$ at $T_1$ (=20° C.).

Preferably, an aqueous solution comprising at least 20 wt.-% or at least 25 wt.-% nonionic surfactant shows a thermoreversible behavior, i.e. the viscosity of the solution increases with increasing temperature and decreases with decreasing temperature, and repeated heating and cooling does not affect this property. Preferably, the aqueous solution exhibits a thermoreversible behavior with a maximum viscosity between 30 and 80° C.

In an especially preferred embodiment, the aqueous solution is a liquid at 20° C. and forms a semi-solid gel upon heating to a temperature of at most 80° C., more preferably 60° C., most preferably at most 45° C., and in particular at most 37° C.

Preferably, the sol-gel transition temperature, i.e. the temperature at which the phase transition occurs, is within the range of from 10° C. to 80° C., more preferably within the range of from 15° C. to 75° C., and most preferably within the range of from 20° C. to 60° C.

For example, various poloxamines and poloxamers, including poloxamer 407 and poloxamer 188, show inverse thermosensitivity.

Particularly preferably, the nonionic surfactant is a polyoxypropylene-polyoxyethylene block copolymer, preferably selected from poloxamers and poloxamines, in particular polyoxypropylene-polyoxyethylene block copolymer according to general formula (I-a) and polyoxypropylene-polyoxyethylene block copolymer according to general formula (I-b).

In a particular preferred embodiment, the nonionic surfactant is a polyoxypropylene-polyoxyethylene block copolymer according to general formula (I-a)

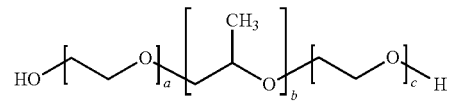

(I-a)

wherein a and c are each independently an integer of from 5 to 250, and b is an integer of from 10 to 100; and preferably, a=c≠b; and/or a=c>b. More preferably, a and c are each independently an integer of from 10 to 120, and b is an integer of from 15 to 75; and preferably, a=c>b. Polyoxypropylene-polyoxyethylene block copolymers of this type are also known as poloxamers and are commercially available under the trade name Pluronics.

In a preferred embodiment, a, b and c are each independently an integer as specified as preferred embodiments $N^1$ to $N^{32}$ in the table here below:

| | a | b | c |
|---|---|---|---|
| $N^1$ | 80 ± 75 | 27 ± 17 | 80 ± 75 |
| $N^2$ | 80 ± 65 | 27 ± 16 | 80 ± 65 |
| $N^3$ | 80 ± 55 | 27 ± 15 | 80 ± 55 |
| $N^4$ | 80 ± 50 | 27 ± 14 | 80 ± 50 |
| $N^5$ | 80 ± 45 | 27 ± 13 | 80 ± 45 |
| $N^6$ | 80 ± 40 | 27 ± 12 | 80 ± 40 |
| $N^7$ | 80 ± 35 | 27 ± 11 | 80 ± 35 |
| $N^8$ | 80 ± 31 | 27 ± 10 | 80 ± 31 |
| $N^9$ | 80 ± 27 | 27 ± 9 | 80 ± 27 |
| $N^{10}$ | 80 ± 23 | 27 ± 8 | 80 ± 23 |
| $N^{11}$ | 80 ± 19 | 27 ± 7 | 80 ± 19 |
| $N^{12}$ | 80 ± 15 | 27 ± 6 | 80 ± 15 |
| $N^{13}$ | 80 ± 12 | 27 ± 5 | 80 ± 12 |
| $N^{14}$ | 80 ± 9 | 27 ± 4 | 80 ± 9 |
| $N^{15}$ | 80 ± 6 | 27 ± 3 | 80 ± 6 |
| $N^{16}$ | 80 ± 3 | 27 ± 2 | 80 ± 3 |
| $N^{17}$ | 12 ± 11 | 20 ± 15 | 12 ± 11 |
| $N^{18}$ | 12 ± 8 | 20 ± 12 | 12 ± 8 |
| $N^{19}$ | 12 ± 5 | 20 ± 8 | 12 ± 5 |
| $N^{20}$ | 12 ± 2 | 20 ± 4 | 12 ± 2 |
| $N^{21}$ | 64 ± 45 | 37 ± 13 | 64 ± 45 |
| $N^{22}$ | 64 ± 20 | 37 ± 10 | 64 ± 20 |
| $N^{23}$ | 64 ± 12 | 37 ± 7 | 64 ± 12 |
| $N^{24}$ | 64 ± 5 | 37 ± 5 | 64 ± 5 |
| $N^{25}$ | 101 ± 80 | 56 ± 35 | 101 ± 80 |
| $N^{26}$ | 101 ± 55 | 56 ± 21 | 101 ± 55 |
| $N^{27}$ | 101 ± 31 | 56 ± 12 | 101 ± 31 |
| $N^{28}$ | 101 ± 15 | 56 ± 8 | 101 ± 15 |
| $N^{29}$ | 141 ± 120 | 44 ± 31 | 141 ± 120 |
| $N^{30}$ | 141 ± 90 | 44 ± 27 | 141 ± 90 |
| $N^{31}$ | 141 ± 35 | 44 ± 19 | 141 ± 35 |
| $N^{32}$ | 141 ± 17 | 44 ± 11 | 141 ± 17 |

In another preferred embodiment, the nonionic surfactant is a polyoxypropylene-polyoxyethylene block copolymer according to general formula (I-b)

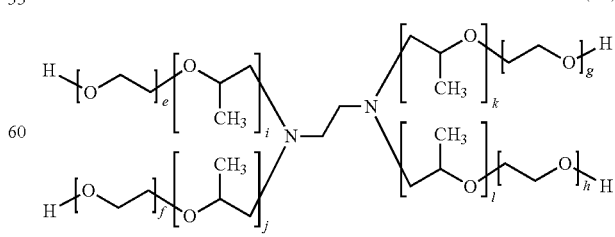

(I-b)

wherein e, f, g and h are each independently an integer of from 1 to 150, and i, j, k and l are each independently an integer of from 2 to 50; and preferably, the ratio (e+f+g+h)/(i+j+k+l) is from 0.015 to 30, in particular from 1 to 10. More preferably, e, f, g and h are each independently an integer of from 3 to 50, and i, j, k and l are each independently an integer of from 2 to 30. Tetrafunctional polyoxypropylene-polyoxyethylene block copolymers of this type are also known as poloxamines and are commercially available under the trade name Tetronics.

Preferably, the nonionic surfactant, preferably according to general formula (I-a) or according to general formula (I-b) has an average molecular weight of at least 2,000 g/mol, more preferably at least 3,000 g/mol, still more preferably at least 4,000 g/mol, yet more preferably at least 5,000 g/mol, even more preferably at least 6,000 g/mol, most preferably at least 7,000 g/mol, and in particular at least 7,500 g/mol.

In a preferred embodiment, the nonionic surfactant, preferably according to general formula (I-a) or according to general formula (I-b) has an average molecular weight of at most 30,000 g/mol, more preferably at most 25,000 g/mol, still more preferably at most 20,000 g/mol, yet more preferably at most 15,000 g/mol, even more preferably at most 12,500 g/mol, most preferably at most 10,000 g/mol, and in particular at most 9,500 g/mol.

Preferably, the nonionic surfactant, preferably according to general formula (I-a) or according to general formula (I-b) has an average molecular weight as specified as preferred embodiments $O^1$ to $O^{32}$ in the table here below:

| g/mol | $M_w$ |
|---|---|
| $O^1$ | 8,600 ± 7,500 |
| $O^2$ | 8,600 ± 5,000 |
| $O^3$ | 8,600 ± 4,000 |
| $O^4$ | 8,600 ± 3,000 |
| $O^5$ | 8,600 ± 2,500 |
| $O^6$ | 8,600 ± 2,250 |
| $O^7$ | 8,600 ± 2,000 |
| $O^8$ | 8,600 ± 1,750 |
| $O^9$ | 8,600 ± 1,500 |
| $O^{10}$ | 8,600 ± 1,400 |
| $O^{11}$ | 8,600 ± 1,300 |
| $O^{12}$ | 8,600 ± 1,200 |
| $O^{13}$ | 8,600 ± 1,100 |
| $O^{14}$ | 8,600 ± 1,000 |
| $O^{15}$ | 8,600 ± 950 |
| $O^{16}$ | 8,600 ± 920 |
| $O^{17}$ | 2,200 ± 1,000 |
| $O^{18}$ | 2,200 ± 500 |
| $O^{19}$ | 2,200 ± 250 |
| $O^{20}$ | 7,800 ± 6,000 |
| $O^{21}$ | 7,800 ± 4,000 |
| $O^{22}$ | 7,800 ± 1,500 |
| $O^{23}$ | 7,800 ± 1,000 |
| $O^{24}$ | 7,800 ± 800 |
| $O^{25}$ | 12,200 ± 8,000 |
| $O^{26}$ | 12,200 ± 4,000 |
| $O^{27}$ | 12,200 ± 3,000 |
| $O^{28}$ | 12,200 ± 1,500 |
| $O^{29}$ | 15,000 ± 7,500 |
| $O^{30}$ | 15,000 ± 5,000 |
| $O^{31}$ | 15,000 ± 3,000 |
| $O^{32}$ | 15,000 ± 2,000 |

Preferably, the nonionic surfactant, preferably according to general formula (I-a) or according to general formula (I-b) has an oxyethylene content, as determined according to USP or Ph. Eur., of at least 60%, more preferably at least 70%, still more preferably at least 72%, yet more preferably at least 74%, even more preferably at least 76%, most preferably at least 78%, and in particular at least 80%.

Preferably, the nonionic surfactant, preferably according to general formula (I-a) or according to general formula (I-b) has an oxyethylene content, as determined according to USP or Ph. Eur., of at most 90%, more preferably at most 89%, still more preferably at most 88%, yet more preferably at most 87%, even more preferably at most 86%, most preferably at most 85%, and in particular at most 84%.

Preferably, the nonionic surfactant, preferably according to general formula (I-a) or according to general formula (I-b) has an oxyethylene content, as determined according to USP or Ph. Eur., as specified as preferred embodiments $P^1$ to $P^{32}$ in the table here below:

| % | OE-content |
|---|---|
| $P^1$ | 81.8 ± 17.0 |
| $P^2$ | 81.8 ± 16.0 |
| $P^3$ | 81.8 ± 15.0 |
| $P^4$ | 81.8 ± 14.0 |
| $P^5$ | 81.8 ± 13.0 |
| $P^6$ | 81.8 ± 12.0 |
| $P^7$ | 81.8 ± 11.0 |
| $P^8$ | 81.8 ± 10.0 |
| $P^9$ | 81.8 ± 9.0 |
| $P^{10}$ | 81.8 ± 8.0 |
| $P^{11}$ | 81.8 ± 7.0 |
| $P^{12}$ | 81.8 ± 6.0 |
| $P^{13}$ | 81.8 ± 5.0 |
| $P^{14}$ | 81.8 ± 4.0 |
| $P^{15}$ | 81.8 ± 3.0 |
| $P^{16}$ | 81.8 ± 2.0 |
| $P^{17}$ | 46.5 ± 15.0 |
| $P^{18}$ | 46.5 ± 10.0 |
| $P^{19}$ | 46.5 ± 5.0 |
| $P^{20}$ | 60.0 ± 20.0 |
| $P^{21}$ | 60.0 ± 15.0 |
| $P^{22}$ | 70.0 ± 10.0 |
| $P^{23}$ | 70.0 ± 8.0 |
| $P^{24}$ | 70.0 ± 5.0 |
| $P^{25}$ | 73.0 ± 6.0 |
| $P^{26}$ | 73.0 ± 4.0 |
| $P^{27}$ | 75.0 ± 5.0 |
| $P^{28}$ | 75.0 ± 4.0 |
| $P^{29}$ | 75.0 ± 3.0 |
| $P^{30}$ | 85.0 ± 5.0 |
| $P^{31}$ | 85.0 ± 4.0 |
| $P^{32}$ | 85.0 ± 3.0 |

The content of the nonionic surfactant in the pharmaceutical dosage form is not limited.

Preferably, the content of the nonionic surfactant in the pharmaceutical dosage form according to the invention is such that liquid extraction of the pharmacologically active compound and thus, parenteral administration of the liquid extract, is impeded.

Preferably, the content of the nonionic surfactant is at least 0.1 wt.-%, more preferably at least 1.0 wt.-%, still more at least 5 wt.-%, yet more preferably at least 10 wt.-%, most preferably at least 15 wt.-%, and in particular at least 20 wt.-%, based on the total weight of the pharmaceutical dosage form.

Preferably, the content of the nonionic surfactant is within the range of from 0.1 to 60 wt.-%, more preferably 5 to 50 wt.-%, still more preferably 10 to 45 wt.-%, most preferably 15 to 40 wt.-%, and in particular 20 to 35 wt.-%, based on the total weight of the pharmaceutical dosage form.

In a preferred embodiment, the content of nonionic surfactant is within the range of 15±12 wt.-%, more preferably 15±10 wt.-%, most preferably 15±7 wt.-%, and in particular 15±5 wt.-%, based on the total weight of the pharmaceutical dosage form. In another preferred embodiment, the content of nonionic surfactant is within the range of 20±18 wt.-%, more preferably 20±15 wt.-%, still more preferably 20±12 wt.-%, most preferably 20±10 wt.-%, 20±7 wt.-%, and in particular 20±5 wt.-%, based on the total weight of the pharmaceutical dosage form. In a further preferred embodiment, the content of nonionic surfactant is within the range of 25±20 wt.-%, more preferably 25±17 wt.-%, still more preferably 25±15 wt.-%, even more preferably 25±10 wt.-%, most preferably 25±7 wt.-%, and in particular 25±5 wt.-%, based on the total weight of the pharmaceutical dosage form.

In a preferred embodiment, the content of nonionic surfactant is within the range of 30±20 wt.-%, more preferably 30±17 wt.-%, still more preferably 30±15 wt.-%, even more preferably 30±10 wt.-%, most preferably 30±7 wt.-%, and in particular 30±5 wt.-%, based on the total weight of the pharmaceutical dosage form. In another further preferred embodiment, the content of nonionic surfactant is within the range of 35±20 wt.-%, more preferably 35±17 wt.-%, still more preferably 35±15 wt.-%, even more preferably 35±10 wt.-%, most preferably 35±7 wt.-%, and in particular 35±5 wt.-%, based on the total weight of the pharmaceutical dosage form. In a further preferred embodiment, the content of nonionic surfactant is within the range of 40±25 wt.-%, more preferably 40±15 wt.-%, still more preferably 40±10 wt.-%, most preferably 40±7 wt.-%, and in particular 40±5 wt.-%, based on the total weight of the pharmaceutical dosage form.

Preferably, the total amount of the nonionic surfactant that is contained in the pharmaceutical dosage form is within the range of from 0.1 to 750 mg, more preferably 10 to 500 mg, still more preferably 25 to 400 mg, yet more preferably 50 to 350 mg, most preferably 75 to 300 mg and in particular 100 to 250 mg.

In a preferred embodiment, the nonionic surfactant is contained in the pharmaceutical dosage form in an amount of 100±95 mg, 100±90 mg, 100±80 mg, 100±70 mg, 100±60 mg, 100±50 mg, 100±40 mg, 100±30 mg, 100±20 mg, or 100±10 mg. In another preferred embodiment, the nonionic surfactant is contained in the pharmaceutical dosage form in an amount of 120±115 mg, 120±100 mg, 120±90 mg, 120±80 mg, 120±70 mg, 120±60 mg, 120±50 mg, 120±40 mg, 120±30 mg, 120±20 mg, or 120±10 mg. In still another preferred embodiment, the nonionic surfactant is contained in the pharmaceutical dosage form in an amount of 140±135 mg, 140±120 mg, 140±110 mg, 140±100 mg, 140±90 mg, 140±80 mg, 140±70 mg, 140±60 mg, 140±50 mg, 140±40 mg, 140±30 mg, 140±20 mg, or 140±10 mg. In yet another preferred embodiment, the nonionic surfactant is contained in the pharmaceutical dosage form in an amount of 160±155 mg, 160±140 mg, 160±130 mg, 160±120 mg, 160±110 mg, 160±100 mg, 160±90 mg, 160±80 mg, 160±70 mg, 160±60 mg, 160±50 mg, 160±40 mg, 160±30 mg, 160±20 mg, or 160±10 mg.

In a preferred embodiment, the nonionic surfactant is contained in the pharmaceutical dosage form in an amount of 180±175 mg, 180±160 mg, 180±150 mg, 180±140 mg, 180±130 mg, 180±120 mg, 180±110 mg, 180±100 mg, 180±90 mg, 180±80 mg, 180±70 mg, 180±60 mg, 180±50 mg, 180±40 mg, 180±30 mg, 180±20 mg, or 180±10 mg. In another preferred embodiment, the nonionic surfactant is contained in the pharmaceutical dosage form in an amount of 200±190 mg, 200±180 mg, 200±170 mg, 200±160 mg, 200±150 mg, 200±140 mg, 200±130 mg, 200±120 mg, 200±110 mg, 200±100 mg, 200±90 mg, 200±80 mg, 200±70 mg, 200±60 mg, 200±50 mg, 200±40 mg, 200±30 mg, 200±20 mg, or 200±10 mg. In still another preferred embodiment, the nonionic surfactant is contained in the pharmaceutical dosage form in an amount of 220±210 mg, 220±200 mg, 220±180 mg, 220±160 mg, 220±150 mg, 220±140 mg, 220±130 mg, 220±120 mg, 220±110 mg, 220±100 mg, 220±90 mg, 220±80 mg, 220±70 mg, 220±60 mg, 220±50 mg, 220±40 mg, 220±30 mg, 220±20 mg, or 220±10 mg. In yet another preferred embodiment, the nonionic surfactant is contained in the pharmaceutical dosage form in an amount of 240±210 mg, 240±200 mg, 240±180 mg, 240±160 mg, 240±150 mg, 240±140 mg, 240±130 mg, 240±120 mg, 240±110 mg, 240±100 mg, 240±90 mg, 240±80 mg, 240±70 mg, 240±60 mg, 240±50 mg, 240±40 mg, 240±30 mg, 240±20 mg, or 240±10 mg.

Preferably, the relative weight ratio of the pharmacologically active compound and the nonionic surfactant is within the range of from 20:1 to 1:20, more preferably 15:1 to 1:15, still more preferably 10:1 to 1:10, yet more preferably 5:1 to 1:10, even more preferably 2:1 to 1:5, most preferably 1:1 to 1:4, and in particular 1:1.5 to 1:3.

In a preferred embodiment, the relative weight ratio of the pharmacologically active compound and the nonionic surfactant is at most 6.5:1, more preferably at most 5.0:1, still more preferably at most 4.0:1, yet more preferably at most 3.0:1, even more preferably at most 2.5:1, most preferably at most 2.0:1, and in particular at most 1.5:1. In a particularly preferred embodiment, the relative weight ratio of the pharmacologically active compound and the nonionic surfactant is at most 1.4:1, more preferably at most 1.3:1, still more preferably at most 1.2:1, yet more preferably at most 1.1:1, even more preferably at most 1.0:1, most preferably at most 0.9:1, and in particular at most 0.8:1.

Preferably, the relative weight ratio of the anionic polymer and the nonionic surfactant is within the range of from 20:1 to 1:20, more preferably 15:1 to 1:15, still more preferably 10:1 to 1:10, yet more preferably 5:1 to 1:5, even more preferably 5:1 to 1:3, most preferably 3:1 to 1:2, and in particular 2:1 to 1:2.

In a preferred embodiment, the nonionic surfactant is homogeneously distributed in the pharmaceutical dosage form according to the invention.

Preferably, the pharmacologically active compound, the anionic polymer and the nonionic surfactant are homogeneously distributed over the pharmaceutical dosage form or, when the pharmaceutical dosage form comprises a film coating, over the coated core of the pharmaceutical dosage form.

In a particularly preferred embodiment, the pharmacologically active compound, the anionic polymer and the nonionic surfactant are intimately mixed with one another, so that the pharmaceutical dosage form does not contain any segments where either pharmacologically active compound is present in the absence of anionic polymer and/or the nonionic surfactant, or where anionic polymer is present in the absence of pharmacologically active compound and/or the surfactant.

Preferably, the pharmacologically active compound and the nonionic surfactant are homogeneously dispersed in the anionic polymer, preferably in molecular disperse form or solid disperse form. In other words, the pharmacologically active compound and the nonionic surfactant preferably form a solid solution or solid dispersion in the anionic polymer.

Preferably, the pharmacologically active compound is embedded in a prolonged release matrix comprising the anionic polymer and the nonionic surfactant. Thus, the prolonged release matrix is preferably a hydrophilic matrix. Preferably, the release profile of the pharmacologically active compound is matrix-retarded. Preferably, the pharmacologically active compound is embedded in a matrix comprising the anionic polymer and the nonionic surfactant, said matrix controlling the release of the pharmacologically active compound from the pharmaceutical dosage form.

Physiologically acceptable materials which are known to the person skilled in the art may be used as supplementary matrix materials. Polymers, particularly preferably cellulose ethers and/or cellulose esters are preferably used as supplementary hydrophilic matrix materials. Ethylcellulose, hydroxypropylmethylcellulose, hydroxypropylcellulose, hydroxymethylcellulose, hydroxyethylcellulose, and/or the derivatives thereof, such as the salts thereof are very particularly preferably used as matrix materials.

Preferably, the pharmaceutical dosage form according to the invention is for oral administration.

In a preferred embodiment, the pharmaceutical dosage form according to the invention is configured for administration once daily, preferably orally. In another preferred embodiment, the pharmaceutical dosage form according to the invention is configured for administration twice daily, preferably orally. In still another preferred embodiment, the pharmaceutical dosage form according to the invention is configured for administration thrice daily, preferably orally.

For the purpose of the specification, "twice daily" means equal or nearly equal time intervals, i.e., about every 12 hours, or different time intervals, e.g., 8 and 16 hours or 10 and 14 hours, between the individual administrations.

For the purpose of the specification, "thrice daily" means equal or nearly equal time intervals, i.e., about every 8 hours, or different time intervals, e.g., 6, 6 and 12 hours; or 7, 7 and 10 hours, between the individual administrations.

Preferably, the pharmaceutical dosage form according to the invention causes an at least partially delayed or prolonged release of pharmacologically active compound.

Controlled or prolonged release is understood according to the invention preferably to mean a release profile in which the pharmacologically active compound is released over a relatively long period with reduced intake frequency with the purpose of extended therapeutic action of the pharmacologically active compound. Preferably, the meaning of the term "prolonged release" is in accordance with the European guideline on the nomenclature of the release profile of pharmaceutical dosage forms (CHMP). This is achieved in particular with peroral administration. The expression "at least partially delayed or prolonged release" covers according to the invention any pharmaceutical dosage forms which ensure modified release of the pharmacologically active compound contained therein. The pharmaceutical dosage forms preferably comprise coated or uncoated pharmaceutical dosage forms, which are produced with specific auxiliary substances, by particular processes or by a combination of the two possible options in order purposefully to change the release rate or location of release.

In the case of the pharmaceutical dosage forms according to the invention, the release profile of a controlled release form may be modified e.g. as follows: extended release, repeat action release, prolonged release and sustained release.

For the purpose of the specification "controlled release" preferably means a product in which the release of active compound over time is controlled by the type and composition of the formulation. For the purpose of the specification "extended release" preferably means a product in which the release of active compound is delayed for a finite lag time, after which release is unhindered. For the purpose of the specification "repeat action release" preferably means a product in which a first portion of active compound is released initially, followed by at least one further portion of active compound being released subsequently. For the purpose of the specification "prolonged release" preferably means a product in which the rate of release of active compound from the formulation after administration has been reduced over time, in order to maintain therapeutic activity, to reduce toxic effects, or for some other therapeutic purpose. For the purpose of the specification "sustained release" preferably means a way of formulating a medicine so that it is released into the body steadily, over a long period of time, thus reducing the dosing frequency. For further details, reference may be made, for example, to K. H. Bauer, Lehrbuch der Pharmazeutischen Technologie, 6th edition, WVG Stuttgart, 1999; and Eur. Ph.

The pharmaceutical dosage form according to the invention may comprise one or more pharmacologically active compounds at least in part in a further controlled release form, wherein controlled release may be achieved with the assistance of conventional materials and processes known to the person skilled in the art, for example by embedding the substances in a controlled release matrix or by applying one or more controlled release coatings. Substance release must, however, be controlled such that addition of delayed-release materials does not impair the necessary breaking strength. Controlled release from the pharmaceutical dosage form according to the invention is preferably achieved by embedding the pharmacologically active compound in a matrix. Matrix materials may, for example, be hydrophilic, gel-forming materials, from which release proceeds mainly by erosion and diffusion. Preferably, the anionic polymer and the nonionic surfactant serve as matrix material, optionally in combination with auxiliary substances also acting as matrix materials.

Preferably, the release profile is substantially matrix controlled, preferably by embedding the pharmacologically active compound in a matrix comprising the anionic polymer and optionally, further matrix materials, such as the nonionic surfactant and/or the optionally present further polymer. Preferably, the release profile is not osmotically driven. Preferably, release kinetics is not zero order.

In preferred embodiments, in accordance with Ph. Eur., the in vitro release profile of the pharmacologically active compound complies with any same single one of the following release profiles $R^1$ to $R^{50}$:

| % | $R^1$ | $R^2$ | $R^3$ | $R^4$ | $R^5$ | $R^6$ | $R^7$ | $R^8$ | $R^9$ | $R^{10}$ |
|---|---|---|---|---|---|---|---|---|---|---|
| 1 h | 15 ± 14 | 15 ± 13 | 15 ± 12 | 15 ± 11 | 15 ± 10 | 15 ± 9 | 15 ± 8 | 15 ± 7 | 15 ± 6 | 15 ± 5 |
| 2 h | 25 ± 20 | 25 ± 18 | 25 ± 17 | 25 ± 16 | 25 ± 15 | 25 ± 14 | 25 ± 13 | 25 ± 12 | 25 ± 11 | 25 ± 10 |
| 8 h | 55 ± 35 | 55 ± 32 | 55 ± 29 | 55 ± 27 | 55 ± 25 | 55 ± 23 | 55 ± 21 | 55 ± 19 | 55 ± 17 | 55 ± 15 |
| 12 h | 70 ± 35 | 70 ± 32 | 70 ± 29 | 70 ± 27 | 70 ± 25 | 70 ± 23 | 70 ± 21 | 70 ± 19 | 70 ± 17 | 70 ± 15 |
| 24 h | ≥65 | ≥70 | ≥70 | ≥70 | ≥75 | ≥75 | ≥75 | ≥80 | ≥80 | ≥80 |

-continued

| % | $R^{11}$ | $R^{12}$ | $R^{13}$ | $R^{14}$ | $R^{15}$ | $R^{16}$ | $R^{17}$ | $R^{18}$ | $R^{19}$ | $R^{20}$ |
|---|---|---|---|---|---|---|---|---|---|---|
| 1 h | 20 ± 18 | 20 ± 16 | 20 ± 14 | 20 ± 12 | 20 ± 10 | 20 ± 9 | 20 ± 8 | 20 ± 7 | 20 ± 6 | 20 ± 5 |
| 2 h | 30 ± 28 | 30 ± 26 | 30 ± 24 | 30 ± 22 | 30 ± 20 | 30 ± 18 | 30 ± 16 | 30 ± 14 | 30 ± 12 | 30 ± 10 |
| 8 h | 60 ± 35 | 60 ± 32 | 60 ± 29 | 60 ± 27 | 60 ± 25 | 60 ± 23 | 60 ± 21 | 60 ± 19 | 60 ± 17 | 60 ± 15 |
| 12 h | 75 ± 35 | 75 ± 32 | 75 ± 29 | 75 ± 27 | 75 ± 30 | 75 ± 23 | 75 ± 21 | 75 ± 19 | 75 ± 17 | 75 ± 15 |
| 24 h | ≥75 | ≥77 | ≥79 | ≥81 | ≥83 | ≥85 | ≥87 | ≥89 | ≥90 | ≥90 |

| % | $R^{21}$ | $R^{22}$ | $R^{23}$ | $R^{24}$ | $R^{30}$ | $R^{26}$ | $R^{27}$ | $R^{28}$ | $R^{29}$ | $R^{30}$ |
|---|---|---|---|---|---|---|---|---|---|---|
| 1 h | 25 ± 14 | 25 ± 14 | 25 ± 12 | 25 ± 12 | 25 ± 10 | 25 ± 9 | 25 ± 8 | 25 ± 7 | 25 ± 6 | 25 ± 5 |
| 2 h | 35 ± 18 | 35 ± 17 | 35 ± 16 | 35 ± 15 | 35 ± 14 | 35 ± 13 | 35 ± 12 | 35 ± 11 | 35 ± 10 | 35 ± 10 |
| 8 h | 65 ± 35 | 65 ± 32 | 65 ± 29 | 65 ± 27 | 60 ± 25 | 65 ± 23 | 60 ± 21 | 65 ± 19 | 65 ± 17 | 65 ± 15 |
| 12 h | ≥70 | ≥72 | ≥74 | ≥76 | ≥78 | ≥80 | ≥82 | ≥84 | ≥86 | ≥88 |
| 24 h | ≥75 | ≥77 | ≥79 | ≥81 | ≥83 | ≥85 | ≥87 | ≥89 | ≥90 | ≥90 |

| % | $R^{31}$ | $R^{32}$ | $R^{33}$ | $R^{34}$ | $R^{35}$ | $R^{36}$ | $R^{37}$ | $R^{38}$ | $R^{39}$ | $R^{40}$ |
|---|---|---|---|---|---|---|---|---|---|---|
| 1 h | 8 ± 7 | 8 ± 6 | 8 ± 5 | 8 ± 4 | 13 ± 12 | 13 ± 10 | 13 ± 8 | 13 ± 6 | 15 ± 10 | 15 ± 7 |
| 2 h | 15 ± 14 | 15 ± 11 | 15 ± 8 | 15 ± 5 | 20 ± 23 | 20 ± 18 | 20 ± 13 | 20 ± 8 | 25 ± 15 | 25 ± 10 |
| 8 h | 40 ± 34 | 40 ± 26 | 40 ± 18 | 40 ± 10 | 45 ± 24 | 45 ± 18 | 45 ± 12 | 45 ± 6 | 50 ± 25 | 50 ± 15 |
| 12 h | ≥50 | ≥54 | ≥58 | ≥60 | 60 ± 29 | 60 ± 22 | 60 ± 15 | 60 ± 9 | 70 ± 25 | 70 ± 20 |
| 24 h | ≥70 | ≥70 | ≥75 | ≥75 | ≥70 | ≥75 | ≥80 | ≥85 | ≥75 | ≥80 |

| % | $R^{41}$ | $R^{42}$ | $R^{43}$ | $R^{44}$ | $R^{45}$ | $R^{46}$ | $R^{47}$ | $R^{48}$ | $R^{49}$ | $R^{50}$ |
|---|---|---|---|---|---|---|---|---|---|---|
| 1 h | 15 ± 7 | 15 ± 5 | 20 ± 12 | 20 ± 9 | 20 ± 7 | 20 ± 5 | 25 ± 24 | 25 ± 18 | 25 ± 12 | 25 ± 6 |
| 2 h | 20 ± 10 | 25 ± 5 | 25 ± 15 | 25 ± 11 | 25 ± 9 | 25 ± 7 | 35 ± 30 | 35 ± 27 | 35 ± 20 | 45 ± 11 |
| 8 h | 50 ± 10 | 55 ± 5 | 60 ± 20 | 60 ± 15 | 60 ± 12 | 60 ± 10 | 70 ± 35 | 70 ± 20 | 70 ± 15 | 70 ± 10 |
| 12 h | 70 ± 15 | 75 ± 5 | 75 ± 30 | 75 ± 20 | 75 ± 18 | 75 ± 13 | 80 ± 30 | 80 ± 25 | 80 ± 18 | 80 ± 13 |
| 24 h | ≥90 | ≥95 | >95 | >95 | >95 | ≥98 | >95 | >95 | ≥98 | ≥98 |

Suitable in vitro conditions are known to the skilled artisan. In this regard it can be referred to, e.g., the Ph. Eur. Preferably, the in vitro release profile is measured under the following conditions: 600 ml phosphate buffer (pH 6.8) at temperature of 37° C. with sinker (type 1 or 2); rotation speed of the paddle: 75 min$^{-1}$.

Preferably, the release profile of the pharmaceutical dosage form according to the invention is stable upon storage, preferably upon storage at elevated temperature, e.g. 37° C., for 3 months in sealed containers. In this regard "stable" means that when comparing the initial release profile with the release profile after storage, at any given time point the release profiles deviate from one another absolutely by not more than 20%, more preferably not more than 15%, still more preferably not more than 10%, yet more preferably not more than 7.5%, most preferably not more than 5.0%. and in particular not more than 2.5%.

Preferably, the pharmaceutical dosage form according to the invention is monolithic. Preferably, the pharmaceutical dosage form is a monolithic mass.

In the manufacturing process of the pharmaceutical dosage form according to the invention, all polymers are preferably employed as powders.

Preferably, the pharmaceutical dosage form according to the invention is thermoformed, more preferably hot-melt extruded, although also other methods of thermoforming may be used in order to manufacture the pharmaceutical dosage form according to the invention, such as press-molding at elevated temperature or heating of tablets that were manufactured by conventional compression in a first step and then heated above the softening temperature of the polymer in the tablet in a second step to form hard tablets. In this regards, thermoforming means forming or molding of a mass after the application of heat.

In a preferred embodiment, the pharmaceutical dosage form is thermoformed by hot-melt extrusion. The melt extruded strands are preferably cut into monoliths, which are then preferably formed into tablets. In this regard, the term "tablets" is preferably not to be understood as pharmaceutical dosage forms being made by compression of powder or granules (compressi) but rather, as shaped extrudates.

In a preferred embodiment, the pharmaceutical dosage form has a total weight within the range of 100±75 mg, more preferably 100±50 mg, most preferably 100±25 mg. In another preferred embodiment, the pharmaceutical dosage form has a total weight within the range of 200±75 mg, more preferably 200±50 mg, most preferably 200±25 mg. In another preferred embodiment, the pharmaceutical dosage form has a total weight within the range of 250±75 mg, more preferably 250±50 mg, most preferably 250±25 mg. In still another preferred embodiment, the pharmaceutical dosage form has a total weight within the range of 300±75 mg, more preferably 300±50 mg, most preferably 300±25 mg. In yet another preferred embodiment, the pharmaceutical dosage form has a total weight within the range of 400±75 mg, more preferably 400±50 mg, most preferably 400±25 mg.

In a preferred embodiment, the pharmaceutical dosage form has a total weight within the range of 500±250 mg, more preferably 500±200 mg, most preferably 500±150 mg. In another preferred embodiment, the pharmaceutical dosage form has a total weight within the range of 750±250 mg, more preferably 750±200 mg, most preferably 750±150 mg. In another preferred embodiment, the pharmaceutical dosage form has a total weight within the range of 1000±250 mg, more preferably 1000±200 mg, most preferably 1000±150 mg. In still another preferred embodiment, the pharmaceutical dosage form has a total weight within the range of 1250±250 mg, more preferably 1250±200 mg, most preferably 1250±150 mg.

The pharmaceutical dosage form according to the invention is characterized by excellent storage stability. Preferably, after storage for 4 weeks at 40° C. and 75% rel. humidity, the content of pharmacologically active compound amounts to at least 90%, more preferably at least 91%, still more preferably at least 92%, yet more preferably at least 93%, most preferably at least 94% and in particular at least 95%, of its original content before storage. Suitable methods for measuring the content of the pharmacologically active compound in the pharmaceutical dosage form are known to the skilled artisan. In this regard it is referred to the Eur. Ph. or the USP, especially to reversed phase HPLC analysis. Preferably, the pharmaceutical dosage form is stored in closed, preferably sealed containers, most preferably being equipped with an oxygen scavenger, in particular with an oxygen scavenger that is effective even at low relative humidity.

In a preferred embodiment, after oral administration of the pharmaceutical dosage form according to the invention, in vivo the average peak plasma level ($C_{max}$) of the pharmacologically active compound is on average reached after $t_{max}$ 4.0±2.5 h, more preferably after $t_{max}$ 4.0±2.0 h, still more preferably after $t_{max}$ 4.0±1.5 h, most preferably after $t_{max}$ 4.0±1.0 h and in particular after $t_{max}$ 4.0±0.5 h. In another preferred embodiment, after oral administration of the pharmaceutical dosage form according to the invention, in vivo the average peak plasma level ($C_{max}$) of the pharmacologically active compound is on average reached after $t_{max}$ 5.0±2.5 h, more preferably after $t_{max}$ 5.0±2.0 h, still more preferably after $t_{max}$ 5.0±1.5 h, most preferably after $t_{max}$ 5.0±1.0 h and in particular after $t_{max}$ 5.0±0.5 h. In still another preferred embodiment, after oral administration of the pharmaceutical dosage form according to the invention, in vivo the average peak plasma level ($C_{max}$) of the pharmacologically active compound is on average reached after $t_{max}$ 6.0±2.5 h, more preferably after $t_{max}$ 6.0±2.0 h, still more preferably after $t_{max}$ 6.0±1.5 h, most preferably after $t_{max}$ 6.0±1.0 h and in particular after $t_{max}$ 6.0±0.5 h.

In a preferred embodiment, the average value for $t_{1/2}$ of the pharmacologically active compound after oral administration of the pharmaceutical dosage form according to the invention in vivo is 4.0±2.5 h, more preferably 4.0±2.0 h, still more preferably 4.0±1.5 h, most preferably 4.0±1.0 h, and in particular 4.0±0.5 h. In another preferred embodiment, the average value for $t_{1/2}$ of the pharmacologically active compound after oral administration of the pharmaceutical dosage form according to the invention in vivo is preferably 5.0±2.5 h, more preferably 5.0±2.0 h, still more preferably 5.0±1.5 h, most preferably 5.0±1.0 h, and in particular 5.0±0.5 h. In still another preferred embodiment, the average value for $t_{1/2}$ of the pharmacologically active compound after oral administration of the pharmaceutical dosage form according to the invention in vivo is preferably 6.0±2.5 h, more preferably 6.0±2.0 h, still more preferably 6.0±1.5 h, most preferably 6.0±1.0 h, and in particular 6.0±0.5 h.

Preferably, $C_{max}$ of the pharmacologically active compound does not exceed 0.01 ng/ml, or 0.05 ng/ml, or 0.1 ng/ml, or 0.5 ng/ml, or 1.0 ng/ml, or 2.5 ng/ml, or 5 ng/ml, or 10 ng/ml, or 20 ng/ml, or 30 ng/ml, or 40 ng/ml, or 50 ng/ml, or 75 ng/ml, or 100 ng/ml, or 150 ng/ml, or 200 ng/ml, or 250 ng/ml, or 300 ng/ml, or 350 ng/ml, or 400 ng/ml, or 450 ng/ml, or 500 ng/ml, or 750 ng/ml, or 1000 ng/ml.

In a preferred embodiment, the pharmaceutical dosage form according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding active compound, for example due to increased nasal secretion or sneezing. Further examples of substances which irritate the nasal passages and/or pharynx are those which cause burning, itching, urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance drug. Corresponding hot substance drugs are known per se to the person skilled in the art and are described, for example, in "Pharmazeutische Biologie—Drogen and ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure.

The pharmaceutical dosage form according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no emetic based on one or more constituents of ipecacuanha (ipecac) root, for example based on the constituent emetine, as are, for example, described in "Pharmazeutische Biologie—Drogen and ihre Inhaltsstoffe" by Prof. Dr. Hildebert Wagner, 2nd, revised edition, Gustav Fischer Verlag, Stuttgart, N.Y., 1982. The corresponding literature description is hereby introduced as a reference and is deemed to be part of the disclosure. The pharmaceutical dosage form according to the invention preferably also contains no apomorphine as an emetic.

The pharmaceutical dosage form according to the invention preferably also contains no bitter substance. Bitter substances and the quantities effective for use may be found in US-2003/0064099 A1, the corresponding disclosure of which should be deemed to be the disclosure of the present application and is hereby introduced as a reference. Examples of bitter substances are aromatic oils, such as peppermint oil, *eucalyptus* oil, bitter almond oil, menthol, fruit aroma substances, aroma substances from lemons, oranges, limes, grapefruit or mixtures thereof, and/or denatonium benzoate.

The pharmaceutical dosage form according to the invention accordingly preferably contains neither substances which irritate the nasal passages and/or pharynx, nor emetics, nor bitter substances.

Preferably, the pharmaceutical dosage form according to the invention contains no neuroleptics, for example a compound selected from the group consisting of haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

In a preferred embodiment, the pharmaceutical dosage form according to the invention contains no pharmacologically active compound antagonists.

In another preferred embodiment, the pharmaceutical dosage form according to the invention does contain a pharmacologically active compound antagonist. Pharmacologically active compound antagonists suitable for a given pharmacologically active compound are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains an opioid as pharmacologically active compound and an opioid antagonist as pharmacologically active compound antagonist, wherein the opioid antagonist is selected from the group consisting of naloxone, naltrexone, nalmefene, nalide, nalmexone, nalorphine or naluphine, in each case optionally in the form of a corresponding physiologically acceptable compound, in particular in the form of a base, a salt or solvate. Naloxone and nalmexone as well as their physiologically acceptable salts are preferred pharmacologically active compound antagonists. The content of the pharmacologically active compound antagonist in the pharmaceutical dosage form is not limited.

Besides the pharmacologically active compound, the anionic polymer and the nonionic surfactant the pharmaceutical dosage form according to the invention may contain further constituents, such as conventional pharmaceutical excipients.

Preferably, the pharmaceutical dosage form according to the invention contains a plasticizer.

Preferred plasticizers are polyalkylene glycols, like polyethylene glycol, triacetin, fatty acids, fatty acid esters, waxes and/or microcrystalline waxes. Particularly preferred plasticizers are polyethylene glycols, such as PEG 6000.

Preferably, the content of the plasticizer is within the range of from 0.1 to 30 wt.-%, more preferably 0.5 to 27.5 wt.-%, still more preferably 1.0 to 25 wt.-%, yet more preferably 5 to 25 wt.-%, most preferably 10 to 20 wt.-% and in particular 12.5 to 17.5 wt.-%, based on the total weight of the pharmaceutical dosage form.

In a preferred embodiment, the plasticizer is a polyalkylene glycol having a content within the range of 5±4 wt.-%, more preferably 5±3.5 wt.-%, still more preferably 5±3 wt.-%, yet more preferably 5±2.5 wt.-%, most preferably 5±2 wt.-%, and in particular 5±1.5 wt.-%, based on the total weight of the pharmaceutical dosage form.

In another preferred embodiment, the plasticizer is a polyalkylene glycol having a content within the range of 10±8 wt.-%, more preferably 10±6 wt.-%, still more preferably 10±5 wt.-%, yet more preferably 10±4 wt.-%, most preferably 10±3 wt.-%, and in particular 10±2 wt.-%, based on the total weight of the pharmaceutical dosage form.

In still another preferred embodiment, the plasticizer is a polyalkylene glycol having a content within the range of 15±8 wt.-%, more preferably 15±6 wt.-%, still more preferably 15±5 wt.-%, yet more preferably 15±4 wt.-%, most preferably 15±3 wt.-%, and in particular 15±2 wt.-%, based on the total weight of the pharmaceutical dosage form.

Preferably, the relative weight ratio of the anionic polymer and the plasticizer is within the range of from 0.1:1 to 5.0:1, more preferably from 0.2:1 to 4.0:1.

In a preferred embodiment, the relative weight ratio of the anionic polymer and the plasticizer is at least 0.2:1, more preferably at least 0.4:1, still more preferably at least 0.6:1, yet more preferably at least 0.8:1, even more preferably at least 1.0:1, most preferably at least 1.2:1, and in particular at least 1.4:1.

Preferably, the relative weight ratio of the nonionic surfactant and the plasticizer is within the range of from 0.1:1 to 5.0:1, more preferably from 0.2:1 to 4.0:1.

In a preferred embodiment, the relative weight ratio of the nonionic surfactant and the plasticizer is at least 0.2:1, more preferably at least 0.4:1, still more preferably at least 0.6:1, yet more preferably at least 0.8:1, even more preferably at least 1.0:1, most preferably at least 1.2:1, and in particular at least 1.4:1.

Preferably, the relative weight ratio of the sum of anionic polymer and nonionic surfactant to the plasticizer is within the range of from 0.1:1 to 7.0:1, more preferably from 0.2:1 to 6.5:1.

In a preferred embodiment, the relative weight ratio of the sum of anionic polymer and nonionic surfactant to the plasticizer is at least 0.2:1, more preferably at least 0.4:1, still more preferably at least 0.6:1, yet more preferably at least 0.8:1, even more preferably at least 1.0:1, most preferably at least 1.2:1, and in particular at least 1.4:1. In a particularly preferred embodiment, the relative weight ratio of the sum of anionic polymer and nonionic surfactant to the plasticizer is at least 1.6:1, more preferably at least 1.8:1, still more preferably at least 2.0:1, yet more preferably at least 2.2:1, even more preferably at least 2.4:1, most preferably at least 2.6:1, and in particular at least 2.8:1.

The pharmaceutical dosage form according to the invention may further contain an antioxidant.

Suitable antioxidants include ascorbic acid, α-tocopherol (vitamin E), butylhydroxyanisol, butylhydroxytoluene, salts of ascorbic acid (vitamin C), ascorbylic palmitate, monothioglycerine, coniferyl benzoate, nordihydroguajaretic acid, gallus acid esters, phosphoric acid, and the derivatives thereof, such as vitamin E-succinate or vitamin E-palmitate and/or sodium bisulphite, more preferably butylhydroxytoluene (BHT) or butylhydroxyanisol (BHA) and/or α-tocopherol. A particularly preferred antioxidant is α-tocopherol.

In a preferred embodiment, the pharmaceutical dosage form according to the invention does either not contain any antioxidant, or contains one or more antioxidants, wherein the content of all antioxidant(s) being present in the dosage form preferably amounts to at most 5.0 wt.-%, more preferably at most 2.5 wt.-%, more preferably at most 1.5 wt.-%, still more preferably at most 1.0 wt.-%, yet more preferably at most 0.5 wt.-%, most preferably at most 0.4 wt.-% and in particular at most 0.3 wt.-%, 0.2 wt.-% or 0.1 wt.-%, based on the total weight of the pharmaceutical dosage form.

The pharmaceutical dosage form according to the invention may further contain a free physiologically acceptable acid. The acid may be organic or inorganic, liquid or solid. Solid acids are preferred, particularly crystalline organic or inorganic acids.

Preferably, the acid is free. This means that the acidic functional groups of the acid are not all together constituents of a salt of the pharmacologically active compound. If the pharmacologically active compound is present as a salt of an acid, e.g. as hydrochloride, the pharmaceutical dosage form according to the invention preferably contains as acid another, chemically different acid which is not present as a constituent of the salt of the pharmacologically active compound. In other words, monoacids that form a salt with the pharmacologically active compound are not to be considered as free acids in the meaning of the invention. When acid has more than a single acidic functional group (e.g. phosphoric acid), the acid may be present as a constituent of a salt of the pharmacologically active compound, provided that at least one of the acidic functional groups of the acid is not involved in the formation of the salt, i.e. is free. Preferably, however, each and every acidic functional group of acid is not involved in the formation of a salt with pharmacologically active compound. It is also possible, however, that free acid and the acid forming a salt with pharmacologically active compound are identical. Under these circumstances the acid is preferably present in molar excess compared to pharmacologically active compound.

In a preferred embodiment, the acid contains at least one acidic functional group (e.g. —$CO_2H$, —$SO_3H$, —$PO_3H_2$, —OH and the like) having a $pK_A$ value within the range of 2.00±1.50, more preferably 2.00±1.25, still more preferably 2.00±1.00, yet more preferably 2.00±0.75, most preferably 2.00±0.50 and in particular 2.00±0.25. In another preferred embodiment, the acid contains at least one acidic functional group having a $pK_A$ value within the range of 2.25±1.50, more preferably 2.25±1.25, still more preferably 2.25±1.00, yet more preferably 2.25±0.75, most preferably 2.25±0.50 and in particular 2.25±0.25. In another preferred embodiment, the acid contains at least one acidic functional group having a $pK_A$ value within the range of 2.50±1.50, more preferably 2.50±1.25, still more preferably 2.50±1.00, yet more preferably 2.50±0.75, most preferably 2.50±0.50 and in particular 2.50±0.25. In another preferred embodiment, the acid contains at least one acidic functional group having a $pK_A$ value within the range of 2.75±1.50, more preferably 2.75±1.25, still more preferably 2.75±1.00, yet more preferably 2.75±0.75, most preferably 2.75±0.50 and in particular 2.75±0.25. In another preferred embodiment, the acid contains at least one acidic functional group having a $pK_A$ value within the range of 3.00±1.50, more preferably 3.00±1.25, still more preferably 3.00±1.00, yet more preferably 3.00±0.75, most preferably 3.00±0.50 and in particular 3.00±0.25. In still another preferred embodiment, the acid contains at least one acidic functional group having a $pK_A$ value within the range of 3.25±1.50, more preferably 3.25±1.25, still more preferably 3.25±1.00, yet more preferably 3.25±0.75, most preferably 3.25±0.50 and in particular 3.25±0.25.

In yet another preferred embodiment, the acid contains at least one acidic functional group having a $pK_A$ value within the range of 4.50±1.50, more preferably 4.50±1.25, still more preferably 4.50±1.00, yet more preferably 4.50±0.75, most preferably 4.50±0.50 and in particular 4.50±0.25. In yet another preferred embodiment, the acid contains at least one acidic functional group having a $pK_A$ value within the range of 4.75±1.50, more preferably 4.75±1.25, still more preferably 4.75±1.00, yet more preferably 4.75±0.75, most preferably 4.75±0.50 and in particular 4.75±0.25. In yet another preferred embodiment, the acid contains at least one acidic functional group having a $pK_A$ value within the range of 5.00±1.50, more preferably 5.00±1.25, still more preferably 5.00±1.00, yet more preferably 5.00±0.75, most preferably 5.00±0.50 and in particular 5.00±0.25.

Preferably, the acid is an organic carboxylic or sulfonic acid, particularly a carboxylic acid. Multicarboxylic acids and/or hydroxy-carboxylic acids are especially preferred.

In case of multicarboxylic acids, the partial salts thereof are also to be regarded as multicarboxylic acids, e.g. the partial sodium, potassium or ammonium salts. For example, citric acid is a multicarboxylic acid having three carboxyl groups. As long as there remains at least one carboxyl group protonated (e.g. sodium dihydrogen citrate or disodium hydrogen citrate), the salt is to be regarded as a multicarboxylic acid. Preferably, however, all carboxyl groups of the multicarboxylic acid are protonated.

Preferably, the acid is of low molecular weight, i.e., not polymerized. Typically, the molecular weight of the acid is below 500 g/mol.

Examples of acids include saturated and unsaturated monocarboxylic acids, saturated and unsaturated bicarboxylic acids, tricarboxylic acids, α-hydroxyacids and β-hydroxyacids of monocarboxylic acids, α-hydroxyacids and β-hydroxyacids of bicarboxylic acids, α-hydroxyacids and β-hydroxyacids of tricarboxylic acids, ketoacids, α-ketoacids, β-ketoacids, of the polycarboxylic acids, of the polyhydroxy monocarboxylic acids, of the polyhydroxy bicarboxylic acids, of the polyhydroxy tricarboxylic acids.

Preferably, the acid is selected from the group consisting of benzenesulfonic acid, citric acid, α-glucoheptonic acid, D-gluconic acid, glycolic acid, lactic acid, malic acid, malonic acid, mandelic acid, propanoic acid, succinic acid, tartaric acid (d, l, or dl), tosic acid (toluene-sulfonic acid), valeric acid, palmitic acid, pamoic acid, sebacic acid, stearic acid, lauric acid, acetic acid, adipic acid, glutaric acid, 4-chlorobenzenesulfonic acid, ethanedisulfonic acid, ethylsuccinic acid, fumaric acid, galactaric acid (mucic acid), D-glucuronic acid, 2-oxo-glutaric acid, glycerophosphoric acid, hippuric acid, isethionic acid (ethanolsulfonic acid), lactobionic acid, maleic acid, maleinic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, methanesulfonic acid, nicotinic acid, orotic acid, oxalic acid, picric acid, L-pyroglutamic acid, saccharine, salicylic acid, gentisic acid, and/or 4-acetamidobenzoic acid.

Preferably, the acid is a multicarboxylic acid. More preferably, the multicarboxylic acid is selected from the group consisting of citric acid, maleic acid and fumaric acid.

Citric acid is particularly preferred.

The multicarboxylic acid, preferably citric acid, may be present in its anhydrous form or as a solvate and hydrate, respectively, e.g., as monohydrate.

If a free physiologically acceptable acid is contained in the pharmaceutical dosage form, it is preferably present in an amount of at most 5.0 wt.-%, preferably at most 2.5 wt.-%, more at most 2.0 wt.-%, at most 1.5 wt.-%, most preferably at most 1.0 wt.-% and in particular at most 0.9 wt.-%, based on the total weight of the pharmaceutical dosage form.

The pharmaceutical dosage form according to the invention may also contain a natural, semi-synthetic or synthetic wax. Waxes with a softening point of at least 50° C., more preferably 60° C. are preferred. Carnauba wax and beeswax are particularly preferred, especially carnauba wax.

Preferably, the pharmaceutical dosage form according to the invention contains a coating, preferably a film-coating. Suitable coating materials are known to the skilled person. Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), ethylcellulose (EC), cellulose acetate phthalate (CAP), hydroxypropylmethylcellulose phthalate (HPMCP); poly(meth)acrylates, such as aminoalkylmethacrylate copolymers, ethylacrylate methylmethacrylate copolymers, methacrylic acid methylmethacrylate copolymers, methacrylic acid methylmethacrylate copolymers; vinyl polymers, such as polyvinylpyrrolidone, polyvinyl-acetatephthalate, polyvinyl alcohol, polyvinylacetate; and natural film formers, such as shellack.

In a particularly preferred embodiment, the coating is water-soluble. In a preferred embodiment, the coating is based on polyvinyl alcohol, such as polyvinyl alcohol-part. hydrolyzed, and may additionally contain polyethylene glycol, such as macrogol 3350, and/or pigments. In another preferred embodiment, the coating is based on hydroxypropylmethylcellulose, preferably hypromellose type 2910 having a viscosity of 3 to 15 mPas.

The coating of the pharmaceutical dosage form can increase its storage stability.

The coating can be resistant to gastric juices and dissolve as a function of the pH value of the release environment. By means of this coating, it is possible to ensure that the pharmaceutical dosage form according to the invention passes through the stomach undissolved and the active compound is only released in the intestines. The coating which is resistant to gastric juices preferably dissolves at a pH value of between 5 and 7.5. Corresponding materials and methods for the delayed release of active compounds and for the application of coatings which are resistant to gastric juices are known to the person skilled in the art, for example from "Coated Pharmaceutical dosage forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers.

The pharmaceutical dosage form according to the invention is preferably tamper-resistant. Preferably, tamper-resistance is achieved based on the mechanical properties of the pharmaceutical dosage form so that comminution is avoided or at least substantially impeded. According to the invention, the term comminution means the pulverization of the pharmaceutical dosage form using conventional means usually available to an abuser, for example a pestle and mortar, a hammer, a mallet or other conventional means for pulverizing under the action of force. Thus, tamper-resistance preferably means that pulverization of the pharmaceutical dosage form using conventional means is avoided or at least substantially impeded.

Preferably, the mechanical properties of the pharmaceutical dosage form according to the invention, particularly its breaking strength, substantially rely on the presence and spatial distribution of the anionic polymer and the nonionic surfactant, although its/their mere presence does typically not suffice in order to achieve said properties. The advantageous mechanical properties of the pharmaceutical dosage form according to the invention may not automatically be achieved by simply processing pharmacologically active compound, anionic polymer, and optionally further excipients, such as the nonionic surfactant, by means of conventional methods for the preparation of pharmaceutical dosage forms. In fact, usually suitable apparatuses must be selected for the preparation and critical processing parameters must be adjusted, particularly pressure/force, temperature and time. Thus, even if conventional apparatuses are used, the process protocols usually must be adapted in order to meet the required criteria.

Furthermore, tamper-resistance is achieved based on the poor solubility properties of the pharmaceutical dosage form in alcohol, especially ethanol, thereby effectively preventing alcohol dose dumping.

The purpose of the anionic polymer that is contained in the pharmaceutical dosage form according to the invention is associated with the tamper resistance of the pharmaceutical dosage form, especially when the pharmaceutical dosage form is intended by an abuser for administration by a non-prescribed route, particularly intravenous administration of a liquid extract.

In a preferred embodiment, when
subjecting a pharmaceutical dosage form (a) for 5 minutes in 5 mL of cold water, or (b) to boiling water and boiling the tablet for 5 minutes, respectively,
closing the vessel with aluminum foil, boiling extraction only,
drawing up the liquid into a syringe using a cannula, preferably 0.80×40 mm BULB; 21 G×1½", through a cigarette filter, and
determining the pharmacologically active compound content in the drawn liquid by HPLC analysis;
the content of extracted pharmacologically active compound in the overhead liquid amounts to at most 14.5 wt.-%, 14.0 wt.-%, 13.5 wt.-%, or 13.0 wt.-%, more preferably at most 12.5 wt.-%, 12.0 wt.-%, 11.5 wt.-%, or 11.0 wt.-%, still more preferably at most 10.5 wt.-%, 10 wt.-%, 9.5 wt.-%, or 9.0 wt.-%, yet more preferably at most 8.5 wt.-%, 8.0 wt.-%, 7.5 wt.-%, or 7.0 wt.-%, even more preferably at most 6.5 wt.-%, 6.0 wt.-%, 5.5 wt.-%, or 5.0 wt.-%, most more preferably at most 4.5 wt.-%, 4.0 wt.-%, 3.5 wt.-%, or 3.0 wt.-%, and in particular at most 2.5 wt.-%, 2.0 wt.-%, 1.5 wt.-%, or 1.0 wt.-%, relative to the original total content of the pharmacologically active compound in the pharmaceutical dosage form, i.e. before it was subjected to the extraction test.

In a preferred embodiment, when
subjecting a pharmaceutical dosage form (a) for 5 minutes in 5 mL of cold water, or (b) to boiling water and boiling the pharmaceutical dosage form for 5 minutes, respectively,
closing the vessel with aluminum foil, boiling extraction only,
drawing up the liquid into a 10 mL syringe using a cannula, preferably 0.80×40 mm BL/LB; 21 G×1½", through a cigarette filter, and
determining the pharmacologically active compound content in the drawn liquid by HPLC analysis.
the total amount of extracted pharmacologically active compound in the overhead liquid amounts to
at most 115 mg, 110 mg, 105 mg, or 100 mg, more preferably at most 95 mg, 90 mg, 85 mg, or 80 mg, still more preferably at most 75 mg, 70 mg, 65 mg, or 60 mg, yet more preferably at most 55 mg, 50 mg, 47.5 mg, or 45 mg, even more preferably at most 42.5 mg, 40 mg, 37.5 mg, or 35 mg, most more preferably at most 32.5 mg, 30 mg, 27.5 mg, or 25 mg, and in particular at most 22.5 mg, 20 mg, 17.5 mg, or 15 mg; or
at most 14.5 mg, 14.0 mg, 13.5 mg, or 13.0 mg, more preferably at most 12.5 mg, 12.0 mg, 11.5 mg, or 11.0 mg, still more preferably at most 10.5 mg, 10 mg, 9.5 mg, or 9.0 mg, yet more preferably at most 8.5 mg, 8.0 mg, 7.5 mg, or 7.0 mg, even more preferably at most 6.5 mg, 6.0 mg, 5.5 mg, or 5.0 mg, most more preferably at most 4.5 mg, 4.0 mg, 3.5 mg, or 3.0 mg, and in particular at most 2.5 mg, 2.0 mg, 1.5 mg, or 1.0 mg.

In a preferred embodiment, when
subjecting a pharmaceutical dosage form (a) for 30 minutes to 30 mL of solvent with continuous shaking, or (b) giving a pharmaceutical dosage form in 30 mL of purified water, heating the water until boiling and shaking for 30 minutes, during the slow cooling of the water;
supplementing lost water, if any, and
determining the pharmacologically active compound content in the overhead liquid by HPLC analysis;
the content of extracted pharmacologically active compound in the overhead liquid amounts to at most 40 wt.-%, more preferably at most 35 wt.-%, still more preferably at most 30 wt.-%, yet more preferably at most 25 wt.-% or 24 wt.-%, even more preferably at most 23 wt.-%, 22 wt.-%, 21 wt.-% or 20 wt.-%, most preferably at most 19 wt.-%, 18 wt.-%, 17 wt.-%, or 16 wt.-%, and in particular at most 15.5 wt.-%, 15.0 wt.-%, 12 wt.-%, or 10 wt.-%, relative to the original total content of the pharmacologically active compound in the pharmaceutical dosage form, i.e. before it was subjected to the extraction test.

In a preferred embodiment, when
subjecting a pharmaceutical dosage form (a) for 30 minutes to 30 mL of solvent with continuous shaking, or (b) giving a pharmaceutical dosage form in 30 mL of purified water, heating the water until boiling and shaking for 30 minutes, during the slow cooling of the water;
supplementing lost water, if any, and
determining the pharmacologically active compound content in the overhead liquid by HPLC analysis;
the total amount of extracted pharmacologically active compound in the overhead liquid amounts to
at most 200 mg, 190 mg, 180 mg, or 170 mg, more preferably at most 160 mg, 150 mg, 140 mg, or 135 mg, still more preferably at most 130 mg, 125 mg, 120 mg, or 110 mg, yet more preferably at most 105 mg or 100 mg, even more preferably at most 95 mg or 90 mg, most more preferably at most 85 mg or 80 mg, and in particular at most 75 mg, 70 mg, 65 mg, or 60 mg; or
at most 55 mg, 50 mg, 47.5 mg, or 45 mg, more preferably at most 42.5 mg, 40 mg, 37.5 mg, or 35 mg, still more preferably at most 32.5 mg, 30 mg, 27.5 mg, or 25 mg, yet more preferably at most 22.5 mg or 20 mg, even more preferably at most 17.5 mg or 15 mg, most more preferably at most 14 mg or 13 mg, and in particular at most 12.5 mg, 12 mg, 11.5 mg, 11 mg, 10.5 mg or 10 mg.

Preferably, when a pharmaceutical dosage form according to the invention is treated with a commercial coffee mill, preferably type Bosch MKM6000, for 2 minutes, at least 40 wt.-%, more preferably at least 50 wt.-%, still more preferably at least 60 wt.-%, yet more preferably at least 65 wt.-%, even more preferably at least 70 wt.-%, most preferably at least 75 wt.-%, and in particular at least 80 wt.-%, of the total weight of the thus obtained material does not pass a sieve having a mesh size of 1.000 mm.

In a preferred embodiment, when a pharmaceutical dosage form according to the invention is treated with a commercial coffee mill, preferably type Bosch MKM6000, for 2 minutes, it either remains intact and in one piece, or it is split into at most 10, preferably at most 7 or 8, more preferably at most 5 or 6, still more preferably at most 4, most preferably at most 3, and in particular at most 2 pieces.

The pharmaceutical dosage form according to the invention has a breaking strength of at least 300 N, preferably at least 400 N, more preferably at least 500 N, still more preferably at least 750 N, yet more preferably at least 1000 N, most preferably at least 1250 N and in particular at least 1500 N.

The "breaking strength" (resistance to crushing) of a pharmaceutical dosage form is known to the skilled person. In this regard it can be referred to, e.g., W. A. Ritschel, Die Tablette, 2. Auflage, Editio Cantor Verlag Aulendorf, 2002; H Liebermann et al., Pharmaceutical dosage forms: Tablets, Vol. 2, Informa Healthcare; 2 edition, 1990; and Encyclopedia of Pharmaceutical Technology, Informa Healthcare; 1 edition.

For the purpose of the specification, the breaking strength is preferably defined as the amount of force that is necessary in order to fracture the pharmaceutical dosage form (=breaking force). Therefore, for the purpose of the specification the pharmaceutical dosage form does preferably not exhibit the desired breaking strength when it breaks, i.e., is fractured into at least two independent parts that are separated from one another. In another preferred embodiment, however, the pharmaceutical dosage form is regarded as being broken if the force decreases by 25% (threshold value) of the highest force measured during the measurement (see below).

The pharmaceutical dosage forms according to the invention are distinguished from conventional pharmaceutical dosage forms in that, due to their breaking strength, they cannot be pulverized by the application of force with conventional means, such as for example a pestle and mortar, a hammer, a mallet or other usual means for pulverization, in particular devices developed for this purpose (tablet crushers). In this regard "pulverization" means crumbling into small particles that would immediately release the pharmacologically active compound in a suitable medium. Avoidance of pulverization virtually rules out oral or parenteral, in particular intravenous or nasal abuse.

Conventional tablets typically have a breaking strength well below 200 N in any direction of extension. The breaking strength of conventional round tablets may be estimated according to the following empirical formula: Breaking Strength [in N]=10×Diameter Of The Tablet [in mm]. Thus, according to said empirical formula, a round tablet having a breaking strength of at least 300 N would require a diameter of at least 30 mm). Such a tablet, however, could not be swallowed. The above empirical formula preferably does not apply to the pharmaceutical dosage forms of the invention, which are not conventional but rather special.

Further, the actual mean chewing force is about 220 N (cf., e.g., P. A. Proeschel et al., J Dent Res, 2002, 81(7), 464-468). This means that conventional tablets having a breaking strength well below 200 N may be crushed upon spontaneous chewing, whereas the pharmaceutical dosage forms according to the invention may not.

Still further, when applying a gravitational acceleration of about 9.81 m/s$^2$, 300 N correspond to a gravitational force of more than 30 kg, i.e. the pharmaceutical dosage forms according to the invention can preferably withstand a weight of more than 30 kg without being pulverised.

Methods for measuring the breaking strength of a pharmaceutical dosage form are known to the skilled artisan. Suitable devices are commercially available.

For example, the breaking strength (resistance to crushing) can be measured in accordance with the Eur. Ph. 5.0, 2.9.8 or 6.0, 2.09.08 "Resistance to Crushing of Tablets". The test is intended to determine, under defined conditions, the resistance to crushing of tablets, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the tablet. The apparatus is calibrated using a system with a precision of 1 Newton. The tablet is placed between the jaws, taking into account, where applicable, the shape, the break-mark and the inscription; for each measurement the tablet is oriented in the same way with respect to the direction of application of the force (and the direction of extension in which the breaking strength is to be measured). The measurement is carried out on 10 tablets, taking care that all fragments of tablets have been removed before each determination. The result is expressed as the mean, minimum and maximum values of the forces measured, all expressed in Newton.

A similar description of the breaking strength (breaking force) can be found in the USP. The breaking strength can alternatively be measured in accordance with the method described therein where it is stated that the breaking strength is the force required to cause a tablet to fail (i.e., break) in a specific plane. The tablets are generally placed between two platens, one of which moves to apply sufficient force to the tablet to cause fracture. For conventional, round (circular cross-section) tablets, loading occurs across their diameter (sometimes referred to as diametral loading), and fracture occurs in the plane. The breaking force of tablets is commonly called hardness in the pharmaceutical literature; however, the use of this term is misleading. In material science, the term hardness refers to the resistance of a surface to penetration or indentation by a small probe. The term crushing strength is also frequently used to describe the resistance of tablets to the application of a compressive load. Although this term describes the true nature of the test more accurately than does hardness, it implies that tablets are actually crushed during the test, which is often not the case.

In a preferred embodiment of the invention, the breaking strength (resistance to crushing) is measured in accordance with WO 2005/016313, WO 2005/016314, and WO 2006/082099, which can be regarded as a modification of the method described in the Eur. Ph. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. Measurement is performed using a pressure piston with screw-in inserts and a cylinder (diameter 10 mm), a force transducer, $F_{max}$. 1 kN, diameter=8 mm, class 0.5 from 10 N, class 1 from 2 N to ISO 7500-1, with manufacturers test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centring device.

In another preferred embodiment of the invention, the breaking strength is measured by means of a breaking strength tester e.g. Sotax®, type HT100 or type HT1 (Allschwil, Switzerland). Both, the Sotax® HT100 and the Sotax® HT1 can measure the breaking strength according to two different measurement principles: constant speed (where the test jaw is moved at a constant speed adjustable from 5-200 mm/min) or constant force (where the test jaw increases force linearly adjustable from 5-100 N/sec). In principle, both measurement principles are suitable for measuring the breaking strength of the pharmaceutical dosage form according to the invention. Preferably, the breaking strength is measured at constant speed, preferably at a constant speed of 120 mm/min.

In a preferred embodiment, the pharmaceutical dosage form is regarded as being broken if it is fractured into at least two separate pieces.

The pharmaceutical dosage form according to the invention preferably exhibits mechanical strength over a wide temperature range, in addition to the breaking strength (resistance to crushing) optionally also sufficient hardness, impact resistance, impact elasticity, tensile strength and/or modulus of elasticity, optionally also at low temperatures (e.g. below −24° C., below −40° C. or in liquid nitrogen), for it to be virtually impossible to pulverize by spontaneous chewing, grinding in a mortar, pounding, etc. Thus, preferably, the comparatively high breaking strength of the pharmaceutical dosage form according to the invention is maintained even at low or very low temperatures, e.g., when the pharmaceutical dosage form is initially chilled to increase its brittleness, for example to temperatures below −25° C., below −40° C. or even in liquid nitrogen.

The pharmaceutical dosage form according to the invention is characterized by a certain degree of breaking strength. This does not mean that the pharmaceutical dosage form must also exhibit a certain degree of hardness. Hardness and breaking strength are different physical properties. Therefore, the tamper resistance of the pharmaceutical dosage form does not necessarily depend on the hardness of the pharmaceutical dosage form. For instance, due to its breaking strength, impact strength, elasticity modulus and tensile strength, respectively, the pharmaceutical dosage form can preferably be deformed, e.g. plastically, when exerting an external force, for example using a hammer, but cannot be pulverized, i.e., crumbled into a high number of fragments. In other words, the pharmaceutical dosage form according to the invention is characterized by a certain degree of breaking strength, but not necessarily also by a certain degree of form stability.

Therefore, in the meaning of the specification, a pharmaceutical dosage form that is deformed when being exposed to a force in a particular direction of extension but that does not break (plastic deformation or plastic flow) is preferably to be regarded as having the desired breaking strength in said direction of extension.

Preferably, the pharmaceutical dosage form according to the invention
- has a breaking strength of at least 400 N, more preferably at least 500 N, still more preferably at least 750 N, and most preferably at least 1000 N; and/or
- comprises a pharmacologically active compound selected from opioids, more preferably from hydromorphone, oxycodone, oxymorphone, tapentadol and the physiologically acceptable salts thereof; and/or
- comprises an anionic polymer derived from a monomer composition comprising an ethylenically unsaturated monomer selected from (alk)acrylic acids, (alk)acrylic anhydrides, alkyl (alk)acrylates, or a combination thereof, in particular acrylic acid, and optionally at least one cross-linking agent selected from the group consisting of allyl sucrose, allyl pentaerythritol, divinyl glycol, divinyl polyethylene glycol and (meth)acrylic acid esters of diols; and/or
- comprises the anionic polymer in an amount of at least 25 wt.-%, preferably at least 30 wt.-% or at least 32 wt.-%, based on the total weight of the pharmaceutical dosage form; and/or
- comprises a nonionic surfactant,
    (i) preferably a copolymer of ethylene oxide and propylene oxide, more preferably a block copolymer according to general formula (I-a)

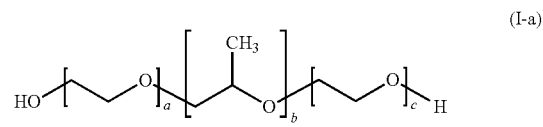

(I-a)

wherein a and c are each independently an integer of from 5 to 300 and b is an integer of from 10 to 100; and/or a block copolymer according to general formula (I-b)

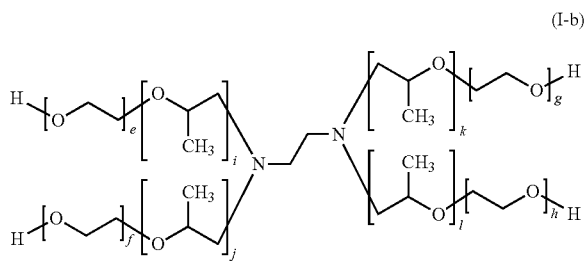

(I-b)

wherein e, f, g and h are each independently an integer of from 1 to 150, and i, j, k and l are each independently an integer of from 2 to 50;

(ii) which is preferably contained in the pharmaceutical dosage form in an amount of at least 10 wt.-%, more preferably at least 15 wt.-%, and most preferably 15 to 40 wt.-%, based on the total weight of the pharmaceutical dosage form; and/or (iii) which preferably exhibits an HLB value of at least 20, more preferably at least 24; and/or is configured for oral administration, preferably one daily or twice daily; and/or either does not contain any polyalkylene oxide having an average molecular weight of at least 200,000 g/mol, preferably of at least 50,000 g/mol; or wherein the total content of polyalkylene oxide(s) having an average molecular weight of at least 200,000 g/mol or at least 50,000 g/mol, respectively, is ≤20 wt.-%, preferably ≤10 wt.-%, based on the total weight of the pharmaceutical dosage form; and/or optionally, contains a plasticizer, preferably polyethylene glycol; and/or optionally, contains an additional matrix polymer, preferably a cellulose ether, more preferably HPMC.

The pharmaceutical dosage form according to the invention may be produced by different processes, the particularly preferred of which are explained in greater detail below. Several suitable processes have already been described in the prior art. In this regard it can be referred to, e.g., WO 2005/016313, WO 2005/016314, WO 2005/063214, WO 2005/102286, WO 2006/002883, WO 2006/002884, WO 2006/002886, WO 2006/082097, and WO 2006/082099.

The invention also relates to pharmaceutical dosage forms that are obtainable by any of the processes described here below.

In general, the process for the production of the pharmaceutical dosage form according to the invention preferably comprises the following steps:
(a) mixing all ingredients;
(b) optionally pre-forming the mixture obtained from step (a), preferably by applying heat and/or force to the mixture obtained from step (a), the quantity of heat supplied preferably not being sufficient to heat the matrix material up to its softening point;
(c) hardening the mixture by applying heat and force, it being possible to supply the heat during and/or before the application of force and the quantity of heat supplied being sufficient to heat the matrix material at least up to its softening point;
(d) optionally singulating the hardened mixture;
(e) optionally shaping the pharmaceutical dosage form; and
(f) optionally providing a film coating.

Heat may be supplied directly, e.g. by contact or by means of hot gas such as hot air, or with the assistance of ultrasound, microwaves and/or radiation. Force may be applied and/or the pharmaceutical dosage form may be shaped for example by direct tabletting or with the assistance of a suitable extruder, particularly by means of a screw extruder equipped with two screws (twin-screw-extruder) or by means of a planetary gear extruder.

The final shape of the pharmaceutical dosage form may either be provided during the hardening of the mixture by applying heat and force (step (c)) or in a subsequent step (step (e)). In both cases, the mixture of all components is preferably in the plastified state, i.e. preferably, shaping is performed at a temperature at least above the softening point of the matrix material. However, extrusion at lower temperatures, e.g. ambient temperature, is also possible and may be preferred.

Shaping can be performed, e.g., by means of a tabletting press comprising die and punches of appropriate shape.

A particularly preferred process for the manufacture of the pharmaceutical dosage form of the invention involves hot-melt extrusion. In this process, the pharmaceutical dosage form according to the invention is produced by thermoforming with the assistance of an extruder, preferably without there being any observable consequent discoloration of the extrudate. It has been surprisingly found that acid is capable of suppressing discoloration. In the absence of acid, the extrudate tends to develop beige to yellowish coloring whereas in the presence of acid the extrudates are substantially colorless, i.e. white.

This process is characterized in that
a) all components are mixed,
b) the resultant mixture is heated in the extruder at least up to the softening point of the matrix material and extruded through the outlet orifice of the extruder by application of force,
c) the still plastic extrudate is singulated and formed into the pharmaceutical dosage form or
d) the cooled and optionally reheated singulated extrudate is formed into the pharmaceutical dosage form.

Mixing of the components according to process step a) may also proceed in the extruder.

The components may also be mixed in a mixer known to the person skilled in the art. The mixer may, for example, be a roll mixer, shaking mixer, shear mixer or compulsory mixer.

The, preferably molten, mixture which has been heated in the extruder at least up to the softening point of matrix material is extruded from the extruder through a die with at least one bore.

The process according to the invention requires the use of suitable extruders, preferably screw extruders. Screw extruders which are equipped with two screws (twin-screw-extruders) are particularly preferred.

The extrusion is preferably performed so that the expansion of the strand due to extrusion is not more than 30%, i.e. that when using a die with a bore having a diameter of e.g. 6 mm, the extruded strand should have a diameter of not more than 8 mm. More preferably, the expansion of the strand is not more than 25%, still more preferably not more than 20%, most preferably not more than 15% and in particular not more than 10%.

Preferably, extrusion is performed in the absence of water, i.e., no water is added. However, traces of water (e.g., caused by atmospheric humidity) may be present.

The extruder preferably comprises at least two temperature zones, with heating of the mixture at least up to the softening point of the matrix material proceeding in the first zone, which is downstream from a feed zone and optionally mixing zone. The throughput of the mixture is preferably from 1.0 kg to 15 kg/hour. In a preferred embodiment, the throughput is from 1 to 3.5 kg/hour. In another preferred embodiment, the throughput is from 4 to 15 kg/hour.

In a preferred embodiment, the die head pressure is within the range of from 2 to 100 bar. In a preferred embodiment, the die head pressure is within the range of from 25 to 100 bar. In another preferred embodiment, the die head pressure is within the range of from 2 to 25 bar. The die head pressure can be adjusted inter alia by die geometry, temperature profile and extrusion speed.

The die geometry or the geometry of the bores is freely selectable. The die or the bores may accordingly exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of the matrix material and does not rise above a temperature at which the pharmacologically active compound to be processed may be damaged. Preferably, the temperature of the mixture to be extruded is adjusted to below 180° C., preferably below 150° C., but at least to the softening temperature of matrix material. Typical extrusion temperatures are 120° C. and 130° C.

In a preferred embodiment, the extruder torque is within the range of from 30 to 95%. Extruder torque can be adjusted inter alia by die geometry, temperature profile and extrusion speed.

After extrusion of the molten mixture and optional cooling of the extruded strand or extruded strands, the extrudates are preferably singulated. This singulation may preferably be performed by cutting up the extrudates by means of revolving or rotating knives, water jet cutters, wires, blades or with the assistance of laser cutters.

Preferably, intermediate or final storage of the optionally singulated extrudate or the final shape of the pharmaceutical dosage form according to the invention is performed under oxygen-free atmosphere which may be achieved, e.g., by means of oxygen-scavengers.

The singulated extrudate may be press-formed into tablets in order to impart the final shape to the pharmaceutical dosage form.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a pharmaceutical dosage form with desired mechanical properties, may be established by simple preliminary testing.

For example but not limiting, extrusion may be performed by means of a twin-screw-extruder type ZSE 18 or ZSE27 (Leistritz, Nurnberg, Germany), screw diameters of 18 or 27 mm. Screws having eccentric ends may be used. A heatable die with a round bore having a diameter of 4, 5, 6, 7, 8, 9, or 10 mm may be used. The extrusion parameters may be adjusted e.g. to the following values: rotational speed of the screws: 120 Upm; delivery rate 2 kg/h for a ZSE 18 or 8 kg/h for a ZSE27; product temperature: in front of die 125° C.; temperature of the die 135° C.; and jacket temperature: 110° C.

Preferably, extrusion is performed by means of twin-screw-extruders or planetary-gear-extruders, twin-screw extruders (co-rotating or contra-rotating) being particularly preferred.

The pharmaceutical dosage form according to the invention is preferably produced by thermoforming with the assistance of an extruder without any observable consequent discoloration of the extrudates.

The process for the preparation of the pharmaceutical dosage form according to the invention is preferably performed continuously. Preferably, the process involves the extrusion of a homogeneous mixture of all components. It is particularly advantageous if the thus obtained intermediate, e.g. the strand obtained by extrusion, exhibits uniform properties. Particularly desirable are uniform density, uniform distribution of the active compound, uniform mechanical properties, uniform porosity, uniform appearance of the surface, etc. Only under these circumstances the uniformity of the pharmacological properties, such as the stability of the release profile, may be ensured and the amount of rejects can be kept low.

A further aspect of the invention relates to the use of a pharmacologically active compound in combination with an anionic polymer for the manufacture of the pharmaceutical dosage form as described above for the treatment of pain, preferably moderate to severe pain such as moderate to severe low back pain.

A further aspect of the invention relates to the use of a pharmaceutical dosage form as described above for avoiding or hindering the abuse of the pharmacologically active compound contained therein.

A further aspect of the invention relates to the use of a pharmaceutical dosage form as described above for avoiding or hindering the unintentional overdose of the pharmacologically active compound contained therein.

In this regard, the invention also relates to the use of a pharmacologically active compound as described above and/or an anionic polymer as described above for the manufacture of the pharmaceutical dosage form according to the invention for the prophylaxis and/or the treatment of a disorder, thereby preventing an overdose of the pharmacologically active compound, particularly due to comminution of the pharmaceutical dosage form by mechanical action.

Further, the invention relates to a method for the prophylaxis and/or the treatment of a disorder comprising the administration of the pharmaceutical dosage form according to the invention, thereby preventing an overdose of the pharmacologically active compound, particularly due to comminution of the pharmaceutical dosage form by mechanical action. Preferably, the mechanical action is selected from the group consisting of chewing, grinding in a mortar, pounding, and using apparatuses for pulverizing conventional pharmaceutical dosage forms.

The following examples further illustrate the invention but are not to be construed as limiting its scope.

General Procedure:

Carbopol 71 G, tramadol hydrochloride and all other excipients were weighted and sieved to each other.

The powder was mixed and dosed gravimetrically to an extruder. Hot-melt extrusion (revolution speed 100 rpm) was performed by means of a twin screw extruder of type ZSE27 micro PH 40D (Leistritz, Nurnberg, Germany) that was equipped with a heatable round die having a diameter of 10 mm (cutting length 6-7 mm or 7-8 mm).

The hot extrudate was cooled by ambient air and the cooled extrusion strand was comminuted to cut pieces. The cut pieces were shaped by means of an excenter press which was equipped with a round punch.

The breaking strength of the pharmaceutical dosage forms was measured by means of a Sotax® HT100. A tablet was regarded as failing the breaking strength test when during the measurement the force dropped below the threshold value of 25% of the maximum force that was observed during the measurement, regardless of whether the pharmaceutical dosage form was fractured into separate pieces or not. All values are given as a mean of 10 measurements.

The in vitro release profile of tramadol hydrochloride was measured in 600 ml phosphate buffer (pH 6.8) at temperature of 37° C. with sinker (type 1 or 2). The rotation speed of the paddle was adjusted to 75/min.

EXAMPLE 1 a) Composition

Tablets having the following compositions were prepared:

|  | I-1 | | I-2 | I-3 | | I-4 | |
|---|---|---|---|---|---|---|---|
|  | mg | wt.-% | mg | mg | wt.-% | mg | wt.-% |
| Tramadol HCl | 80.0 | 13.3 | 80.0 | 80.0 | 13.3 | 80.0 | 13.3 |
| Carbopol 71 G | 185.0 | 30.85 | 185.0 | 222.0 | 37.0 | 222.0 | 37.0 |
| Poloxamer 407 (Lutrol® F127) | 185.0 | 30.85 | — | 148.0 | 24.7 | — | — |
| Poloxamer 188 (Lutrol® F68) | — | — | 185.0 | 30.85 | — | — | 148.0 | 24.7 |
| HPMC 100,000 mPa · s | 60.0 | 10.0 | 60.0 | 60.0 | 10.0 | 60.0 | 10.0 |
| Macrogol 6,000 | 90.0 | 15.0 | 90.0 | 90.0 | 15.0 | 90.0 | 15.0 |
| Σ | 600.0 | 100.0 | 600.0 100.0 | 600.0 | 100.0 | 600.0 | 100.0 |

|  | C-1 | |
|---|---|---|
|  | mg | wt.-% |
| Tramadol HCl | 80.0 | 13.3 |
| Polyethylene Oxide $M_w$ $7 \times 10^6$ | 370.0 | 61.7 |
| HPMC 100,000 mPa · s | 60.0 | 10.0 |
| Macrogol 6,000 | 90.0 | 15.0 |
| Σ | 600.0 | 100.0 | b) Hot-Melt Extrusion

The following extrusion parameters were adjusted and measured, respectively:

|  | I-1 | I-2 | I-3 | I-4 | C-1 |
|---|---|---|---|---|---|
| diameter of die [mm] | 10 | 10 | 10 | 10 | 10 |
| throughput [kg/h] | 3.5 | 3.5 | 3.5 | 3.5 | 3.5 |
| melt temperature [° C.] | 116 | 115 | 117 | 115 | 98 |
| performance (%) | 21 | 22 | 45 | 49 | 54 |
| melt pressure [bar] | 3 | 5 | 8 | 12 | 42 |
| strand diameter [mm] | 10.3 | 12.2 | 10.5 | 10.5 | 9.9 |
| cutting length [mm] | 7.1-7.4 | 7.0-8.5 | 6.5-6.8 | 6-7 | 7.5 |

Crude extrudates having the following weights and dimensions were obtained:

| n = 10 | | I-1 | I-2 | I-3 | I-4 | C-1 |
|---|---|---|---|---|---|---|
| weight [mg] | min | 584 | 578 | 577 | 575 | 599 |
|  | max | 629 | 628 | 624 | 625 | 627 |
|  | average | 612 | 597 | 602 | 609 | 613 |
| length [mm] | min | 6.95 | 6.39 | 6.30 | 6.52 | 6.45 |
|  | max | 7.46 | 7.01 | 7.33 | 7.40 | 7.54 |
|  | average | 7.26 | 6.68 | 6.66 | 6.94 | 7.12 |
| diameter [mm] | min | 9.16 | 10.32 | 9.21 | 9.86 | 9.73 |
|  | max | 10.75 | 11.25 | 11.11 | 10.92 | 10.12 |
|  | average | 9.75 | 10.79 | 10.33 | 10.44 | 9.97 | c) Formation of Tablets from Extrudates

Tablets were manufactured from the crude extrudates by means of a round punch having the following dimensions (no engraving):

| Example | Form of punch |
|---|---|
| round | biconcave, round, diameter 12 mm, radius of curvature 9 mm |

Tablets having the following weights and dimensions were obtained:

| n = 10 | | I-1 | I-2 | I-3 | I-4 | C-1 |
|---|---|---|---|---|---|---|
| thickness [mm] | min | 6.61 | 6.31 | 6.08 | 6.17 | 6.27 |
|  | max | 6.87 | 6.55 | 6.79 | 6.70 | 6.81 |
|  | average | 6.72 | 6.43 | 6.43 | 6.41 | 6.53 |
| diameter [mm] | min | 11.68 | 11.61 | 11.46 | 11.35 | 11.56 |
|  | max | 12.03 | 12.09 | 12.05 | 11.98 | 11.86 |
|  | average | 11.90 | 11.90 | 11.67 | 11.66 | 11.71 | d) In-Vitro Release

| measuring point Dissolution % (DS) | I-1 | I-2 | I-3 | I-4 | C-1 |
|---|---|---|---|---|---|
| after 60 min | 13 | 14 | 16 | 16 | 21 |
| after 120 min | 20 | 22 | 25 | 25 | 33 |
| after 480 min | 46 | 51 | 57 | 57 | 76 |
| after 720 min | 59 | 64 | 73 | 75 | 90 |
| after 1440 min | 82 | 88 | 94 | 100 | 101 |

-continued

| measuring point Dissolution % (0.1N HCl) | I-1 | I-2 | I-3 | I-4 | C-1 |
|---|---|---|---|---|---|
| after 60 min | 19 | 19 | 16 | 18 | 20 |
| after 120 min | 27 | 28 | 24 | 26 | 31 |
| after 480 min | 56 | 60 | 51 | 58 | 78 |
| after 720 min | 68 | 75 | 65 | 73 | 95 |
| after 1440 min | 90 | 95 | 90 | 95 | 102 | e) Tamper Resistance—Breaking Strength

| breaking strength [N] | I-1 | I-2 | I-3 | I-4 | C-1 |
|---|---|---|---|---|---|
| Sotax ® HT100 | 318N | 877N | ≥1000N | ≥1000N | ≥1000N |

The corresponding force-displacement diagrams of examples I-1, I-2, I-3, I-4 and C are displayed as FIGS. 1-A, 1-B, 1-C, 1-D and 1-E, respectively.

The deviating curve in FIG. 1-C represents a measurement error (tablet displaced).

f) Tamper Resistance—Extractability

The extractable content of pharmacologically active compound was determined by
  (i) subjecting a tablet (a) for 30 minutes to 30 mL of solvent with continuous shaking, or (b) giving a tablet in 30 mL of purified water, heating the water until boiling and shaking for 30 minutes, during the slow cooling of the water;
  (ii) supplementing lost water, if any, and
  (iii) determining the pharmacologically active compound content in the overhead liquid by HPLC analysis.

The syringeable content of pharmacologically active compound was determined by
  (i) subjecting a tablet (a) for 5 minutes in 5 mL of cold water, or (b) to boiling water and boiling the tablet for 5 minutes, respectively,
  (ii) closing the vessel with aluminum foil, boiling extraction only,
  (iii) drawing up the liquid into a syringe using a cannula through a cigarette filter, and
  (iv) determining the pharmacologically active compound content in the drawn liquid by HPLC analysis.

The results are shown in the table here below:

| content [wt.-%] | I-1 | I-2 | I-3 | I-4 | C-1 |
|---|---|---|---|---|---|
| faultless tablet | 90.4 | 95.7 | 94.7 | 95.8 | 99.6 |
| extraction cold water | 9.7 | 9.9 | 8.6 | 9.3 | 13.9 |
| extraction boiling water | 18.6 | 21.5 | 15.1 | 14.9 | 25.7 |
| extraction water/ethanol 60/40 v/v | 8.4 | 8.3 | 8.6 | 9.6 | 9.4 |
| drawn up into syringe (faultless tablet) | 2.9 | 10.8 | 3.2 | 6.8 | 2.6 |
| drawn up into syringe (ground tablet)[1] | 8.1 | 7.2 | 3.4 | 5.5 | 10.8 |

[1]household coffee mill, type Bosch MKM6000, 180 W, type KM 13; grinding time: 2 minutes g) Tamper Resistance—Hammer Impact The test was performed by means of a free falling weight testing device Type 40-550-001, 40-550-011 ff, Coesfeld GmbH & Co. KG, Germany. The following parameters were set:
  Falling height: 1000 mm±1%
  Falling weight: 500 g±2%
  Form of falling weight: 25 mm×25 mm
  Position of sample: loosely positioned in the center of the sample holder The measuring result was qualified according to the following scale:
  (A) tablet apparently undamaged
  (B) tablet has been compressed but is widely undamaged
  (C) tablet has been compressed and is lacerated at its edges
  (D) tablet has been disrupted into several pieces
  (E) tablet has been pulverized The results are shown in the table here below:

| I-1 | I-2 | I-3 | I-4 | C-1 |
|---|---|---|---|---|
| (D) | (D) | (D) | (C) | (A) | h) Tamper Resistance—Grindability

The tablets were treated by means of o commercially available household coffee mill, type Bosch MKM6000 (180 W, type KM 13). Subsequently, the thus obtained material was analyzed by means of a sieving tower (Haver & Boecker, analysis sieve, diameter: 50 mm) equipped with a bottom plate, displacement ring, lid, and 14 sieves the mesh sizes ranging from 0.045 mm to 4.000 mm, namely 0.045 mm; 0.063 mm; 0.090 mm; 0.125 mm; 0.180 mm; 0.250 mm; 0.355 mm; 0.500 mm; 0.710 mm; 1.000 mm; 1.400 mm; 2.000 mm; 2.800 mm; 4.000 mm. The amplitude was set to 1.5 mm. Sieving time was 10 min.

The results after 2 minutes grinding are summarized in the table here below:

| 2 min grinding time | I-1 | I-2 | I-3 | I-4 | C-1 |
|---|---|---|---|---|---|
| <0.045 | 0.00 | 0.00 | 0.00 | 0.00 | 0.00 |
| 0.045-0.063 | 0.00 | 0.00 | 0.00 | 0.00 | 0.00 |
| 0.063-0.090 | 0.00 | 0.00 | 0.00 | 0.00 | 0.00 |
| 0.090-0.125 | 0.57 | 0.00 | 0.00 | 0.00 | 0.00 |
| 0.125-0.180 | 0.57 | 0.00 | 0.00 | 0.00 | 0.00 |
| 0.180-0.250 | 4.14 | 1.20 | 1.27 | 1.60 | 0.00 |
| 0.250-0.355 | 9.05 | 5.84 | 4.69 | 1.60 | 1.42 |
| 0.355-0.500 | 12.82 | 10.48 | 7.04 | 3.78 | 1.42 |
| 0.500-0.710 | 16.81 | 14.09 | 12.26 | 5.48 | 3.72 |
| 0.710-1.000 | 15.72 | 15.29 | 14.05 | 7.18 | 6.56 |
| 1.000-1.400 | 15.20 | 19.45 | 15.26 | 11.00 | 14.54 |
| 1.400-2.000 | 12.53 | 16.17 | 17.24 | 16.47 | 27.42 |
| 2.000-2.800 | 7.44 | 9.27 | 19.45 | 12.59 | 16.60 |
| 2.800-4.000 | 2.96 | 8.20 | 6.09 | 12.32 | 16.97 |
| >4.000 | 2.19 | 0.00 | 2.65 | 28.00 | 11.35 |

It is clear from the above data that the dosage forms according to the invention have advantages compared to the reference with respect to extractability in cold and hot water. At the same time, breaking strength, impact resistance and indifference of the release profile to pH changes of some preferred dosage forms according to the invention are comparable to those of the reference.

EXAMPLE 2

Tablets having a total weight of 600 mg were manufactured in analogy to example 1. The breaking strength (measured in accordance with WO 2005/016313, WO 2005/016314, and WO 2006/082099) of the tablets was measured (average value, n=3). The compositions and the measured breaking strengths are summarized in the table here below:

| ex. | breaking strength [N] | CBP:LUT | (CBP + LUT): PEG | CBP: PEG | LUT: PEG | (CBP + LUT): HPMC | API: (CBP + LUT) | API: CBP | API: LUT |
|---|---|---|---|---|---|---|---|---|---|
| 2-1 | 565 | 1.0 | 4.0 | 2.0 | 2.0 | 5.6 | 0.4 | 0.7 | 0.7 |
| 2-2 | 1500 | 2.0 | 4.0 | 2.7 | 2.7 | 5.6 | 0.4 | 0.5 | 1.1 |
| 2-3 | 950 | 1.5 | 2.0 | 1.2 | 1.2 | 4.7 | 0.4 | 0.7 | 1.1 |
| 2-4 | 1500 | 1.5 | 3.0 | 1.8 | 1.8 | 5.3 | 0.4 | 0.6 | 1.0 |
| 2-5 | 1500 | 1.5 | 5.0 | 3.0 | 3.0 | 5.8 | 0.3 | 0.6 | 0.9 |
| 2-6 | 1500 | 1.5 | 6.0 | 3.6 | 3.6 | 6.0 | 0.3 | 0.6 | 0.8 |
| 2-7 | 1500 | 1.5 | 4.1 | 2.5 | 2.5 | 6.2 | 0.2 | 0.4 | 0.5 |
| 2-8 | 1500 | 1.5 | 4.0 | 2.4 | 2.4 | — | 0.3 | 0.5 | 0.8 |
| 2-9 | 1500 | 1.5 | 4.0 | 2.4 | 2.4 | 5.6 | 0.4 | 0.6 | 0.9 |
| 2-10 | 1500 | 1.5 | 4.0 | 2.4 | 2.4 | 2.4 | 0.4 | 0.7 | 1.0 |
| 2-11 | 1500 | 1.5 | 4.0 | 2.4 | 2.4 | 6.8 | 0.1 | 0.1 | 0.2 |
| 2-12 | 317 | 1.5 | 4.0 | 2.4 | 2.4 | 4.0 | 1.0 | 1.7 | 2.5 |
| 2-13 | 337 | 1.5 | 0.4 | 0.2 | 0.2 | 2.4 | 2.5 | 4.2 | 6.3 |
| min. | | 1.0 | 0.4 | 0.2 | 0.2 | 2.4 | 0.1 | 0.1 | 0.2 |
| max. | | 2.0 | 6.0 | 3.6 | 3.6 | 6.8 | 2.5 | 4.2 | 6.3 |

CBP = Carbopol 71 G
LUT = Poloxamer 188 (Lutrol ® F68)
PEG = Polyethylene glycol (Macrogol 6,000)
HPMC = hydroxypropylmethylcellulose (HPMC 100,000)
API = active pharmaceutical ingredient (Tramadol HCl)

The invention claimed is:

1. A pharmaceutical dosage form having a breaking strength of at least 300 N and comprising:
   a pharmacologically active compound,
   an anionic polymer bearing carboxylic groups, wherein the anionic polymer is derived from an ethylenically unsaturated monomer selected from (alk)acrylic acids, (alk)acrylic anhydrides, alkyl (alk)acrylates, or a combination thereof, wherein the anionic polymer is cross-linked with at least one cross-linking agent selected from the group consisting of allyl sucrose, allyl pentaerythritol, divinyl glycol, divinyl polyethylene glycol and (meth)acrylic acid esters of diols, and wherein the content of the anionic polymer is ≥20 wt.-%, based on the total weight of the pharmaceutical dosage form, and
   a nonionic surfactant.

2. The pharmaceutical dosage form according to claim 1, which either does not contain any polyalkylene oxide having an average molecular weight of at least 200,000 g/mol, or wherein the total content of polyalkylene oxide(s) having an average molecular weight of at least 200,000 g/mol is ≤35 wt.-%, based on the total weight of the pharmaceutical dosage form.

3. The pharmaceutical dosage form according to claim 1, wherein the pharmacologically active compound is an opioid.

4. The pharmaceutical dosage form according to claim 1, wherein the nonionic surfactant
   (i) in pure water at a concentration of 25 wt.-% forms an aqueous dispersion having a viscosity $\eta_1$ at a temperature of 20° C. and a viscosity $\eta_2$ at a temperature of more than 20° C., where $\eta_2 > \eta_1$; and/or
   (ii) has an HLB value of at least 20, and/or
   (iii) has a surface tension in 0.1% aqueous solution at 30° C. of at least 35 dynes/cm; and/or
   (iv) has a viscosity of at most 4000 mPa·s, measured at 70° C. using a model LVF or LVT Brookfield viscosimeter.

5. The pharmaceutical dosage form according to claim 1, wherein the nonionic surfactant is a synthetic copolymer of ethylene oxide and propylene oxide.

6. The pharmaceutical dosage form according to claim 1, wherein the nonionic surfactant is selected from block copolymers according to general formula (I-a)

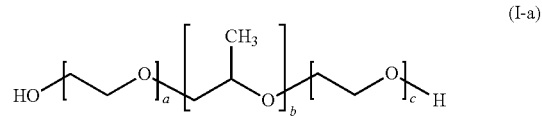

wherein a and c are each independently an integer of from 5 to 300, and b is an integer of from 10 to 100;
and/or block copolymers according to general formula (I-b)

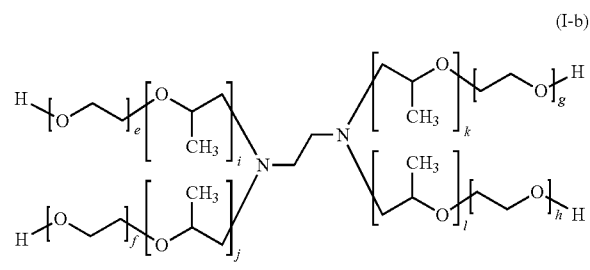

wherein e, f, g and h are each independently an integer of from 1 to 150, and i, j, k and l are each independently an integer of from 2 to 50.

7. The pharmaceutical dosage form according to claim 1, wherein the content of the nonionic surfactant is at least 10 wt.-%, based on the total weight of the pharmaceutical dosage form.

8. The pharmaceutical dosage form according to claim 1, wherein the pharmacologically active compound is embedded in a prolonged release matrix comprising the anionic polymer and the optionally present nonionic surfactant.

9. The pharmaceutical dosage form according to claim 1, which is configured for administration once daily or twice daily.

10. The pharmaceutical dosage form according to claim 1, which is thermoformed.

11. The pharmaceutical dosage form according to claim 1, which is tamper-resistant.

12. A method of treating pain in a patient in need thereof, said method comprising administering to said patient a dosage form according to claim 3.

13. The pharmaceutical dosage form according to claim 2, which does not contain any polyalkylene oxide having an average molecular weight of at least 200,000 g/mol.

\* \* \* \* \*